(12) United States Patent
Holman et al.

(10) Patent No.: US 10,192,037 B2
(45) Date of Patent: *Jan. 29, 2019

(54) REPORTING SYSTEM AND METHOD FOR INGESTIBLE PRODUCT PREPARATION SYSTEM AND METHOD

(75) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwah LLC, Bellevue, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/199,544

(22) Filed: Aug. 31, 2011

(65) Prior Publication Data
US 2013/0054267 A1 Feb. 28, 2013

Related U.S. Application Data

(63) Continuation-in-part of application No. 13/199,361, filed on Aug. 26, 2011, and a continuation-in-part of
(Continued)

(51) Int. Cl.
*G06F 19/00* (2018.01)
*G09B 19/00* (2006.01)
(Continued)

(52) U.S. Cl.
CPC .......... *G06F 19/3475* (2013.01); *G06F 19/00* (2013.01); *G06Q 30/02* (2013.01);
(Continued)

(58) Field of Classification Search
CPC ........ G06Q 50/22; G06Q 50/24; G06Q 30/02; G06F 19/3475; G06F 19/00; G16H 20/90; G16H 20/60; G16H 20/70; G09B 19/0092
(Continued)

(56) References Cited

U.S. PATENT DOCUMENTS

| 22,225 A | 12/1858 | Berry |
| 88,023 A | 3/1869 | Estell |

(Continued)

FOREIGN PATENT DOCUMENTS

| EP | 1 469 431 B1 | 9/2009 |
| NL | 2003661 C | 4/2011 |

(Continued)

OTHER PUBLICATIONS

U.S. Appl. No. 13/435,591, Holman et al.
(Continued)

*Primary Examiner* — Christopher L Gilligan

(57) ABSTRACT

A computationally implemented system and method that is designed to, but is not limited to: electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information; and electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being
(Continued)

associated with the particular individual living being. In addition to the foregoing, other method aspects are described in the claims, drawings, and text forming a part of the present disclosure.

51 Claims, 43 Drawing Sheets

Related U.S. Application Data application No. 13/199,481, filed on Aug. 30, 2011, now Pat. No. 9,600,850, and a continuation of application No. 13/199,545, filed on Aug. 31, 2011, now Pat. No. 9,240,028.

(51) Int. Cl.
  *G16H 20/60* (2018.01)
  *G06Q 30/02* (2012.01)
  *G16H 20/70* (2018.01)
  *G16H 20/90* (2018.01)

(52) U.S. Cl.
  CPC ......... *G09B 19/0092* (2013.01); *G16H 20/60* (2018.01); *G16H 20/70* (2018.01); *G16H 20/90* (2018.01)

(58) Field of Classification Search
  USPC .......................................... 705/2–3; 434/127
  See application file for complete search history.

(56) References Cited

U.S. PATENT DOCUMENTS

| | | |
|---|---|---|
| 116,634 A | 7/1871 | Schwerin |
| 260,918 A | 7/1882 | Yule et al. |
| 249,129 A | 2/1884 | Heffernan |
| 303,972 A | 8/1884 | Barton et al. |
| 1,570,405 A | 1/1926 | Salerno |
| 3,040,935 A | 6/1962 | Lopata |
| 3,702,583 A | 11/1972 | Rullman |
| 3,859,904 A | 1/1975 | Carriazo |
| 4,076,846 A | 2/1978 | Nakatsuka et al. |
| 4,127,232 A | 11/1978 | Gagliardo et al. |
| 4,135,077 A | 1/1979 | Wills |
| 4,293,296 A | 10/1981 | Caiello et al. |
| 4,452,132 A | 6/1984 | Miller et al. |
| 4,634,597 A | 1/1987 | Spiel et al. |
| 4,666,204 A | 5/1987 | Reinholtz |
| 4,681,000 A | 7/1987 | Wolters |
| 4,723,614 A | 2/1988 | Lahti |
| 4,796,182 A | 1/1989 | Duboff |
| 4,797,818 A | 1/1989 | Cotter |
| 4,974,747 A | 12/1990 | Ahlstrom |
| 5,121,677 A | 6/1992 | Le Claire et al. |
| 5,132,914 A | 7/1992 | Cahlander et al. |
| 5,176,922 A | 1/1993 | Balsano et al. |
| 5,197,376 A | 3/1993 | Bird et al. |
| 5,228,382 A | 7/1993 | Hayashi et al. |
| 5,261,150 A | 11/1993 | Grube et al. |
| 5,408,443 A | 4/1995 | Weinberger |
| 5,417,989 A | 5/1995 | Atwood et al. |
| 5,511,594 A | 4/1996 | Brennan et al. |
| 5,522,309 A | 6/1996 | Mizobuchi et al. |
| 5,522,310 A | 6/1996 | Black, Sr. et al. |
| 5,540,943 A | 7/1996 | Naramura |
| 5,583,129 A | 12/1996 | Spona et al. |
| 5,598,947 A | 2/1997 | Smith |
| 5,615,778 A | 4/1997 | Kaiser et al. |
| 5,697,043 A | 12/1997 | Baskaran et al. |
| 5,731,020 A | 3/1998 | Russo |
| 5,736,940 A | 4/1998 | Burgener |
| 5,762,971 A | 6/1998 | Schirmer |
| 5,820,906 A | 10/1998 | Akesson et al. |
| 6,032,574 A | 3/2000 | Brayton et al. |
| 6,048,191 A | 4/2000 | Beltrami |
| 6,105,818 A | 8/2000 | Speranza |
| 6,112,182 A | 8/2000 | Akers et al. |
| 6,137,686 A | 10/2000 | Saye |
| 6,194,017 B1 | 2/2001 | Woodward et al. |
| 6,200,125 B1 | 3/2001 | Akutagawa |
| 6,202,923 B1 | 3/2001 | Boyer et al. |
| 6,236,974 B1 | 5/2001 | Kolawa et al. |
| 6,245,556 B1 | 6/2001 | Sako et al. |
| 6,251,456 B1 | 6/2001 | Maul et al. |
| 6,268,004 B1 | 7/2001 | Hayashi |
| 6,280,784 B1 | 8/2001 | Yang et al. |
| 6,280,785 B1 | 8/2001 | Yang et al. |
| 6,280,786 B1 | 8/2001 | Williams et al. |
| 6,317,686 B1 | 11/2001 | Ran |
| 6,359,239 B1 | 3/2002 | Missler et al. |
| 6,376,000 B1 | 4/2002 | Waters |
| 6,415,555 B1 | 7/2002 | Montague |
| 6,490,870 B1 | 12/2002 | Efremkine |
| 6,618,062 B1 | 9/2003 | Brown et al. |
| 6,622,064 B2 | 9/2003 | Bartholomew et al. |
| 6,637,432 B2 | 10/2003 | Wakefield et al. |
| 6,644,359 B1 | 11/2003 | Wertheim |
| 6,646,659 B1 | 11/2003 | Brown et al. |
| 6,658,990 B1 | 12/2003 | Henning et al. |
| 6,660,317 B1 | 12/2003 | Akutagawa |
| 6,660,982 B2 | 12/2003 | Thorneywork |
| 6,711,460 B1 | 3/2004 | Reese |
| 6,802,433 B2 | 10/2004 | Leykin et al. |
| 6,841,185 B2 | 1/2005 | Sargent et al. |
| 6,843,166 B1 | 1/2005 | Li |
| 6,859,215 B1 | 2/2005 | Brown et al. |
| 6,865,261 B1 | 3/2005 | Rao et al. |
| 6,998,087 B1 | 2/2006 | Hanson et al. |
| 7,006,893 B2 | 2/2006 | Hart et al. |
| 7,027,996 B2 | 4/2006 | Levinson |
| 7,054,909 B1 | 5/2006 | Ohkubo et al. |
| 7,080,597 B2 | 7/2006 | Ando |
| 7,098,794 B2 | 8/2006 | Lindsay et al. |
| 7,110,964 B2 | 9/2006 | Tengler et al. |
| 7,183,518 B2 | 2/2007 | Near et al. |
| 7,187,960 B2 | 3/2007 | Abreu |
| 7,188,082 B2 | 3/2007 | Keane et al. |
| 7,200,644 B1 | 4/2007 | Flanagan |
| 7,231,917 B2 | 6/2007 | Frederiksen |
| 7,243,789 B2 | 7/2007 | Discko, Jr. |
| 7,281,468 B2 | 10/2007 | Frem |
| 7,286,258 B2 | 10/2007 | Schnoebelen et al. |
| 7,295,889 B2 | 11/2007 | Lähteenmäki |
| 7,299,982 B2 | 11/2007 | Kreiner et al. |
| 7,319,780 B2 | 1/2008 | Fedorovskaya et al. |
| 7,343,174 B2 | 3/2008 | Suryanarayana et al. |
| 7,364,068 B1 | 4/2008 | Strubbe et al. |
| 7,392,193 B2 | 6/2008 | Mault |
| 7,395,134 B2 | 7/2008 | Bartholomew et al. |
| 7,415,375 B2 | 8/2008 | Shakman et al. |
| 7,451,015 B2 | 11/2008 | Mazur et al. |
| 7,457,685 B2 | 11/2008 | D'Silva |
| 7,555,360 B1 | 6/2009 | Green et al. |
| 7,571,586 B1 | 8/2009 | Morales |
| 7,625,198 B2 | 12/2009 | Lipson et al. |
| 7,630,790 B2 | 12/2009 | Handfield et al. |
| 7,680,690 B1 | 3/2010 | Catalano |
| 7,698,566 B1 | 4/2010 | Stone |
| 7,747,345 B2 | 6/2010 | Ohmura et al. |
| 7,762,181 B2 | 7/2010 | Boland et al. |
| 7,783,379 B2 | 8/2010 | Beane et al. |
| 7,818,089 B2 | 10/2010 | Hanna et al. |
| 7,842,323 B1 | 11/2010 | White |
| 7,858,136 B2 | 12/2010 | Park et al. |
| 7,884,953 B1 | 2/2011 | Willcocks et al. |
| 7,961,916 B2 | 6/2011 | Wang et al. |
| 7,974,873 B2 | 7/2011 | Simmons et al. |
| 8,007,847 B2 | 8/2011 | Biderman et al. |
| 8,027,748 B2 | 9/2011 | Handfield et al. |
| 8,085,135 B2 | 12/2011 | Cohen Alloro et al. |
| 8,173,186 B2 | 5/2012 | Kuwabara et al. |
| 8,190,447 B2 | 5/2012 | Hungerford et al. |

(56) References Cited

U.S. PATENT DOCUMENTS

| | | |
|---|---|---|
| 8,204,757 B2 | 6/2012 | Carlson et al. |
| 8,249,946 B2 | 8/2012 | Froseth et al. |
| 8,306,655 B2 | 11/2012 | Newman |
| 8,321,364 B1 | 11/2012 | Gharpure et al. |
| 8,370,176 B2 | 2/2013 | Vespasiani |
| 8,412,369 B2 | 4/2013 | Ames, II et al. |
| 8,412,588 B1 | 4/2013 | Bodell et al. |
| 8,504,440 B1 | 8/2013 | Kolawa et al. |
| 8,521,326 B1 | 8/2013 | Holtje |
| 8,583,511 B2 | 11/2013 | Hendrickson |
| 8,594,838 B2 | 11/2013 | Selker et al. |
| 8,594,935 B2 | 11/2013 | Cioffi et al. |
| 8,688,277 B2 | 4/2014 | Studor et al. |
| 8,744,618 B2 | 6/2014 | Peters et al. |
| 8,793,588 B2 | 7/2014 | DiPietro |
| 8,846,122 B2 | 9/2014 | Rumbaut et al. |
| 9,165,117 B2 | 10/2015 | Teller et al. |
| 9,240,028 B2 | 1/2016 | Holman et al. |
| 9,703,928 B2 | 7/2017 | Mochizuki et al. |
| 9,744,721 B2 | 8/2017 | Klaber |
| 2001/0005830 A1 | 6/2001 | Kuroyanagi |
| 2001/0028308 A1 | 10/2001 | De La Huerga |
| 2001/0036495 A1 | 11/2001 | Ganan-Calvo |
| 2002/0029149 A1 | 3/2002 | Nishina |
| 2002/0035503 A1 | 3/2002 | Matsumoto |
| 2002/0042726 A1 | 4/2002 | Mayaud |
| 2002/0049652 A1 | 4/2002 | Moore et al. |
| 2002/0050526 A1 | 5/2002 | Swartz et al. |
| 2002/0055878 A1 | 5/2002 | Burton et al. |
| 2002/0069097 A1 | 6/2002 | Conrath |
| 2002/0081356 A1 | 6/2002 | Bebiak et al. |
| 2002/0116634 A1* | 8/2002 | Okubo .................. G06Q 10/06 726/26 |
| 2002/0138201 A1 | 9/2002 | Greensides |
| 2002/0156682 A1 | 10/2002 | DiPietro |
| 2002/0165787 A1 | 11/2002 | Bates et al. |
| 2002/0192572 A1 | 12/2002 | Lau |
| 2003/0017248 A1 | 1/2003 | Gray |
| 2003/0024946 A1 | 2/2003 | Severino |
| 2003/0050854 A1 | 3/2003 | Showghi et al. |
| 2003/0051606 A1 | 3/2003 | Cusenza et al. |
| 2003/0069745 A1 | 4/2003 | Zenko |
| 2003/0071806 A1 | 4/2003 | Annand |
| 2003/0079612 A1 | 5/2003 | Con |
| 2003/0099157 A1 | 5/2003 | Quine |
| 2003/0105555 A1 | 6/2003 | Lunak et al. |
| 2003/0121929 A1 | 7/2003 | Liff et al. |
| 2003/0125836 A1 | 7/2003 | Chirnomas |
| 2003/0125963 A1 | 7/2003 | Haken |
| 2003/0125986 A1 | 7/2003 | Collosi |
| 2003/0185948 A1 | 10/2003 | Garwood |
| 2003/0197005 A1 | 10/2003 | Huegerich et al. |
| 2003/0208113 A1 | 11/2003 | Mault et al. |
| 2003/0208409 A1 | 11/2003 | Mault |
| 2003/0219527 A1 | 11/2003 | Sasaki et al. |
| 2003/0236682 A1* | 12/2003 | Heyer .................. G06F 19/322 705/2 |
| 2003/0236706 A1 | 12/2003 | Weiss |
| 2004/0015403 A1 | 1/2004 | Moskowitz et al. |
| 2004/0025701 A1 | 2/2004 | Colston et al. |
| 2004/0044469 A1 | 3/2004 | Bender et al. |
| 2004/0044489 A1 | 3/2004 | Jones et al. |
| 2004/0045579 A1 | 3/2004 | Miki et al. |
| 2004/0049407 A1 | 3/2004 | Rosenberg |
| 2004/0054554 A1 | 3/2004 | Barts et al. |
| 2004/0073448 A1 | 4/2004 | Barts et al. |
| 2004/0073449 A1 | 4/2004 | Yang |
| 2004/0091843 A1 | 5/2004 | Albro et al. |
| 2004/0093265 A1 | 5/2004 | Ramchandani et al. |
| 2004/0093268 A1 | 5/2004 | Ramchandani et al. |
| 2004/0103033 A1 | 5/2004 | Reade et al. |
| 2004/0117205 A1 | 6/2004 | Reardan et al. |
| 2004/0131659 A1 | 7/2004 | Gibson et al. |
| 2004/0143503 A1 | 7/2004 | Suthar |
| 2004/0151820 A1 | 8/2004 | Harris |
| 2004/0158350 A1 | 8/2004 | Ostergaard et al. |
| 2004/0158499 A1 | 8/2004 | Dev et al. |
| 2004/0172169 A1 | 9/2004 | Wright, IV et al. |
| 2004/0183796 A1 | 9/2004 | Velde et al. |
| 2004/0193325 A1 | 9/2004 | Bonderud et al. |
| 2004/0193495 A1 | 9/2004 | Kim |
| 2004/0214597 A1 | 10/2004 | Suryanarayana et al. |
| 2004/0226775 A1 | 11/2004 | Takatama et al. |
| 2004/0238555 A1 | 12/2004 | Parks |
| 2004/0246819 A1 | 12/2004 | Quine |
| 2004/0250842 A1 | 12/2004 | Adams et al. |
| 2004/0263319 A1 | 12/2004 | Huomo |
| 2005/0023710 A1 | 2/2005 | Brodkin et al. |
| 2005/0038719 A1 | 2/2005 | Young et al. |
| 2005/0048461 A1* | 3/2005 | Lahteenmaki .................. 435/3 |
| 2005/0059849 A1 | 3/2005 | Liu |
| 2005/0060063 A1 | 3/2005 | Reichelt et al. |
| 2005/0065640 A1 | 3/2005 | Mallett et al. |
| 2005/0079257 A1 | 4/2005 | Neto |
| 2005/0080520 A1 | 4/2005 | Kline et al. |
| 2005/0080650 A1 | 4/2005 | Noel |
| 2005/0090425 A1 | 4/2005 | Reardan et al. |
| 2005/0098169 A1 | 5/2005 | Frederiksen |
| 2005/0113968 A1 | 5/2005 | Williams et al. |
| 2005/0114149 A1 | 5/2005 | Rodriguez et al. |
| 2005/0131738 A1* | 6/2005 | Morris .................. 705/2 |
| 2005/0157148 A1 | 7/2005 | Baker et al. |
| 2005/0160052 A1 | 7/2005 | Schneider et al. |
| 2005/0171663 A1 | 8/2005 | Mittelsteadt et al. |
| 2005/0193901 A1 | 9/2005 | Buehler |
| 2005/0209915 A1 | 9/2005 | Saluccio |
| 2005/0226975 A1 | 10/2005 | Drouillard |
| 2005/0230472 A1 | 10/2005 | Chang |
| 2005/0233011 A1 | 10/2005 | Beavers |
| 2005/0241497 A1 | 11/2005 | Cantu |
| 2005/0251289 A1 | 11/2005 | Bonney et al. |
| 2005/0267811 A1 | 12/2005 | Almblad |
| 2005/0280544 A1 | 12/2005 | Mishelevich |
| 2006/0015289 A1 | 1/2006 | Shakman et al. |
| 2006/0053184 A1 | 3/2006 | Grana |
| 2006/0064037 A1 | 3/2006 | Shalon et al. |
| 2006/0081653 A1 | 4/2006 | Boland et al. |
| 2006/0108415 A1 | 5/2006 | Thomas et al. |
| 2006/0111976 A1 | 5/2006 | Pompushko |
| 2006/0147581 A1 | 7/2006 | Svendsen et al. |
| 2006/0161453 A1 | 7/2006 | Kost et al. |
| 2006/0178943 A1 | 8/2006 | Rollinson et al. |
| 2006/0182240 A1 | 8/2006 | Schelberg, Jr. et al. |
| 2006/0191885 A1 | 8/2006 | Near et al. |
| 2006/0224419 A1 | 10/2006 | Servizio et al. |
| 2006/0237523 A1 | 10/2006 | Carlson et al. |
| 2006/0259188 A1 | 11/2006 | Berg |
| 2006/0260601 A1 | 11/2006 | Schedeler et al. |
| 2006/0263501 A1 | 11/2006 | Oghafua et al. |
| 2006/0277066 A1 | 12/2006 | Hungerford et al. |
| 2006/0278093 A1 | 12/2006 | Biderman et al. |
| 2006/0286218 A1 | 12/2006 | Salzman |
| 2007/0027432 A1 | 2/2007 | Radford et al. |
| 2007/0037567 A1 | 2/2007 | Ungless et al. |
| 2007/0038476 A1 | 2/2007 | Sternlicht |
| 2007/0038727 A1 | 2/2007 | Bailey et al. |
| 2007/0048407 A1 | 3/2007 | Collins et al. |
| 2007/0055550 A1 | 3/2007 | Courtney et al. |
| 2007/0055694 A1 | 3/2007 | Ruge et al. |
| 2007/0057039 A1 | 3/2007 | Carlson et al. |
| 2007/0061170 A1 | 3/2007 | Lorsch |
| 2007/0061209 A1 | 3/2007 | Jackson |
| 2007/0062156 A1 | 3/2007 | Kim |
| 2007/0083494 A1 | 4/2007 | Carlson et al. |
| 2007/0088624 A1 | 4/2007 | Vaughn et al. |
| 2007/0092614 A1 | 4/2007 | Waldock |
| 2007/0150371 A1 | 6/2007 | Gangji |
| 2007/0150375 A1 | 6/2007 | Yang |
| 2007/0151984 A1 | 7/2007 | Baker et al. |
| 2007/0168205 A1 | 7/2007 | Carlson et al. |
| 2007/0170049 A1 | 7/2007 | Mansur |
| 2007/0170195 A1 | 7/2007 | Segiet et al. |
| 2007/0183633 A1 | 8/2007 | Hoffmann |
| 2007/0185615 A1 | 8/2007 | Bossi et al. |

(56) References Cited

U.S. PATENT DOCUMENTS

| | | |
|---|---|---|
| 2007/0185785 A1 | 8/2007 | Carlson et al. |
| 2007/0191689 A1 | 8/2007 | Elitok |
| 2007/0192715 A1 | 8/2007 | Kataria et al. |
| 2007/0208454 A1 | 9/2007 | Forrester et al. |
| 2007/0231435 A1 | 10/2007 | Ream et al. |
| 2007/0260487 A1 | 11/2007 | Bartfeld et al. |
| 2007/0267441 A1 | 11/2007 | van Opstal et al. |
| 2007/0271001 A1 | 11/2007 | Ratnakar |
| 2007/0275690 A1 | 11/2007 | Hunter et al. |
| 2007/0292573 A1 | 12/2007 | Smith |
| 2007/0294129 A1* | 12/2007 | Froseth .................. G06Q 10/08 705/7.32 |
| 2008/0059226 A1 | 3/2008 | Melker et al. |
| 2008/0077440 A1 | 3/2008 | Doron |
| 2008/0084450 A1 | 4/2008 | Silverbrook |
| 2008/0114678 A1 | 5/2008 | Bennett et al. |
| 2008/0124433 A1 | 5/2008 | Yelden et al. |
| 2008/0125897 A1 | 5/2008 | DiGianfilippo et al. |
| 2008/0126220 A1 | 5/2008 | Baril et al. |
| 2008/0126985 A1 | 5/2008 | Baril et al. |
| 2008/0141315 A1 | 6/2008 | Ogilvie |
| 2008/0162181 A1 | 7/2008 | Ben-Haim et al. |
| 2008/0163762 A1 | 7/2008 | Weiss |
| 2008/0171967 A1 | 7/2008 | Blomguist et al. |
| 2008/0172261 A1 | 7/2008 | Albertson et al. |
| 2008/0173711 A1 | 7/2008 | Handfield et al. |
| 2008/0189143 A1 | 8/2008 | Wurster |
| 2008/0195247 A1 | 8/2008 | Mallett et al. |
| 2008/0224823 A1 | 9/2008 | Lawson et al. |
| 2008/0249859 A1 | 10/2008 | Angell et al. |
| 2008/0249865 A1 | 10/2008 | Angell et al. |
| 2008/0260918 A1 | 10/2008 | Lai et al. |
| 2008/0272138 A1 | 11/2008 | Ross et al. |
| 2008/0281915 A1 | 11/2008 | Elad et al. |
| 2008/0288287 A1 | 11/2008 | Stanners |
| 2008/0314918 A1 | 12/2008 | Nuriely |
| 2009/0012433 A1 | 1/2009 | Fernstrom et al. |
| 2009/0029016 A1 | 1/2009 | Pfister et al. |
| 2009/0043176 A1 | 2/2009 | Nakajima et al. |
| 2009/0087819 A1 | 4/2009 | Adachi et al. |
| 2009/0094033 A1 | 4/2009 | Mozer et al. |
| 2009/0099944 A1 | 4/2009 | Robinson et al. |
| 2009/0105875 A1 | 4/2009 | Wiles |
| 2009/0106313 A1 | 4/2009 | Boldyga |
| 2009/0106316 A1 | 4/2009 | Kubono et al. |
| 2009/0106826 A1* | 4/2009 | Palestrant .............. G06F 21/35 726/7 |
| 2009/0112683 A1 | 4/2009 | Hamilton, II et al. |
| 2009/0112754 A1 | 4/2009 | Seifert et al. |
| 2009/0112782 A1 | 4/2009 | Cross et al. |
| 2009/0130449 A1 | 5/2009 | El-Siblani |
| 2009/0132379 A1 | 5/2009 | Baril et al. |
| 2009/0142223 A1 | 6/2009 | Hyde et al. |
| 2009/0149717 A1 | 6/2009 | Brauer et al. |
| 2009/0161907 A1 | 6/2009 | Healey et al. |
| 2009/0164897 A1 | 6/2009 | Amer-Yahia et al. |
| 2009/0167553 A1 | 7/2009 | Hong et al. |
| 2009/0192898 A1 | 7/2009 | Baril |
| 2009/0198547 A1 | 8/2009 | Sudak |
| 2009/0199105 A1 | 8/2009 | Kamada et al. |
| 2009/0209240 A1 | 8/2009 | Mahowald |
| 2009/0218363 A1 | 9/2009 | Terzini |
| 2009/0234712 A1 | 9/2009 | Kolawa et al. |
| 2009/0236333 A1 | 9/2009 | Ben-Shmuel et al. |
| 2009/0236334 A1 | 9/2009 | Ben-Shmuel et al. |
| 2009/0236335 A1 | 9/2009 | Ben-Shmuel et al. |
| 2009/0242620 A1 | 10/2009 | Sahuguet |
| 2009/0254531 A1 | 10/2009 | Walker et al. |
| 2009/0259559 A1 | 10/2009 | Carroll et al. |
| 2009/0259688 A1 | 10/2009 | Do et al. |
| 2009/0261175 A1 | 10/2009 | Kauppinen et al. |
| 2009/0267895 A1* | 10/2009 | Bunch ..................... 345/157 |
| 2009/0271004 A1 | 10/2009 | Zecchin et al. |
| 2009/0294521 A1 | 12/2009 | de la Huerga |
| 2009/0295569 A1 | 12/2009 | Corwin et al. |
| 2009/0295575 A1 | 12/2009 | Kennedy |
| 2009/0297668 A1 | 12/2009 | Cantu |
| 2009/0299645 A1 | 12/2009 | Colby et al. |
| 2009/0307139 A1 | 12/2009 | Mardikar et al. |
| 2009/0313125 A1 | 12/2009 | Roh et al. |
| 2009/0317519 A1 | 12/2009 | Lavie et al. |
| 2009/0326516 A1 | 12/2009 | Bangera et al. |
| 2010/0017296 A1 | 1/2010 | Spignesi, Jr. et al. |
| 2010/0038416 A1 | 2/2010 | Canora |
| 2010/0038594 A1 | 2/2010 | Bohlig et al. |
| 2010/0042427 A1 | 2/2010 | Graham et al. |
| 2010/0043834 A1 | 2/2010 | Scheringer |
| 2010/0045705 A1 | 2/2010 | Vertegaal et al. |
| 2010/0047410 A1 | 2/2010 | Lichtenstein |
| 2010/0052900 A1 | 3/2010 | Covannon et al. |
| 2010/0055257 A1 | 3/2010 | Hervig |
| 2010/0062169 A1 | 3/2010 | Pierre |
| 2010/0063889 A1 | 3/2010 | Proctor, Jr. et al. |
| 2010/0087155 A1 | 4/2010 | Dubost |
| 2010/0097180 A1 | 4/2010 | Cardullo |
| 2010/0100237 A1 | 4/2010 | Ratnakar |
| 2010/0106523 A1* | 4/2010 | Kalamas .............. 705/3 |
| 2010/0106607 A1 | 4/2010 | Riddiford et al. |
| 2010/0121156 A1 | 5/2010 | Yoo |
| 2010/0121669 A1 | 5/2010 | Madigan |
| 2010/0121722 A1 | 5/2010 | Vawter |
| 2010/0125362 A1 | 5/2010 | Canora et al. |
| 2010/0136666 A1 | 6/2010 | Kobayashi et al. |
| 2010/0139992 A1 | 6/2010 | Delia et al. |
| 2010/0145506 A1 | 6/2010 | Waugh et al. |
| 2010/0160745 A1 | 6/2010 | Hills et al. |
| 2010/0161345 A1* | 6/2010 | Cain et al. .............. 705/2 |
| 2010/0161600 A1 | 6/2010 | Higgins et al. |
| 2010/0167648 A1 | 7/2010 | Doutriaux |
| 2010/0181374 A1 | 7/2010 | Martis et al. |
| 2010/0189842 A1 | 7/2010 | Toren |
| 2010/0204676 A1 | 8/2010 | Cardullo |
| 2010/0206765 A1 | 8/2010 | Fonte |
| 2010/0235201 A1 | 9/2010 | McEvoy |
| 2010/0250384 A1 | 9/2010 | Bhargava |
| 2010/0256993 A1* | 10/2010 | Vespasiani .............. 705/3 |
| 2010/0259719 A1 | 10/2010 | Sabeta |
| 2010/0268378 A1 | 10/2010 | Sharpley |
| 2010/0268380 A1 | 10/2010 | Waugh et al. |
| 2010/0268792 A1 | 10/2010 | Butler et al. |
| 2010/0275625 A1 | 11/2010 | Lowenstein |
| 2010/0286632 A1 | 11/2010 | Dos Santos |
| 2010/0291515 A1 | 11/2010 | Pinnisi et al. |
| 2010/0292998 A1 | 11/2010 | Bodlaender et al. |
| 2010/0299158 A1 | 11/2010 | Siegel |
| 2010/0303972 A1 | 12/2010 | Srivastava |
| 2010/0305974 A1 | 12/2010 | Patch et al. |
| 2010/0310737 A1 | 12/2010 | Someya et al. |
| 2010/0312143 A1 | 12/2010 | Kim |
| 2010/0312385 A1 | 12/2010 | Deuber |
| 2010/0312601 A1 | 12/2010 | Lin |
| 2010/0320189 A1 | 12/2010 | Buchheit |
| 2010/0328099 A1 | 12/2010 | Wachman et al. |
| 2010/0332140 A1 | 12/2010 | Joyce et al. |
| 2010/0332250 A1 | 12/2010 | Simpson et al. |
| 2011/0000923 A1 | 1/2011 | Morales |
| 2011/0004624 A1 | 1/2011 | Bansai et al. |
| 2011/0009715 A1 | 1/2011 | O'Reilly et al. |
| 2011/0022225 A1 | 1/2011 | Rothschild |
| 2011/0022298 A1 | 1/2011 | Kronberg |
| 2011/0027432 A1 | 2/2011 | Loeser |
| 2011/0031236 A1* | 2/2011 | Ben-Shmuel et al. ........ 219/620 |
| 2011/0035338 A1 | 2/2011 | Kagan et al. |
| 2011/0040660 A1 | 2/2011 | Allison et al. |
| 2011/0054678 A1 | 3/2011 | Thompson |
| 2011/0055044 A1 | 3/2011 | Wiedl |
| 2011/0060457 A1* | 3/2011 | De Vrught ................ A61J 1/03 700/241 |
| 2011/0076349 A1 | 3/2011 | Yoshihara et al. |
| 2011/0080457 A1 | 4/2011 | Nagamine et al. |
| 2011/0087076 A1* | 4/2011 | Brynelsen et al. .......... 600/300 |
| 2011/0124996 A1 | 5/2011 | Reinke et al. |
| 2011/0133005 A1 | 6/2011 | Chesack |
| 2011/0160902 A1 | 6/2011 | Postins |

(56) References Cited

U.S. PATENT DOCUMENTS

| | | |
|---|---|---|
| 2011/0166881 A1* | 7/2011 | Brazzo et al. ............... 705/3 |
| 2011/0173062 A1 | 7/2011 | Chen et al. |
| 2011/0180441 A1* | 7/2011 | Bach ............... G06F 19/322 206/459.5 |
| 2011/0186624 A1 | 8/2011 | Wagner et al. |
| 2011/0208617 A1 | 8/2011 | Weiland |
| 2011/0218839 A1 | 9/2011 | Shamaiengar |
| 2011/0231212 A1 | 9/2011 | Hurley et al. |
| 2011/0231266 A1 | 9/2011 | Baril |
| 2011/0282712 A1 | 11/2011 | Amos et al. |
| 2011/0289572 A1* | 11/2011 | Skeel et al. ............... 726/7 |
| 2011/0300270 A1 | 12/2011 | Koppens |
| 2011/0307316 A1 | 12/2011 | Peters et al. |
| 2011/0313867 A9 | 12/2011 | Silver |
| 2011/0318717 A1 | 12/2011 | Adamowicz |
| 2011/0320037 A1 | 12/2011 | Frugone |
| 2012/0004770 A1 | 1/2012 | Ooyen et al. |
| 2012/0016745 A1 | 1/2012 | Hendrickson |
| 2012/0016754 A1 | 1/2012 | Jackson |
| 2012/0036046 A1 | 2/2012 | Anderson et al. |
| 2012/0041770 A1 | 2/2012 | Philippe |
| 2012/0041778 A1 | 2/2012 | Kraft |
| 2012/0088023 A1 | 4/2012 | Begun |
| 2012/0088212 A1 | 4/2012 | Knaan |
| 2012/0089249 A1 | 4/2012 | Rosenblum |
| 2012/0101914 A1 | 4/2012 | Kumar et al. |
| 2012/0131619 A1 | 5/2012 | Ogilvie |
| 2012/0136731 A1 | 5/2012 | Kidron et al. |
| 2012/0137325 A1 | 5/2012 | Ogilvie |
| 2012/0152125 A1 | 6/2012 | Yoakim et al. |
| 2012/0156337 A1 | 6/2012 | Studor et al. |
| 2012/0168985 A1 | 7/2012 | Kläber |
| 2012/0173271 A1* | 7/2012 | Omidi ............... 705/2 |
| 2012/0179665 A1 | 7/2012 | Baarman et al. |
| 2012/0196011 A1 | 8/2012 | Felix |
| 2012/0214140 A1 | 8/2012 | Brynelsen et al. |
| 2012/0232484 A1 | 9/2012 | Blomquist |
| 2012/0233002 A1 | 9/2012 | Abujbara |
| 2012/0246004 A1 | 9/2012 | Book et al. |
| 2012/0251688 A1 | 10/2012 | Zimmerman et al. |
| 2012/0251689 A1 | 10/2012 | Batchelder |
| 2012/0258216 A1 | 10/2012 | Wessels |
| 2012/0262039 A1 | 10/2012 | Daugbjerg et al. |
| 2012/0268259 A1* | 10/2012 | Igel ............... B60R 25/00 340/426.11 |
| 2012/0284126 A1 | 11/2012 | Giraud et al. |
| 2012/0290412 A1 | 11/2012 | Marovets |
| 2012/0303425 A1 | 11/2012 | Katzin et al. |
| 2012/0310760 A1* | 12/2012 | Phillips ............... G06Q 40/02 705/26.1 |
| 2012/0323208 A1 | 12/2012 | Bochenko et al. |
| 2012/0323707 A1 | 12/2012 | Urban |
| 2013/0006415 A1 | 1/2013 | Paydar et al. |
| 2013/0011529 A1 | 1/2013 | Belzowski et al. |
| 2013/0018356 A1 | 1/2013 | Prince et al. |
| 2013/0034633 A1 | 2/2013 | von Hasseln |
| 2013/0048023 A1 | 2/2013 | Holman et al. |
| 2013/0048037 A1 | 2/2013 | Holman et al. |
| 2013/0089642 A1 | 4/2013 | Lipson et al. |
| 2013/0092033 A1 | 4/2013 | Murphy et al. |
| 2013/0151268 A1 | 6/2013 | Fletcher |
| 2013/0158705 A1 | 6/2013 | Levy et al. |
| 2013/0171304 A1 | 7/2013 | Huntley |
| 2013/0189405 A1 | 7/2013 | Filliol et al. |
| 2013/0196035 A1 | 8/2013 | Passet et al. |
| 2013/0238118 A1 | 9/2013 | Haas |
| 2013/0273217 A1 | 10/2013 | Minvielle |
| 2013/0304529 A1 | 11/2013 | Phalake et al. |
| 2014/0013962 A1 | 1/2014 | Lipton et al. |
| 2014/0050811 A1 | 2/2014 | Lipton et al. |
| 2014/0236759 A1 | 8/2014 | Mirabile |
| 2014/0304055 A1 | 10/2014 | Faith |
| 2015/0151050 A1 | 6/2015 | Estes |
| 2015/0216201 A1 | 8/2015 | Bruckner et al. |
| 2015/0296865 A1 | 10/2015 | Holman et al. |
| 2015/0302375 A1 | 10/2015 | Holman et al. |

FOREIGN PATENT DOCUMENTS

| | | |
|---|---|---|
| WO | WO 03/056493 A1 | 7/2003 |
| WO | WO 2006/095212 A1 | 9/2006 |

OTHER PUBLICATIONS

U.S. Appl. No. 13/435,550, Holman et al.
U.S. Appl. No. 13/432,525, Holman et al.
U.S. Appl. No. 13/432,507, Holman et al.
U.S. Appl. No. 13/385,690, Holman et al.
U.S. Appl. No. 13/385,687, Holman et al.
U.S. Appl. No. 13/385,129, Holman et al.
U.S. Appl. No. 13/385,128, Holman et al.
U.S. Appl. No. 13/373,847, Holman et al.
U.S. Appl. No. 13/373,846, Holman et al.
U.S. Appl. No. 13/373,675, Holman et al.
U.S. Appl. No. 13/373,674, Holman et al.
U.S. Appl. No. 13/317,979, Holman et al.
U.S. Appl. No. 13/317,978, Holman et al.
U.S. Appl. No. 13/317,546, Holman et al.
U.S. Appl. No. 13/317,545, Holman et al.
U.S. Appl. No. 13/200,907, Holman et al.
U.S. Appl. No. 13/200,906, Holman et al.
U.S. Appl. No. 13/200,830, Holman et al.
U.S. Appl. No. 13/200,829, Holman et al.
U.S. Appl. No. 13/200,113, Holman et al.
U.S. Appl. No. 13/200,106, Holman et al.
U.S. Appl. No. 13/199,545, Holman et al.
U.S. Appl. No. 13/199,481, Holman et al.
U.S. Appl. No. 13/199,361, Holman et al.
"3D food printing"; PharmacyEscrow.com; printed on Apr. 4, 2012; 2 pages
Blain, Loz; "Cornucopia: Digital Gastronomy—could 3D printing be the next revolution in cooking?"; Gizmag; Jan. 14, 2010; 4 pages.
Broomfield, Mark; "The Future of Food Printing"; Fab@Home; Aug. 20, 2009; 1 page.
Coelho, Marcelo; "Cornucopia"; printed on Apr. 4, 2012; 1 page; located at fluid.media.mut.edu.
Cohen et al.; "Hydrocolloid Printing: A Novel Platform for Customized Food Production"; Twentieth Annual International Solid Freeform Fabrication Symposium, Austin, Texas; bearing a date of 2009; cover page and pp. 807-818.
Fawkes, Piers; "3D Food Printing", PSFK; Jan. 17, 2008; 8 pages.
Flatley, Joseph L.; "Ikea's kitchen of the future: 3D food printing, mood lighting, virtual Gordon Ramsay"; Engadget; printed on Apr. 4, 2012; 4 pages; AOL Inc.
McKendrick, Joe; "3D food 'printing': coming to a kitchen near you"; Smartplanet; Dec. 27, 2010; 6 pages; located at www.smartplanet.com/business/blog/business-brains.
Periard et al.; "Printing Food"; Cornell University; printed on Apr. 6, 2012; 11 pages; located at www.creativemachines.cornell.edu/papers/SFF07_Periard2.pdf •.
"Printed Meats!"; Fabbaloo; Aug. 23, 2010; 5 pages; Fabbaloo.
"Prototypes and Concept Designs for a Digital Gastronomy"; Cornucopia; printed on Apr. 4, 2012; 5 pages.
Sandhana, Lakshmi; "The printed future of Christmas dinner"; BBC News Technology; Dec. 24, 2010; 4 pages; MMXI.
Seth, Radhika; "Printing My Food by the Molecule"; Yanko Design; Mar. 2, 2010; 7 pages.
Seth, Radhika; "Surreal Food Is Real and Printed"; Yanko Design; Aug. 26, 2009; 6 pages.
"The CandyFab 6000"; Evil Mad Scientist Laboratories; bearing a date of 2011; 7 pages; Evil Mad Scientist Laboratories.
"Welcome to The CandyFabProject"; CandyFab.org; Jan. 22, 2011; 3 pages; The CandyFab Project.

(56) References Cited

OTHER PUBLICATIONS

"Scientests create 'inhalable' food?"; bearing a date of Aug. 29, 2012; snapshot taken Apr. 12, 2009; available at http://web.archive.org/web/20090412131937/http://chowhound.chow.com/topics/611174.

"Transdermal Nutrient Delivery System"; U.S. Army Soldier and Biological Chemical Command; snapshot taken Jul. 21, 2004; available at http://webarchive.org/web/20040721134210 http://archives.tproc.org/www.sbccom.army.mil/products/food/tdnds.pdf.

American Society of Hospital Pharmacists; "ASHP Technical Assistance Bulleting on Compounding Nonsterile Products in Pharmacies"; Am. J. Hosp. Pharm.; bearing a date of 1994, approved Apr. 27, 1994; pp. 73-79; vol. 51, No. 1441-8; American Society of Hospital Pharmacists, Inc.

"Airline Tickets and Airline Reservations from American Airlines"; AA.com; 1 page; retrieved from the internet wayback machine on Oct. 27, 2011; located at http://web.archieve.org/web.20101027131457/http://www.aa.com.

Williams, N.T.; "Medication administration through enteral feeding tubes"; Am J Health Syst Pharm.; bearing a date of Dec. 15, 2008; 2 pages (abstract only); vol. 65, No. 24; located at http://www:ncbi.nlm.nih.gov/pubmed/19052281.

McDonald's; sample restaurant menu (as provided by examiner); Feb. 10, 2014; 1 page; located at: http://www.burgerbusiness.com/wp-content/uploads/McD_Calor . . . .

Indiana State Excise Police; "Alcohol Laws"; snapshot taken Oct. 22, 2010; pp. 1-2; located at http://web.archive.org/web/20101122202431/http://www.in.gov/atc/isep/2384.htm.

Valuevapor.com; "Starter Kits"; printed on Sep. 22, 2014; pp. 1-2; located at http://web.archive.org/web/20100610083606/http://www.valuevapor.com/VV/store/in.dex.php?main_page=index&cPath=10.

"Easy Delft Blue Eggs"; The Sweet Adventures of Sugarbelle Blog; Mar. 25, 2012; pp. 1-7; located at: www.sweetsugarbelle.com/2012/03/simple-delft-blue-easter-egg-cookies (best copy available) (as provided by examiner).

Fiore et al; "Effects of Imagery Copy and Product Samples on Responses Toward the Product"; Journal of Interactive Marketing; bearing a date of Spring 2001; pp. 36-46; vol. 15, No. 2.

Connors et al.; "Using a Visual Plate Waste Study to Monitor Menu Performance"; Journal of the American Dietetic Association; 2004, created on Oct. 18, 2016; pp. 94-96; vol. 104; American Dietetic Association.

McDonagh-Philp, Deana; "Using Focus Groups to Support New Product Development"; Institution of Engineering Designers Journal; Sep. 2000; pp. 1-6.

Shimmura et al.; "Analysis of Eating Behavior in Restaurants Based on Leftover Food"; 2010; pp. 956-960; IEEE.

"Toddlers at the Table: Avoiding Power Struggles," located at https://web.archive.org/web/20100121730406/http://kidshealth.org/parent/nutrition_center/staying_fit/toddler_meals.html; KidsHealth; 2010; pp. 1-2; The Nemours Foundation.

Poulter, Sean; "Medicine vending machines that dispense prescriptions 24 hours a day go on trial"; bearing a date of Jun. 22, 2010; created on Nov. 27, 2017; pp. 1-5; located at http://www.dailymail.co.uk/health/article-1288434/Medicine-vending-machine-dispenses-prescriptions-pharmacist-launched.html.

\* cited by examiner

REPORTING SYSTEM AND METHOD FOR INGESTIBLE PRODUCT PREPARATION SYSTEM AND METHOD

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/199,361, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 26 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,481, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 30 Aug. 2011 now U.S. Pat. No. 9,600,850, which is an application of which a currently co-pending application is entitled to the benefit of the filing date.

For purposes of the USPTO extra-statutory requirements, the present application constitutes a continuation of U.S. patent application Ser. No. 13/199,545, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011 now U.S. Pat. No. 9,240,028, which is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A method includes, but is not limited to electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information; and electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being.

In one or more various aspects, related machines, compositions of matter, or manufactures of systems may include, but are not limited to, virtually any combination of hardware, software, and/or firmware (the virtually any combination being limited to patentable subject matter under 35 U.S.C. 101) configured to effect the herein-referenced method aspects depending upon the design choices of the system designer.

A system includes, but is not limited to: means for electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information; and means for electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being. In addition to the foregoing, other system aspects are described in the claims, drawings, and text forming a part of the present disclosure.

A system includes, but is not limited to a receiving directive information electrical circuitry arrangement for electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information; and a transmitting occurrence info electrical circuitry arrangement for electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being. In addition to the foregoing, other system aspects are described in the claims, drawings, and text forming a part of the present disclosure.

An article of manufacture including a non-transitory signal-bearing storage medium bearing one or more instructions for electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information; and one or more instructions for electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
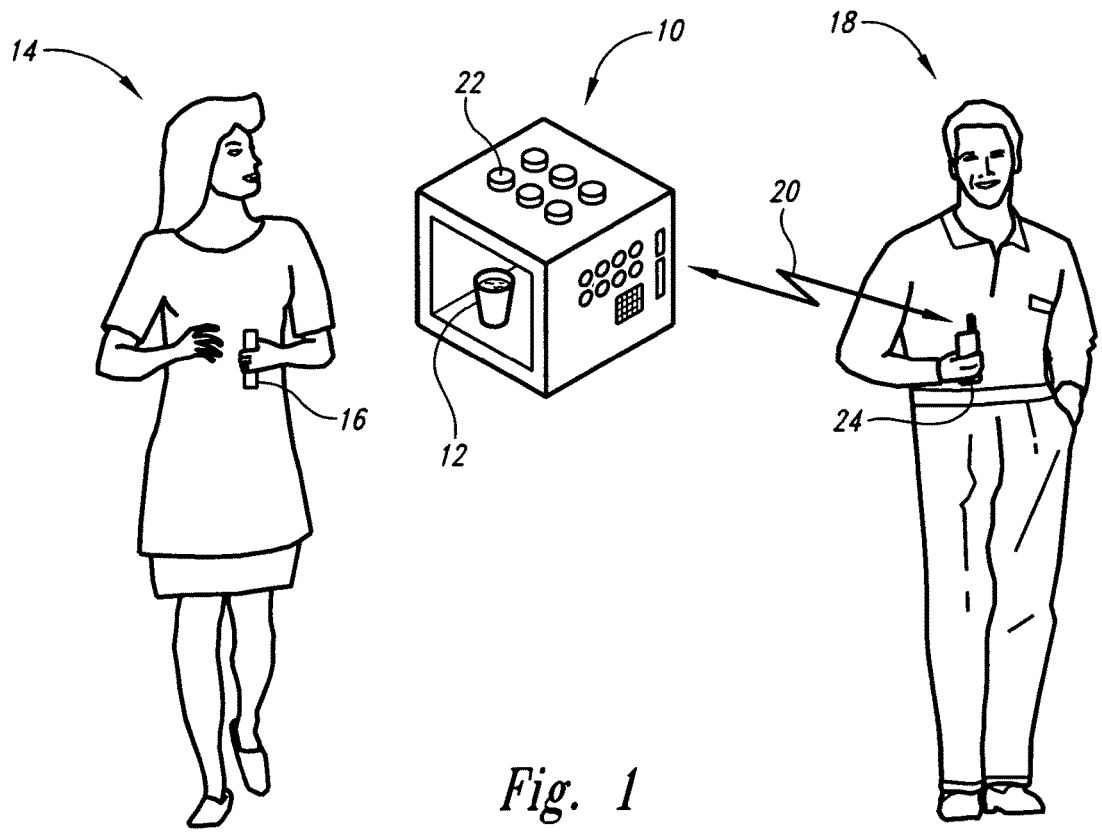
FIG. 1 is a schematic diagram depicting a first exemplary implementation of an ingestible product reporting system 10.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare ingestible products to be ingested by living beings such as humans, animals, plants, etc are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Ingestion by the living beings can occur through many pathways including, but not limited to, oral ingestion, transdermal ingestion, peg-tube ingestion, anal ingestion, injectable ingestion, tear-duct ingestion, and respiratory ingestion.

Figure 2:
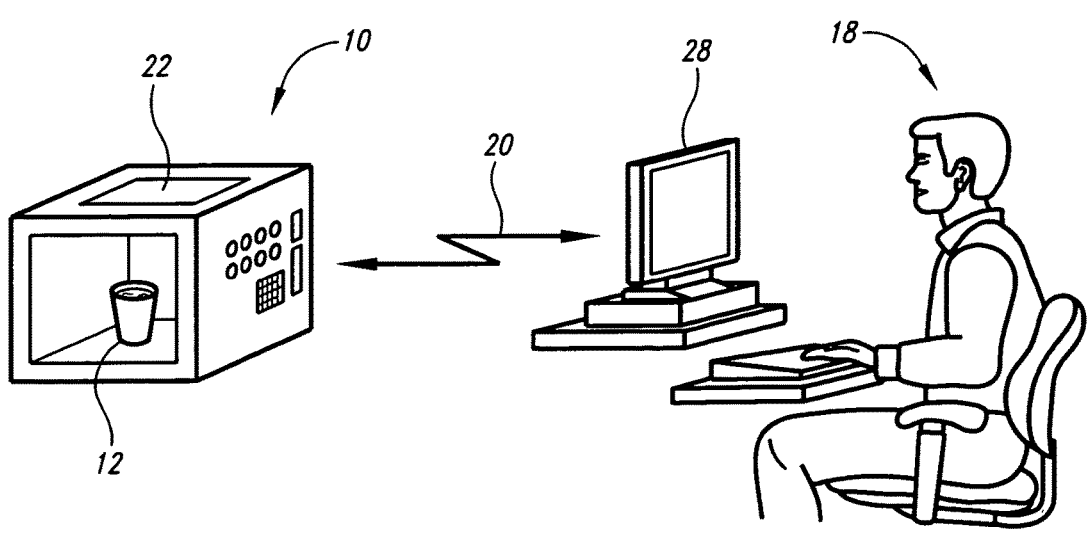
FIG. 2 is a schematic diagram depicting a second exemplary implementation of the ingestible product reporting system 10 of FIG. 1.

As depicted in FIG. 1, an exemplary implementation of an ingestible product reporting system 10 is shown to prepare ingestible products such as a liquid drink 12 as shown to be consumed by a particular individual living being, such as a human being 14 shown. Methods, systems, and articles of manufacture in accordance with various implementations of the ingestible product reporting system 10 are disclosed herein and are further discussed below. Another ingestible product is shown as a food bar 16 being held by the living being to be consumed thereby. An authority, such as a physician 18 shown, can send directive information 20 to the ingestible product reporting system 10 via a mobile device 24, such as a cell phone or other such communication device, such as a computer workstation 26 depicted in FIG. 2. The mobile device 24, the workstation 26 or other communication device can also be used by authorities to receive reporting information regarding occurrences of preparation of various ingestible products for the living being. In other implementations authorities can include but are not limited to pharmacists, nutritionists, health care centers, hospitals, fitness centers, other health care providers, etc. Generally, the authority is authorized in some fashion to be involved with the authorship and/or distribution control of the directive information 20. The directive information 20 includes verification information to allow verification for the ingestible product reporting system 10 that issuance of the directive information, such as involving authorship and/or distribution control of the directive information involved the authority. The directive information 20 also includes living being identification associated with a particular individual living being to be the recipient of one or more ingestible products to be prepared by the ingestible product reporting system 10 according to at least in part the directive information. The directive information 20 further includes reporting directions designated by the authority as associated with the particular individual living being. The reporting directions direct the ingestible product reporting system 10 to electronically record and transmit occurrence information concerning instances of preparation of ingestible product optionally associated with a controlled substance for one or more particular individual livings being so designated by the reporting directions.

The ingestible product can also be designated through controlled substance information for involvement with at least one designated controlled substance, such as shown in containers 22, designated to be used by the particular individual living being according to at least one requirement designated as being associated with the particular individual living being. Involvement of the controlled substance with the ingestible product can include, but is not limited to, being incorporated into the ingestible product as one or more ingredients or otherwise one or more components of the ingestible product. Other cases of controlled substance involvement with the ingestible product includes using the ingestible product as a carrier of the controlled substance or providing the ingestible product to be consumed alongside, concurrently, or at a designated time other than the time that ingestion of the controlled substance is designated to occur.

Figure 5:
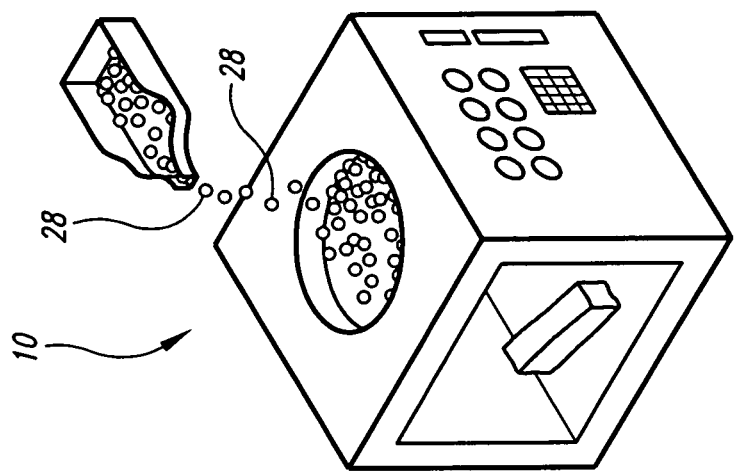
FIG. 5 is a schematic diagram depicting a third exemplary implementation of dispensing controlled substances for the ingestible product reporting system 10 of FIG. 1.
Figure 4:
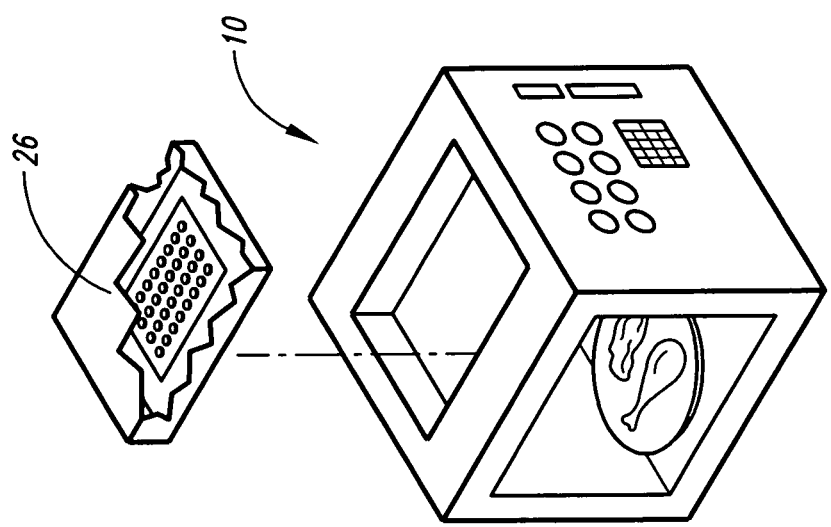
FIG. 4 is a schematic diagram depicting a second exemplary implementation of dispensing controlled substances for the ingestible product reporting system 10 of FIG. 1.
Figure 3:
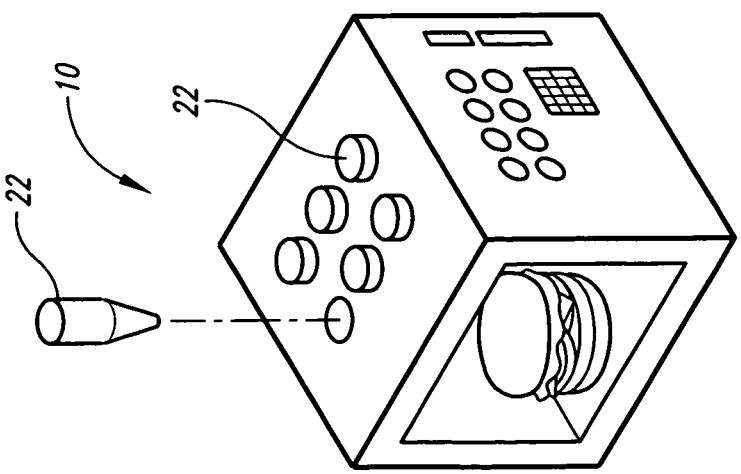
FIG. 3 is a schematic diagram depicting a first exemplary implementation of dispensing controlled substances for the ingestible product reporting system 10 of FIG. 1.

Some examples of ingestible product preparation are depicted by exemplary implementations shown in FIGS. 3-5 of the ingestible product reporting system 10. Such examples include sandwich making, shown in FIG. 3, meal making, shown in FIG. 4, and food bar making, shown in FIG. 5. In addition to the containers 22 depicted in FIG. 3, other depicted storage includes trays of individually housed portions 28 depicted in FIG. 4, and tablets 30 being individually administered as depicted in FIG. 5.

Figure 6:
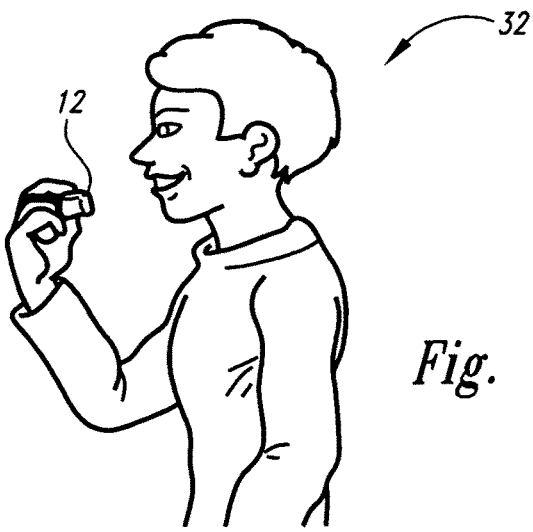
FIG. 6 is an illustration depicting a particular individual living being as a subject of the ingestible product reporting system 10 of FIG. 1.
Figure 7:
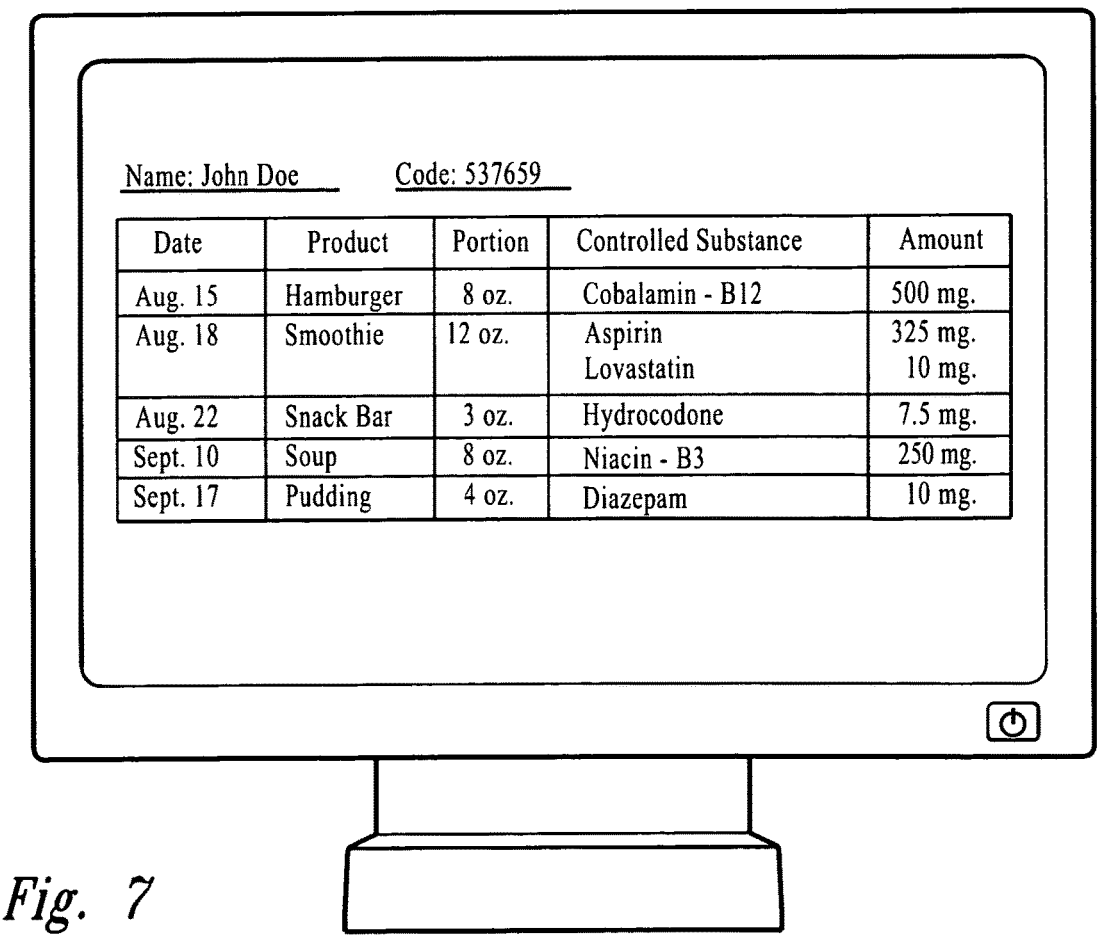
FIG. 7 is an illustration depicting an exemplary electronic device having received a report from the ingestible product reporting system 10 of FIG. 1.

As depicted in FIG. 6, a woman 32, as the living being, is ingesting the snack bar 16 as prepared by the ingestible product reporting system 10. This preparation is reported to the computer workstation 28 as August $22^{nd}$ entry shown in FIG. 7 in which the snack bar 16 was prepared to contain 7.5 mg of hydrocodone as a controlled substance.

Figure 8:
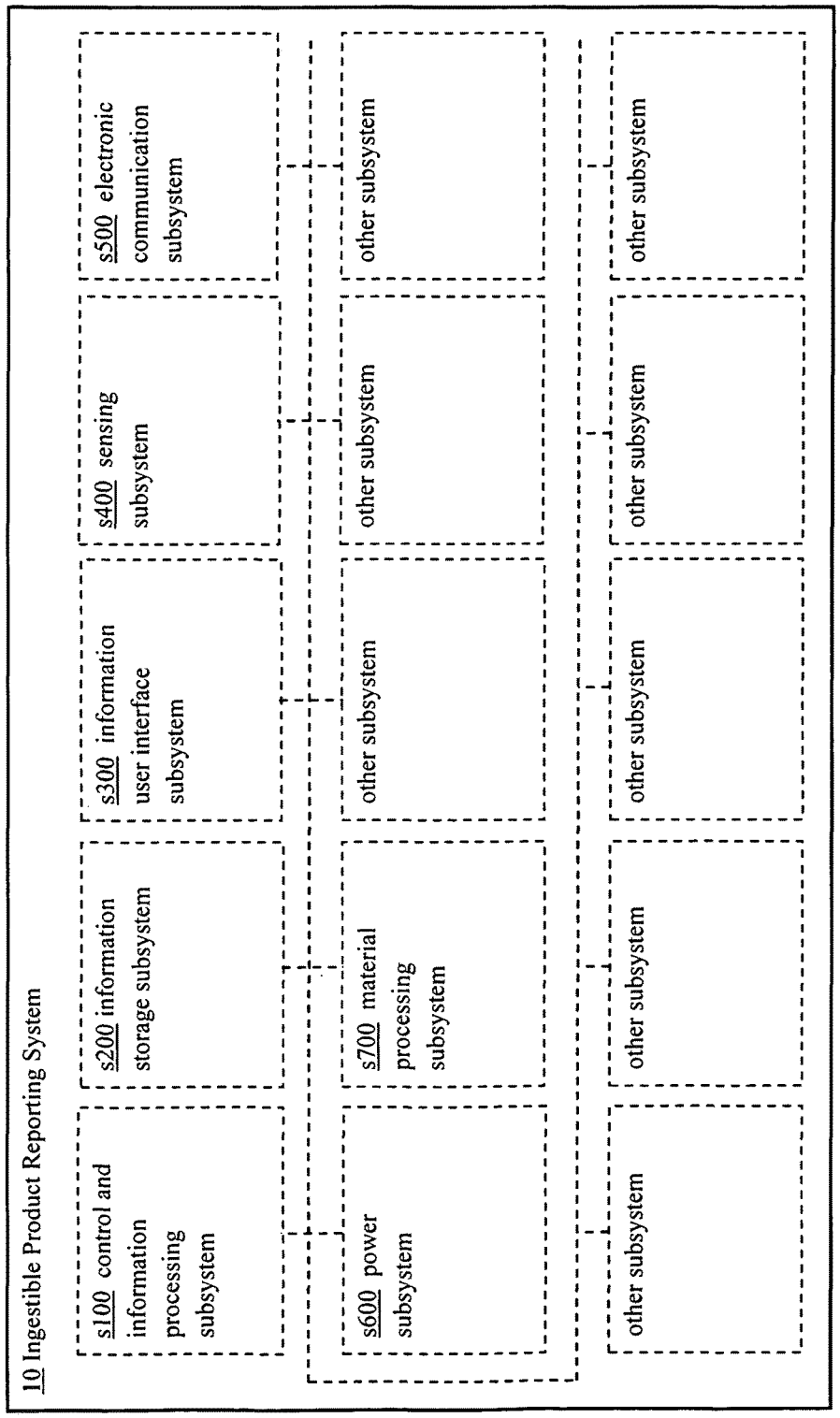
FIG. 8 is a block diagram depicting an exemplary implementation of the ingestible product reporting system 10 including exemplary subsystems of FIG. 1.

An exemplary version of the ingestible product reporting system 10 is shown in FIG. 8 to optionally include various subsystems such as control and information processing subsystem s100, information storage subsystem s200, information user interface subsystem s300, sensing subsystem s400, electronic communication subsystem s500, power subsystem s600, and material processing subsystem s700.

Figure 9:
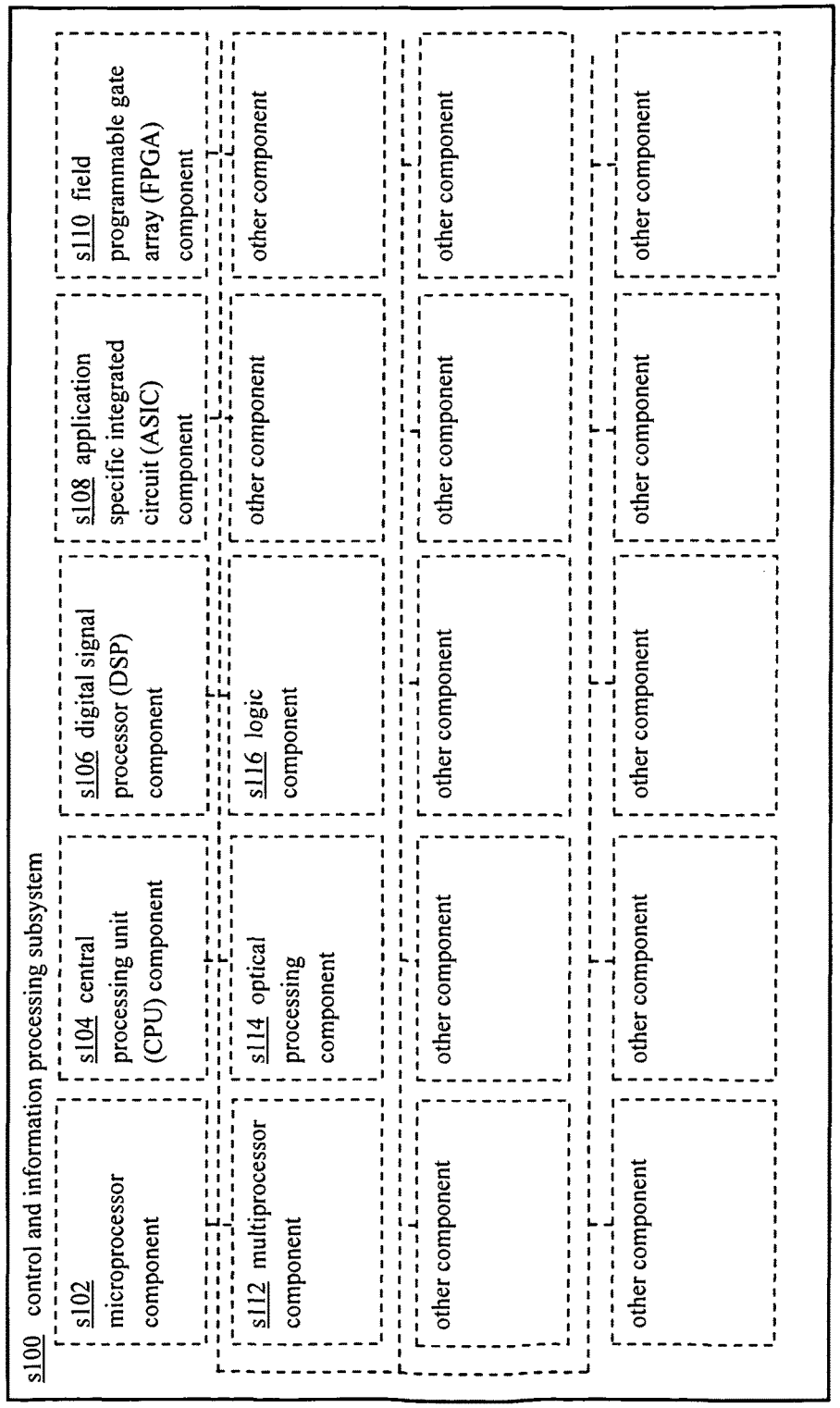
FIG. 9 is a block diagram depicting a control and information processing subsystem s100 of an exemplary implementation of the ingestible product reporting system 10 of FIG. 1.

An exemplary implementation of the control and information processing subsystem s100 is shown in FIG. 9 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, and optical processing component s114.

Figure 10:
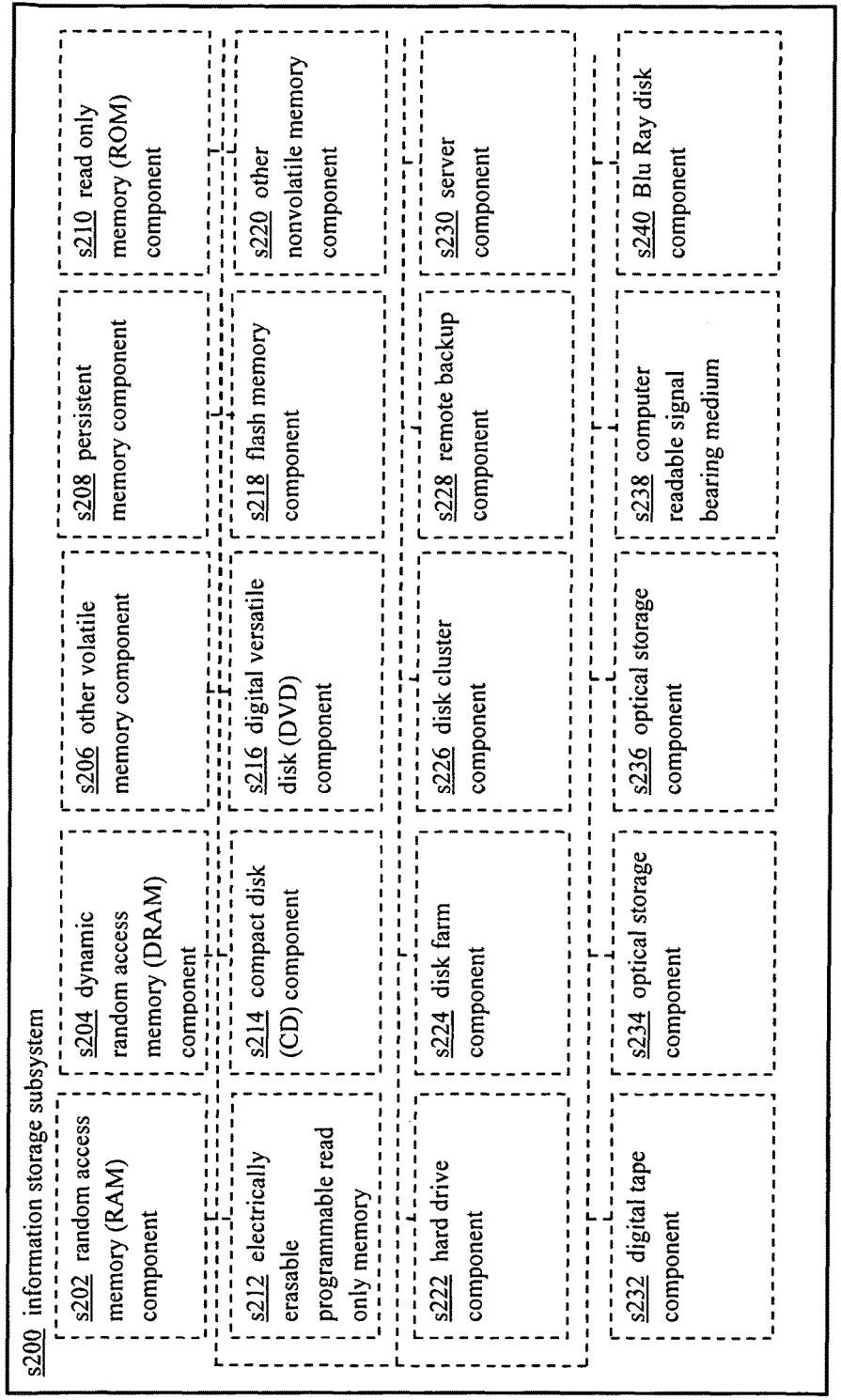
FIG. 10 is a block diagram depicting an information storage subsystem s200 of an exemplary implementation of the ingestible product reporting system 10 of FIG. 1.

An exemplary implementation of the information storage subsystem s200 is shown in FIG. 10 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, optical storage component s236, computer readable signal bearing medium s238, and Blu Ray disk component s240.

Figure 11:
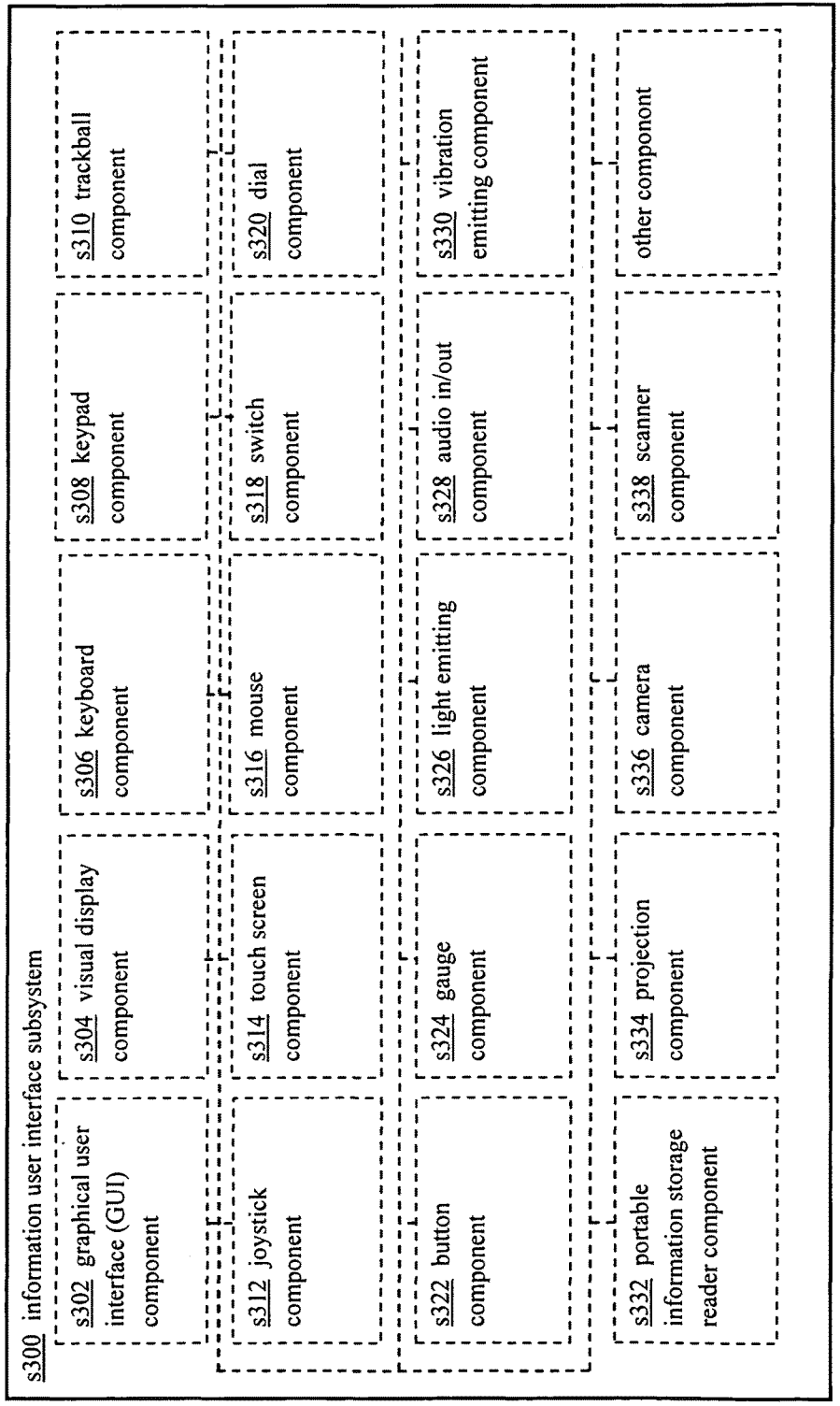
FIG. 11 is a block diagram depicting an information user interface subsystem s300 of an exemplary implementation of the ingestible product reporting system 10 of FIG. 1.

An exemplary implementation of the information user interface subsystem s300 is shown in FIG. 11 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, projection component s334, camera component s336, and scanner component s338.

Figure 12:
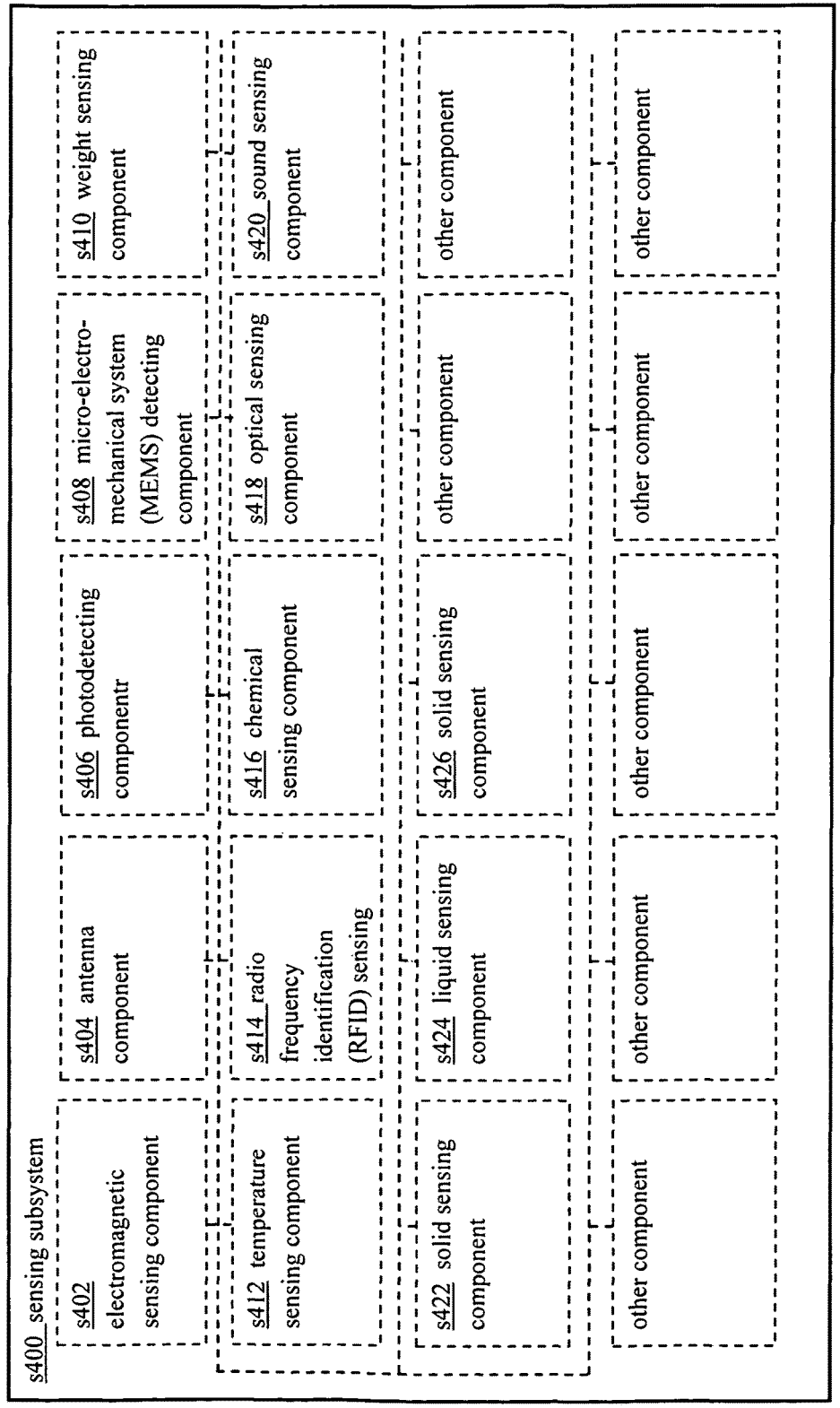
FIG. 12 is a block diagram depicting a sensing subsystem s400 of an exemplary implementation of the ingestible product reporting system 10 of FIG. 1.

An exemplary implementation of the sensing subsystem s400 is shown in FIG. 12 to optionally include various components such as electromagnetic sensing component s402, antenna component s404, photodetecting component s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 13:
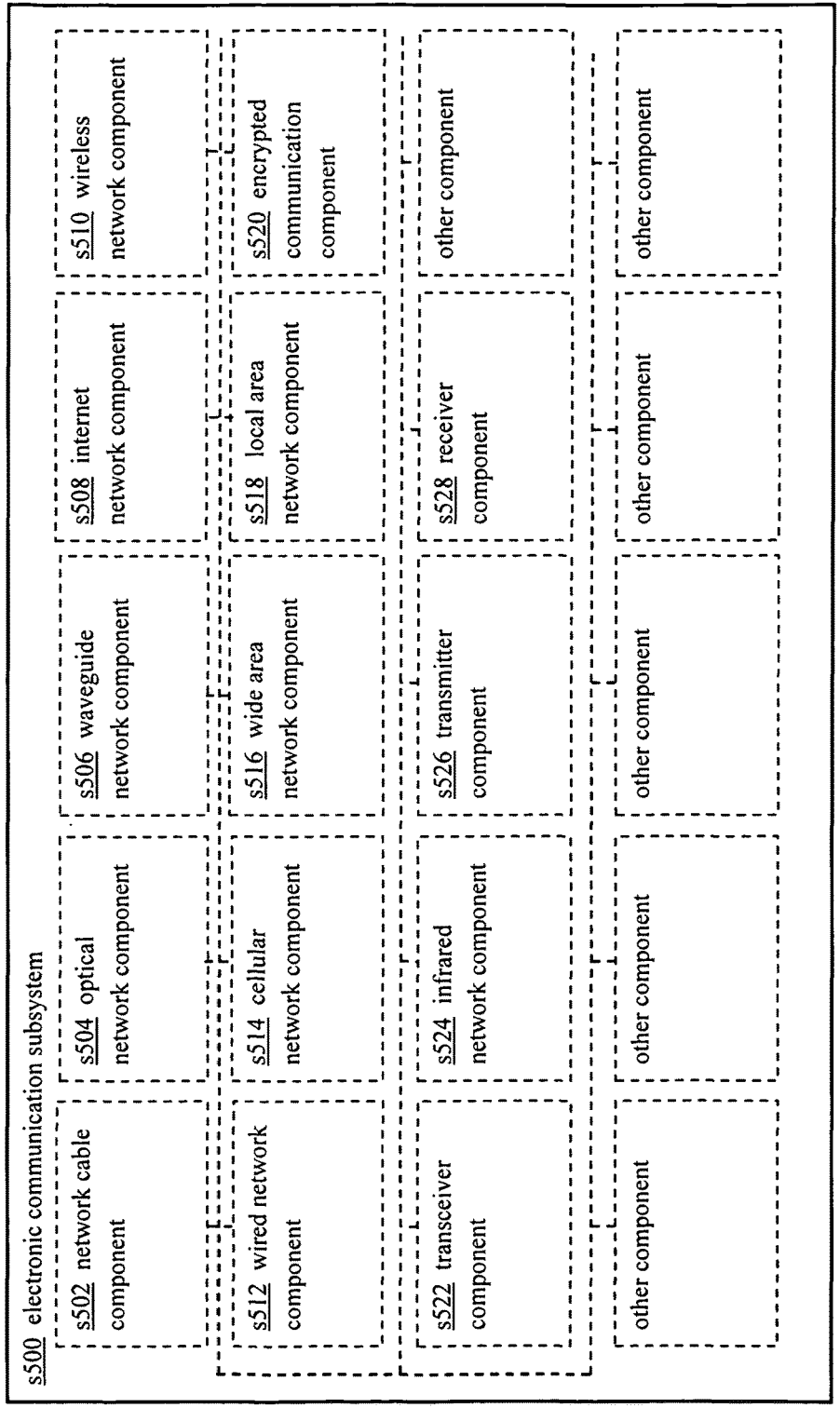
FIG. 13 is a block diagram depicting an electronic communication subsystem s500 of an exemplary implementation of the ingestible product reporting system 10 of FIG. 1.

An exemplary implementation of the electronic communication subsystem s500 is shown in FIG. 13 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 14:
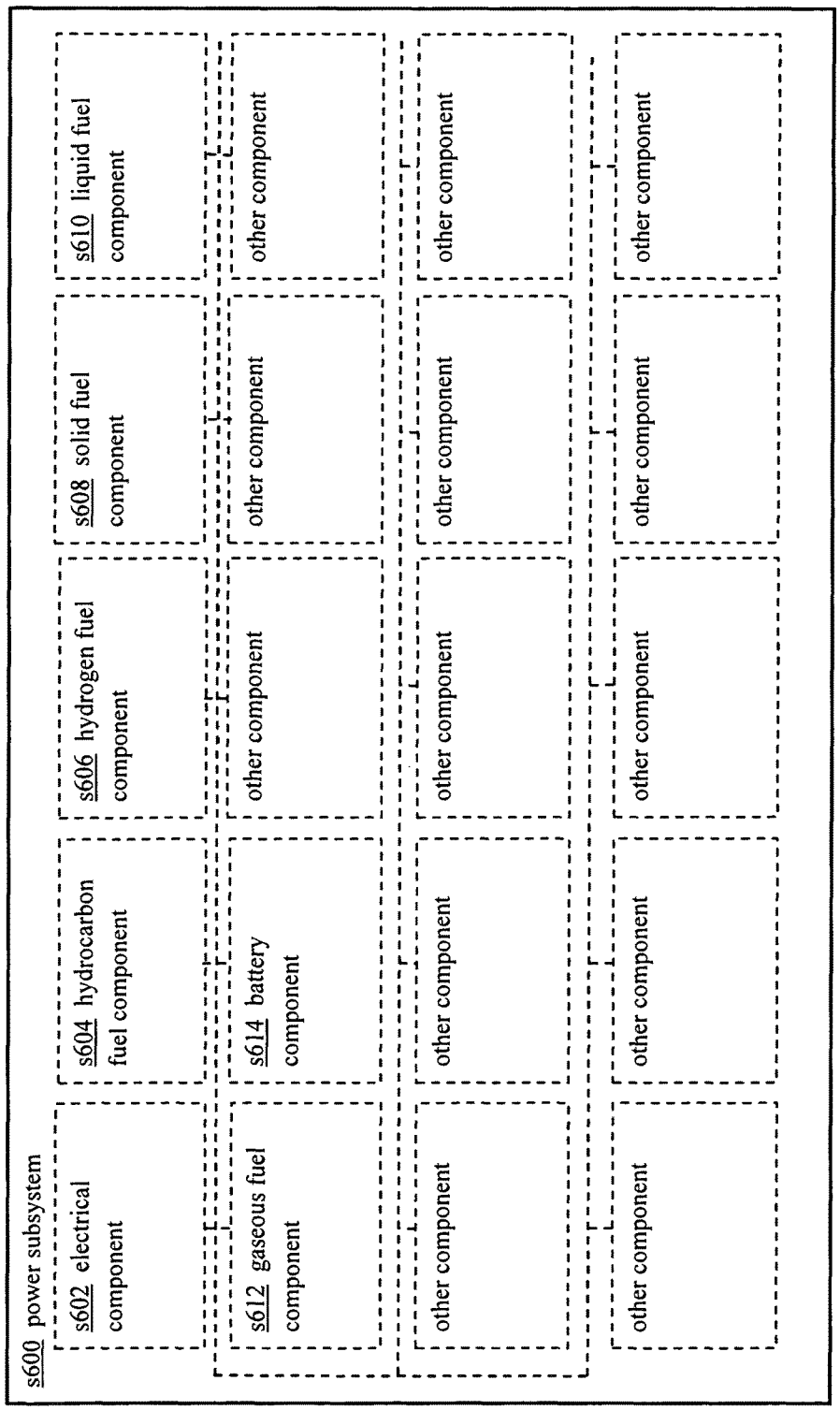
FIG. 14 is a block diagram depicting a power subsystem s600 of an exemplary implementation of the ingestible product reporting system 10 of FIG. 1.

An exemplary implementation of the power subsystem s600 is shown in FIG. 14 to optionally include various components such as electrical component s602, hydrocarbon fuel component s604, hydrogen fuel component s606, solid fuel component s608, liquid fuel component s610, gaseous fuel component s612, and battery component s614.

Figure 15:
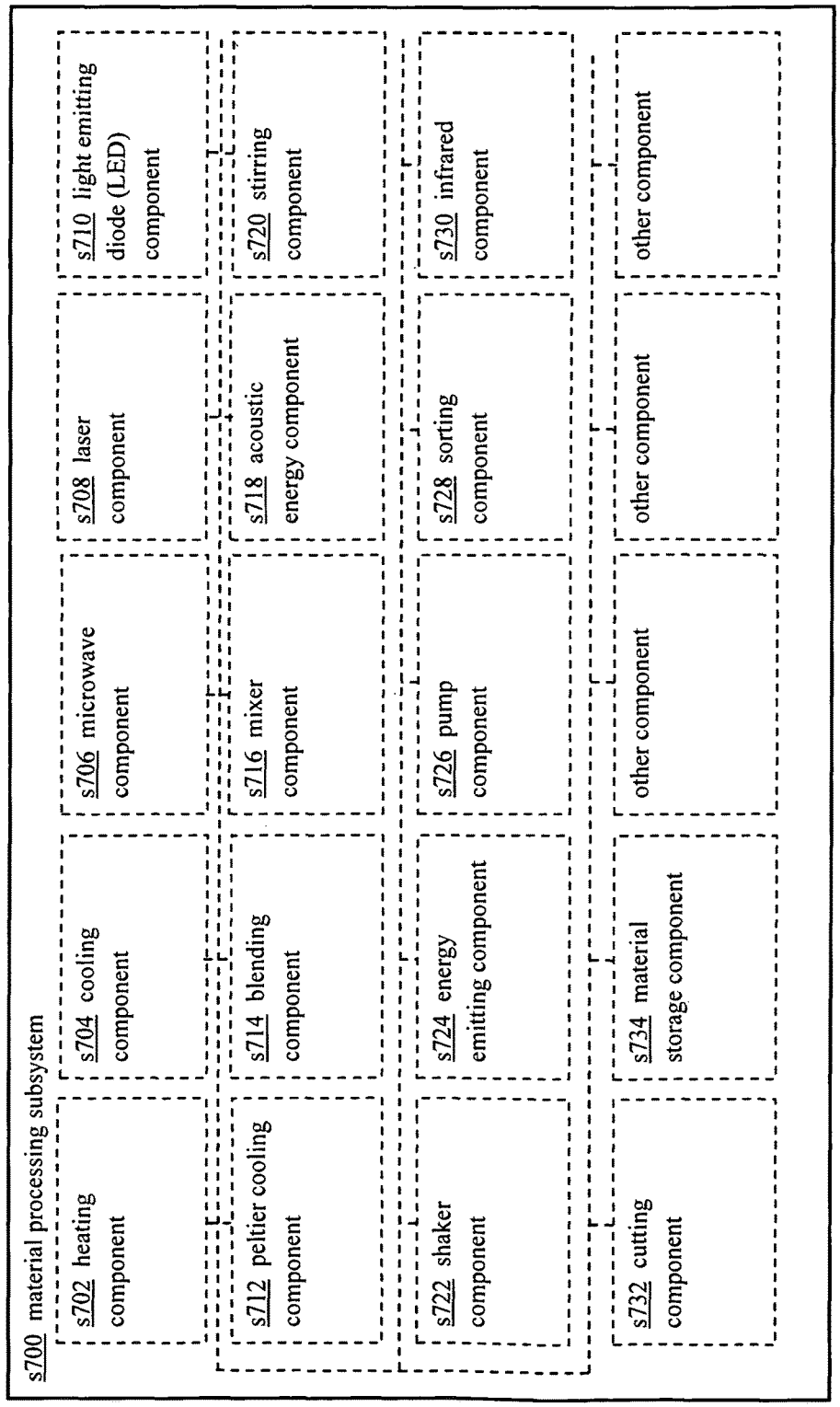
FIG. 15 is a block diagram depicting a material processing subsystem s700 of an exemplary implementation of the ingestible product reporting system 10 of FIG. 1.

An exemplary implementation of the material processing subsystem s700 is shown in FIG. 15 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, and material storage component s734.

Figure 16:
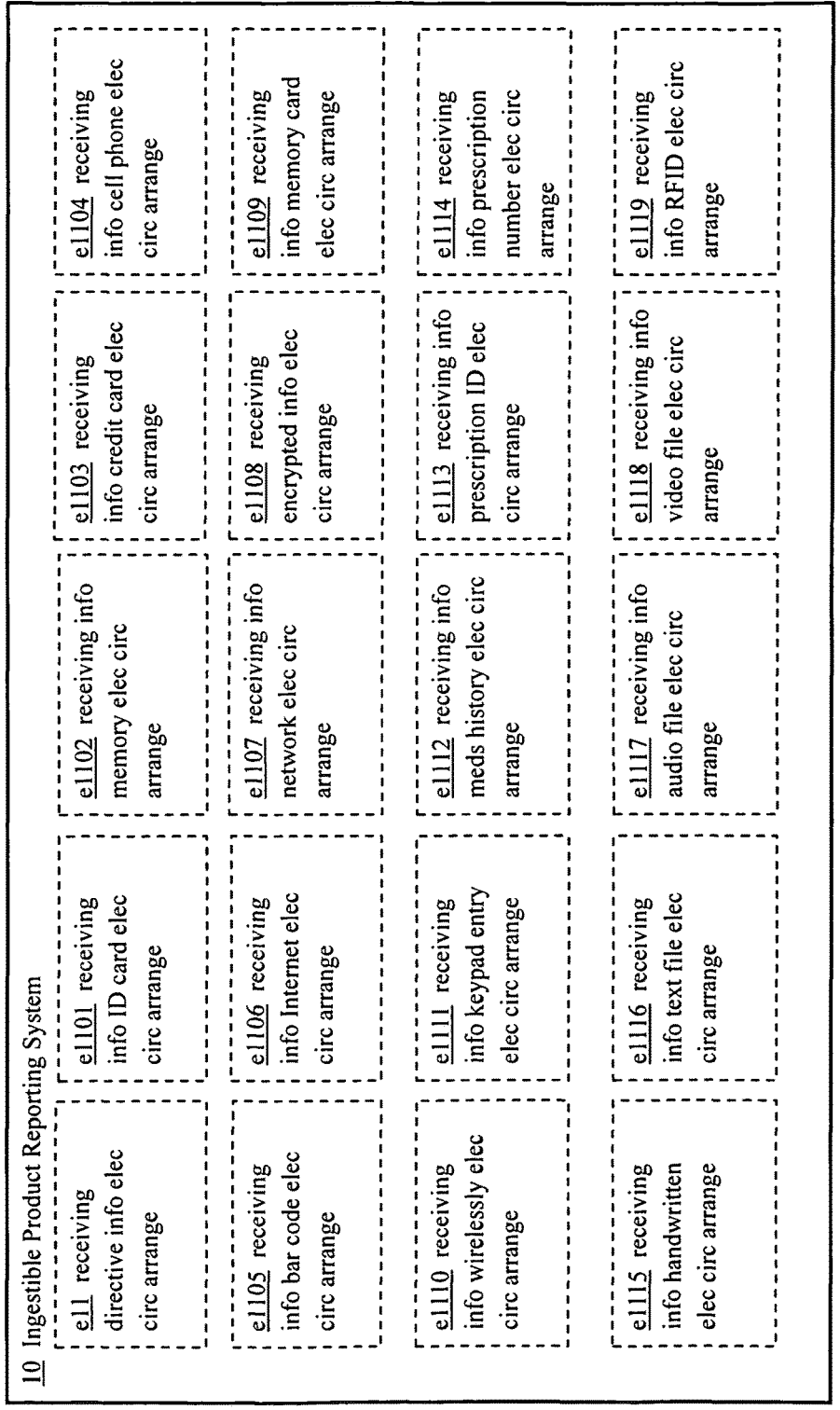
FIG. 16 is a block diagram depicting one or more exemplary electrical circuitry arrangements of the ingestible product reporting system 10 of FIG. 1.

Implementations involve different combinations (otherwise known as "electrical circuitry arrangements") of components from the subsystems of the ingestible product reporting system 10. Exemplary depictions of some of these electrical circuitry arrangements are shown in FIG. 16 to include receiving directive information electrical circuitry arrangement e11, receiving information ID card electrical circuitry arrangement e1101, receiving information memory electrical circuitry arrangement e1102, receiving information credit card electrical circuitry arrangement e1103, receiving information cell phone electrical circuitry arrangement e1104, receiving information bar code electrical circuitry arrangement e1105, receiving information Internet electrical circuitry arrangement e1106, receiving information network electrical circuitry arrangement e1107, receiving encrypted information electrical circuitry arrangement e1108, receiving information memory card electrical circuitry arrangement e1109, receiving information wirelessly electrical circuitry arrangement e1110, receiving information keypad entry electrical circuitry arrangement e1111, receiving information meds history electrical circuitry arrangement e1112, receiving information prescription ID electrical circuitry arrangement e1113, receiving information prescription number electrical circuitry arrangement e1114, receiving information handwritten electrical circuitry arrangement e1115, receiving information text file electrical circuitry arrangement e1116, receiving information audio file electrical circuitry arrangement e1117, receiving information video file electrical circuitry arrangement e1118, and receiving information RFID electrical circuitry arrangement e1119.

Figure 17:
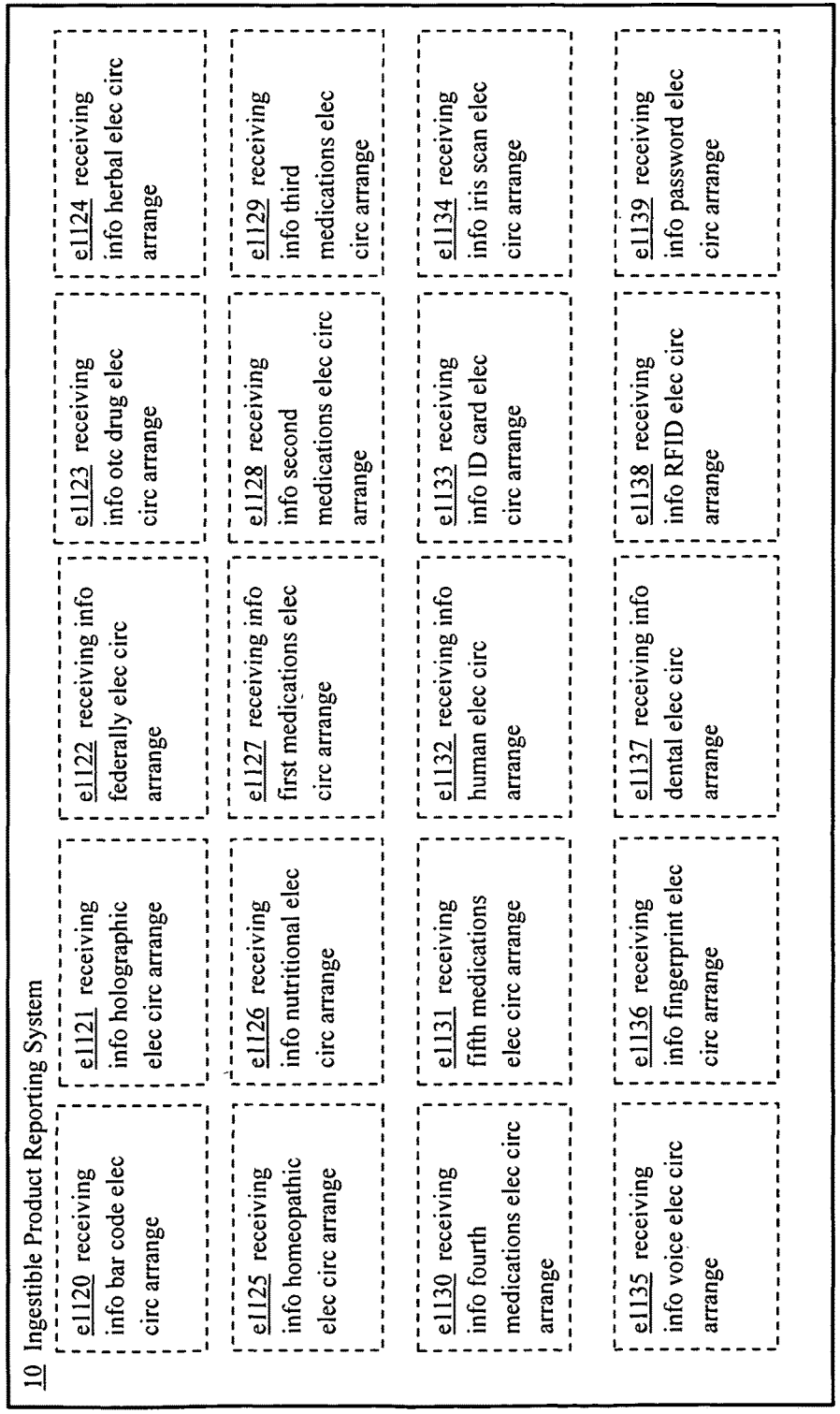
FIG. 17 is a block diagram depicting one or more exemplary electrical circuitry arrangements of the ingestible product reporting system 10 of FIG. 1.

Some of these electrical circuitry arrangements are depicted in FIG. 17 to include receiving information bar code electrical circuitry arrangement e1120, receiving information holographic electrical circuitry arrangement e1121, receiving information federally electrical circuitry arrangement e1122, receiving information otc drug electrical circuitry arrangement e1123, receiving information herbal electrical circuitry arrangement e1124, receiving information homeopathic electrical circuitry arrangement e1125, receiving information nutritional electrical circuitry arrangement e1126, receiving information first medications electrical circuitry arrangement e1127, receiving information second medications electrical circuitry arrangement e1128, receiving information third medications electrical circuitry arrangement e1129, receiving information fourth medications electrical circuitry arrangement e1130, receiving fifth medications electrical circuitry arrangement e113, receiving information human electrical circuitry arrangement e1132, receiving information ID card electrical circuitry arrangement e1133, receiving information iris scan electrical circuitry arrangement e1134, receiving information voice electrical circuitry arrangement e1135, receiving information fingerprint electrical circuitry arrangement e1136, receiving information dental electrical circuitry arrangement e1137, receiving information RFID electrical circuitry arrangement e1138, and receiving information password electrical circuitry arrangement e1139.

Figure 18:
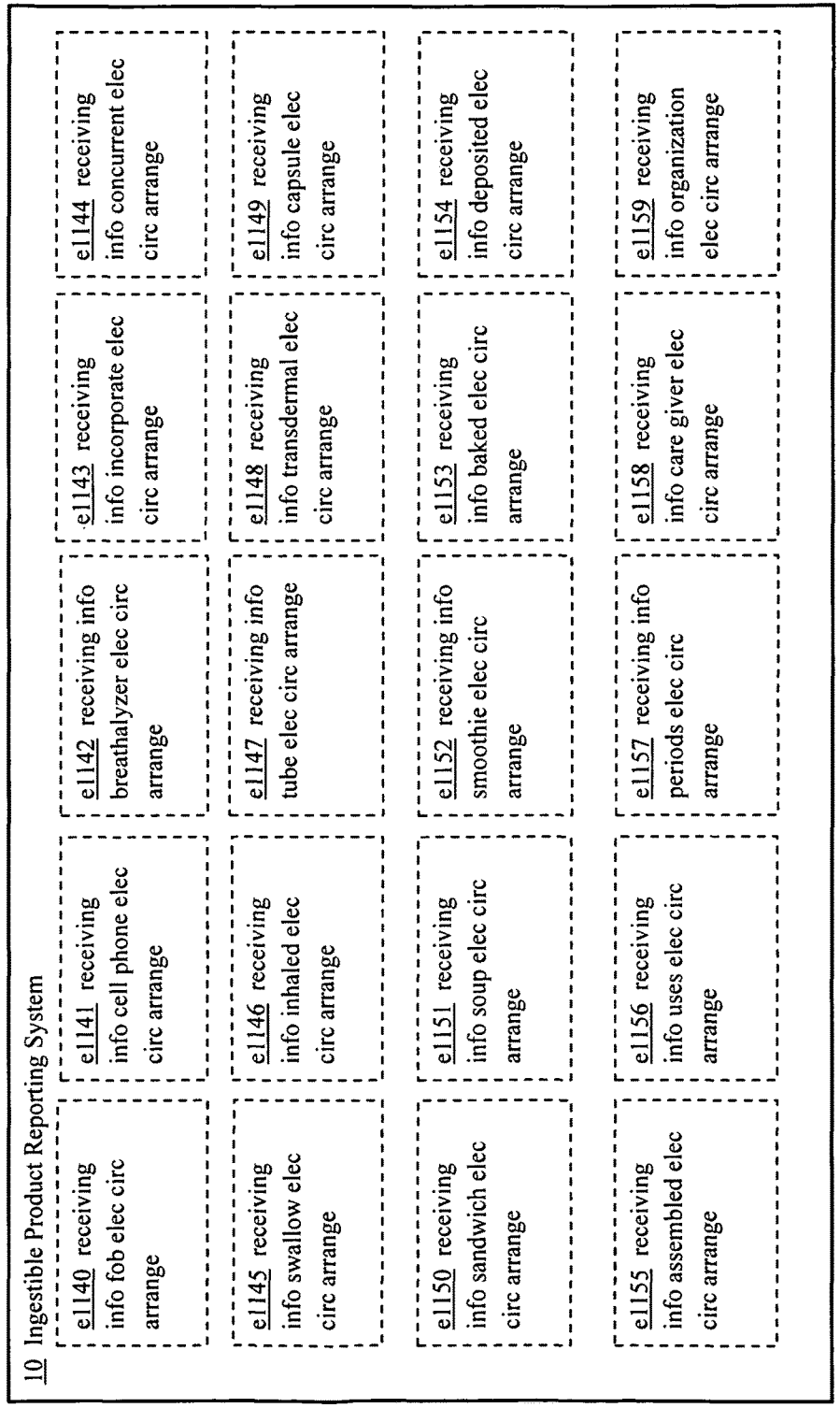
FIG. 18 is a block diagram depicting one or more exemplary electrical circuitry arrangements of the ingestible product reporting system 10 of FIG. 1.

Some of these electrical circuitry arrangements are depicted in FIG. 18 to include receiving information fob electrical circuitry arrangement e1140, receiving information cell phone electrical circuitry arrangement e1141, receiving information breathalyzer electrical circuitry arrangement e1142, receiving information incorporate electrical circuitry arrangement e1143, receiving information concurrent electrical circuitry arrangement e1144, receiving information swallow electrical circuitry arrangement e1145, receiving information inhaled electrical circuitry arrangement e1146, receiving information tube electrical circuitry arrangement e1147, receiving information transdermal electrical circuitry arrangement e1148, receiving information capsule electrical circuitry arrangement e1149, receiving information sandwich electrical circuitry arrangement e1150, receiving information soup electrical circuitry arrangement e1151, receiving information smoothie electrical circuitry arrangement e1152, receiving information baked electrical circuitry arrangement e1153, receiving information deposited electrical circuitry arrangement e1154, receiving information assembled electrical circuitry arrangement a 1155, receiving information uses electrical circuitry arrangement e1156, receiving information periods electrical circuitry arrangement e1157, receiving information care giver electrical circuitry arrangement e1158, and receiving information organization electrical circuitry arrangement e1159.

Figure 19:
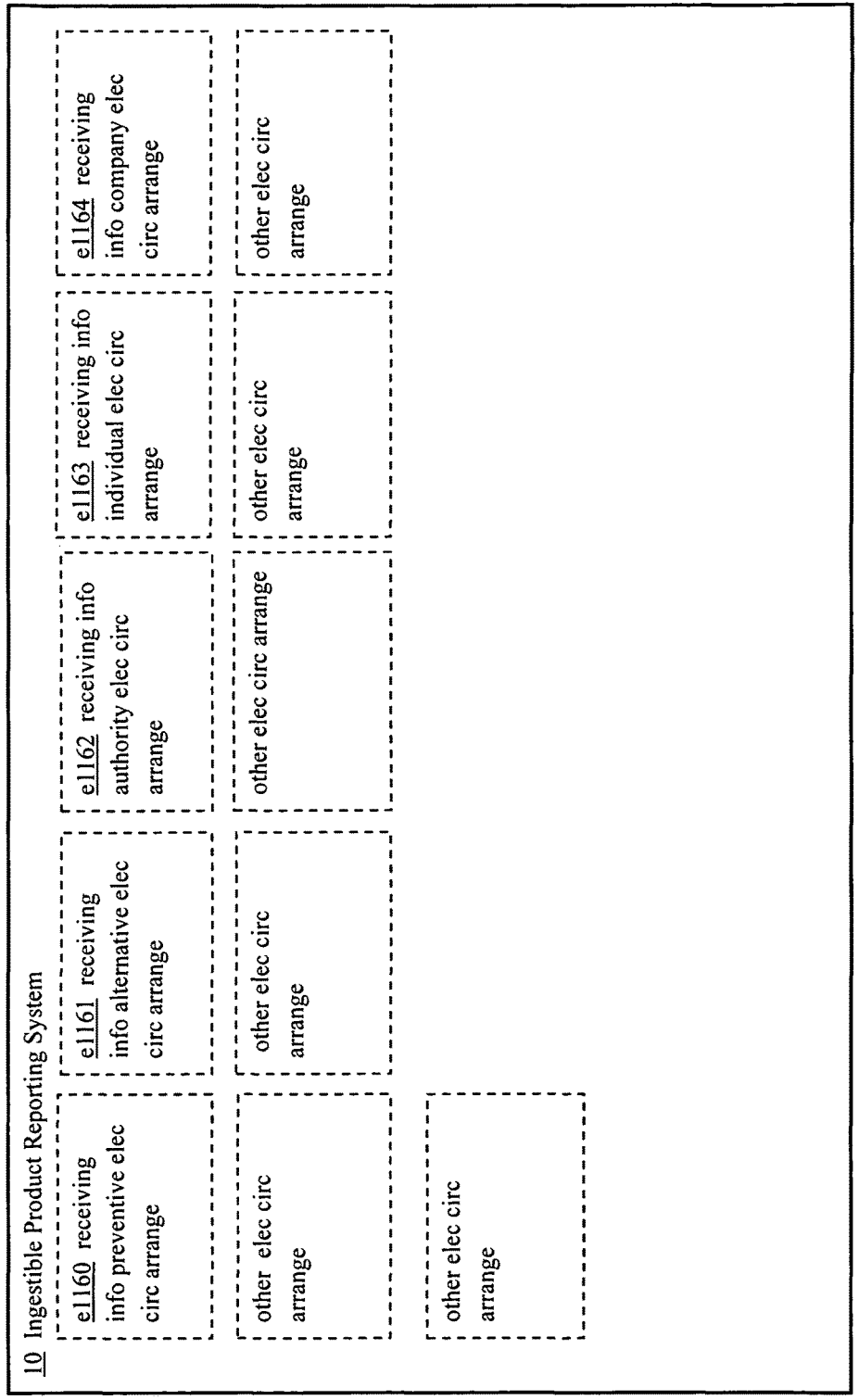
FIG. 19 is a block diagram depicting one or more exemplary electrical circuitry arrangements of the ingestible product reporting system 10 of FIG. 1.

Some of these electrical circuitry arrangements are depicted in FIG. 19 to include receiving information preventive electrical circuitry arrangement e1160, receiving information alternative electrical circuitry arrangement e1161, receiving information authority electrical circuitry arrangement e1162, receiving information individual electrical circuitry arrangement e1163, and receiving information company electrical circuitry arrangement e1164.

Figure 20:
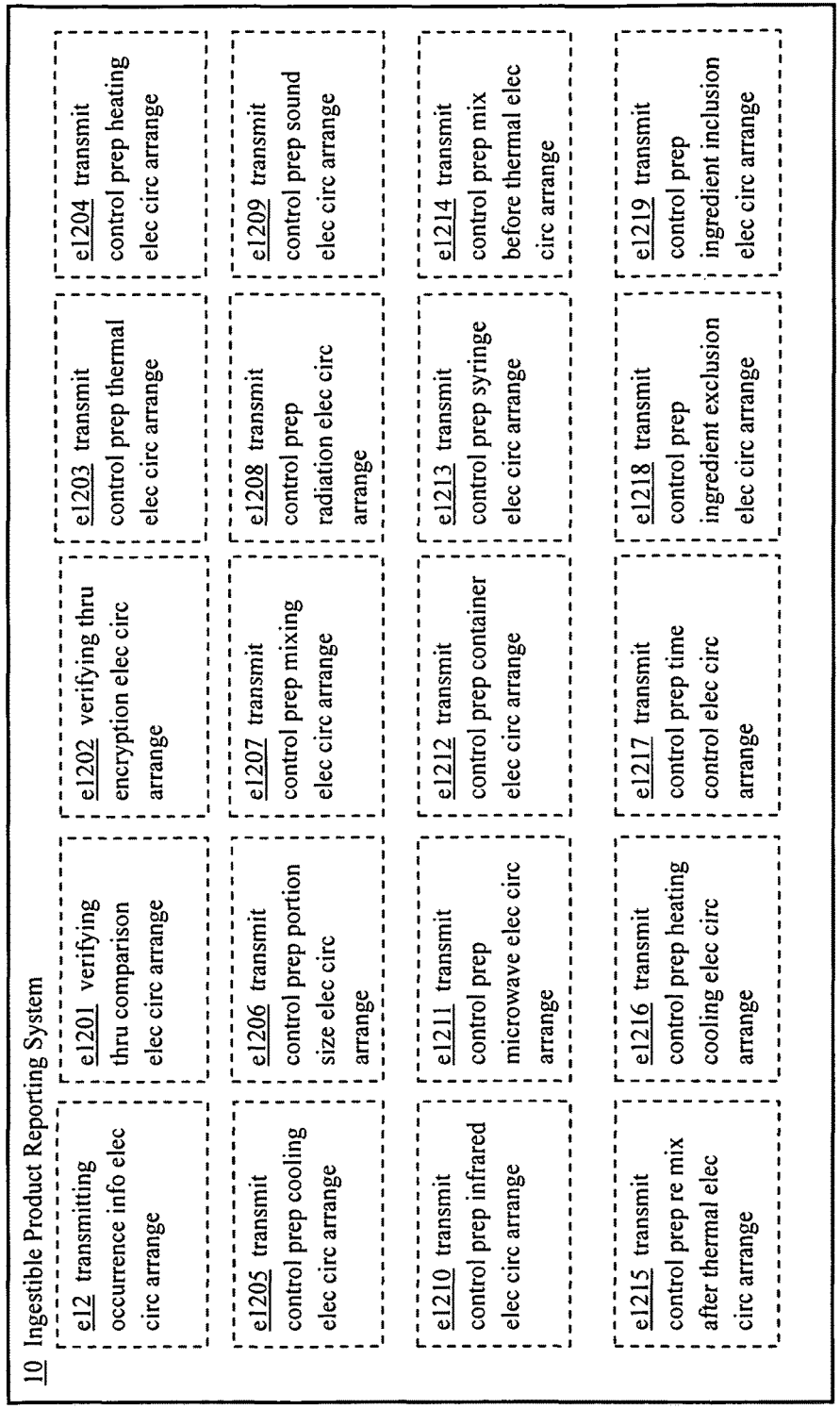
FIG. 20 is a block diagram depicting one or more exemplary electrical circuitry arrangements of the ingestible product reporting system 10 of FIG. 1.

Some of these electrical circuitry arrangements are depicted in FIG. 20 to include transmitting occurrence info electrical circuitry arrangement e12, verifying thru comparison electrical circuitry arrangement e1201, verifying thru encryption electrical circuitry arrangement e1202, transmit control prep thermal electrical circuitry arrangement e1203, transmit control prep heating electrical circuitry arrangement e1204, transmit control prep cooling electrical circuitry arrangement e1205, transmit control prep portion size electrical circuitry arrangement e1206, transmit control prep mixing electrical circuitry arrangement e1207, transmit control prep radiation electrical circuitry arrangement e1208, transmit control prep sound electrical circuitry arrangement e1209, transmit control prep infrared electrical circuitry arrangement e1210, transmit control prep microwave electrical circuitry arrangement e1211, transmit control prep container electrical circuitry arrangement e1212, transmit control prep syringe electrical circuitry arrangement e1213, transmit control prep mix before thermal electrical circuitry arrangement e1214, transmit control prep re mix after thermal electrical circuitry arrangement e1215, transmit control prep heating cooling electrical circuitry arrangement e1216, transmit control prep time control electrical circuitry arrangement e1217, transmit control prep ingredient exclusion electrical circuitry arrangement e1218, and transmit control prep ingredient inclusion electrical circuitry arrangement e1219.

Figure 21:
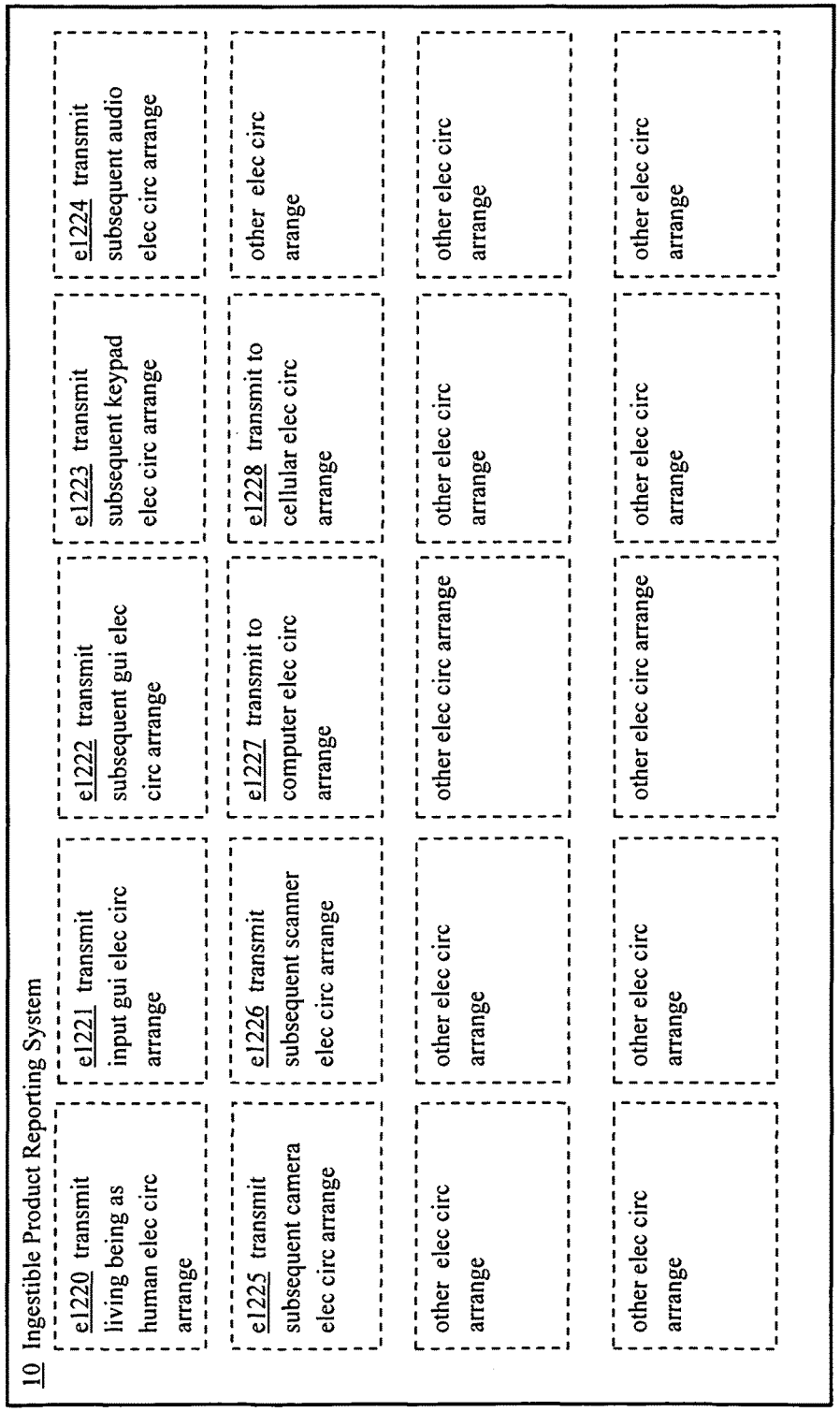
FIG. 21 is a block diagram depicting one or more exemplary electrical circuitry arrangements of the ingestible product reporting system 10 of FIG. 1.

Implementations involve different combinations (otherwise known as "electrical circuitry arrangements") of components from the subsystems of the ingestible product reporting system 10. Some of these electrical circuitry arrangements are depicted in FIG. 21 to include transmit living being as human electrical circuitry arrangement e1220, transmit input gui electrical circuitry arrangement e1221, transmit subsequent gui electrical circuitry arrangement e1222, transmit subsequent keypad electrical circuitry arrangement e1223, transmit subsequent audio electrical circuitry arrangement e1224, transmit subsequent camera electrical circuitry arrangement e1225, transmit subsequent scanner electrical circuitry arrangement e1226, transmit to computer electrical circuitry arrangement e1227, and transmit to cellular electrical circuitry arrangement e1228.

Figure 22:
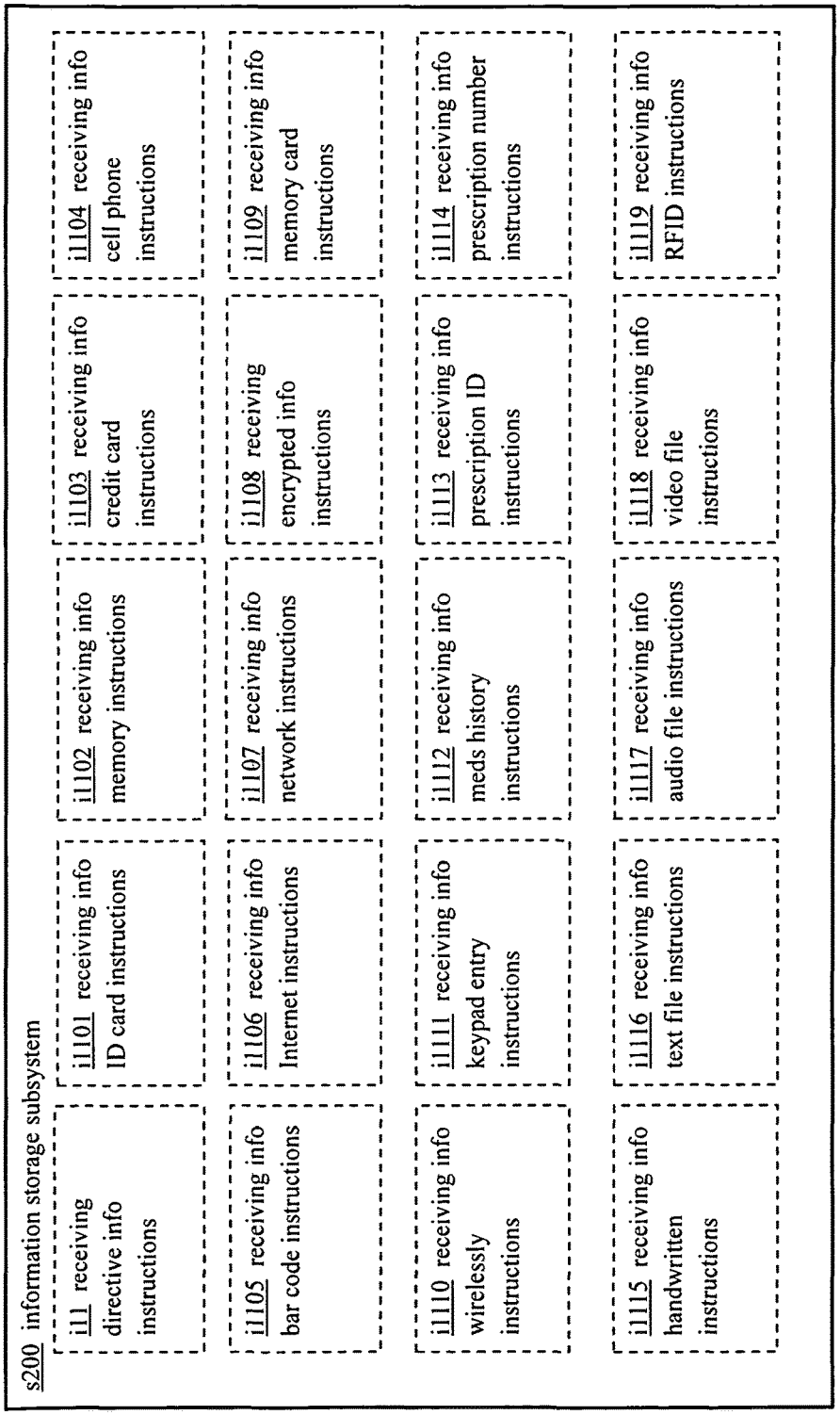
FIG. 22 is a block diagram depicting one or more exemplary instructions of the information storage subsystem s200 of the ingestible product reporting system 10 of FIG. 1.

In implementations one or more instructions are stored and/or otherwise borne in various subsystems, components, and/or accessories of the ingestible product reporting system 10 such as being borne in a non-transitory signal bearing medium n100. One or more exemplary instructions depicted in FIG. 22 as being borne in an exemplary version of the non-transitory signal bearing medium n100 include one or more receiving directive information instructions i11, one or more receiving information ID card instructions i1101, one or more receiving information memory instructions i1102, one or more receiving information credit card instructions i1103, one or more receiving information cell phone instructions i1104, one or more receiving information bar code instructions i1105, one or more receiving information Internet instructions i1106, one or more receiving information network instructions i1107, one or more receiving encrypted information instructions i1108, one or more receiving information memory card instructions i1109, one or more receiving information wirelessly instructions i1110, one or more receiving information keypad entry instructions i1111, one or more receiving information meds history instructions i1112, one or more receiving information prescription ID instructions i1113, one or more receiving information prescription number instructions i1114, one or more receiving information handwritten instructions i1115, one or more receiving information text file instructions i1116, one or more receiving information audio file instructions i1117, one or more receiving information video file instructions i1118, and one or more receiving information RFID instructions i1119.

Figure 23:
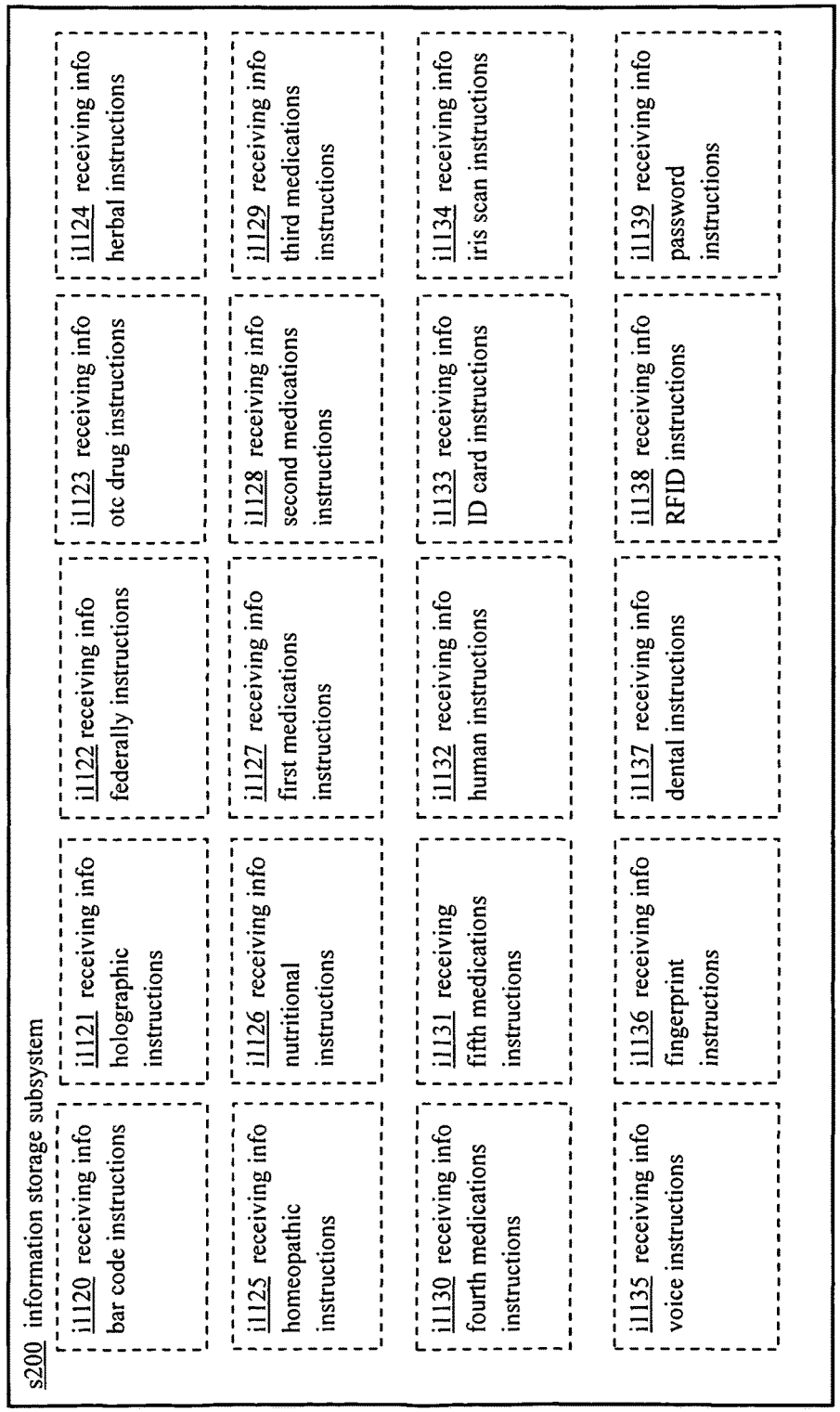
FIG. 23 is a block diagram depicting one or more exemplary instructions of the information storage subsystem s200 of the ingestible product reporting system 10 of FIG. 1.

One or more exemplary instructions depicted in FIG. 23 as being borne in an exemplary version of the non-transitory signal bearing medium n100 include one or more receiving information bar code instructions i1120, one or more receiving information holographic instructions i1121, one or more receiving information federally instructions i1122, one or more receiving information otc drug instructions i1123, one or more receiving information herbal instructions i1124, one or more receiving information homeopathic instructions i1125, one or more receiving information nutritional instructions i1126, one or more receiving information first medications instructions i1127, one or more receiving information second medications instructions i1128, one or more receiving information third medications instructions i1129, one or more receiving information fourth medications instructions i1130, one or more receiving fifth medications instructions i1131, one or more receiving information human instructions i1132, one or more receiving information ID card instructions i1133, one or more receiving information iris scan instructions i1134, one or more receiving information voice instructions i1135, one or more receiving information fingerprint instructions i1136, one or more receiving information dental instructions i1137, one or more receiving information RFID instructions i1138, and one or more receiving information password instructions i1139.

Figure 24:
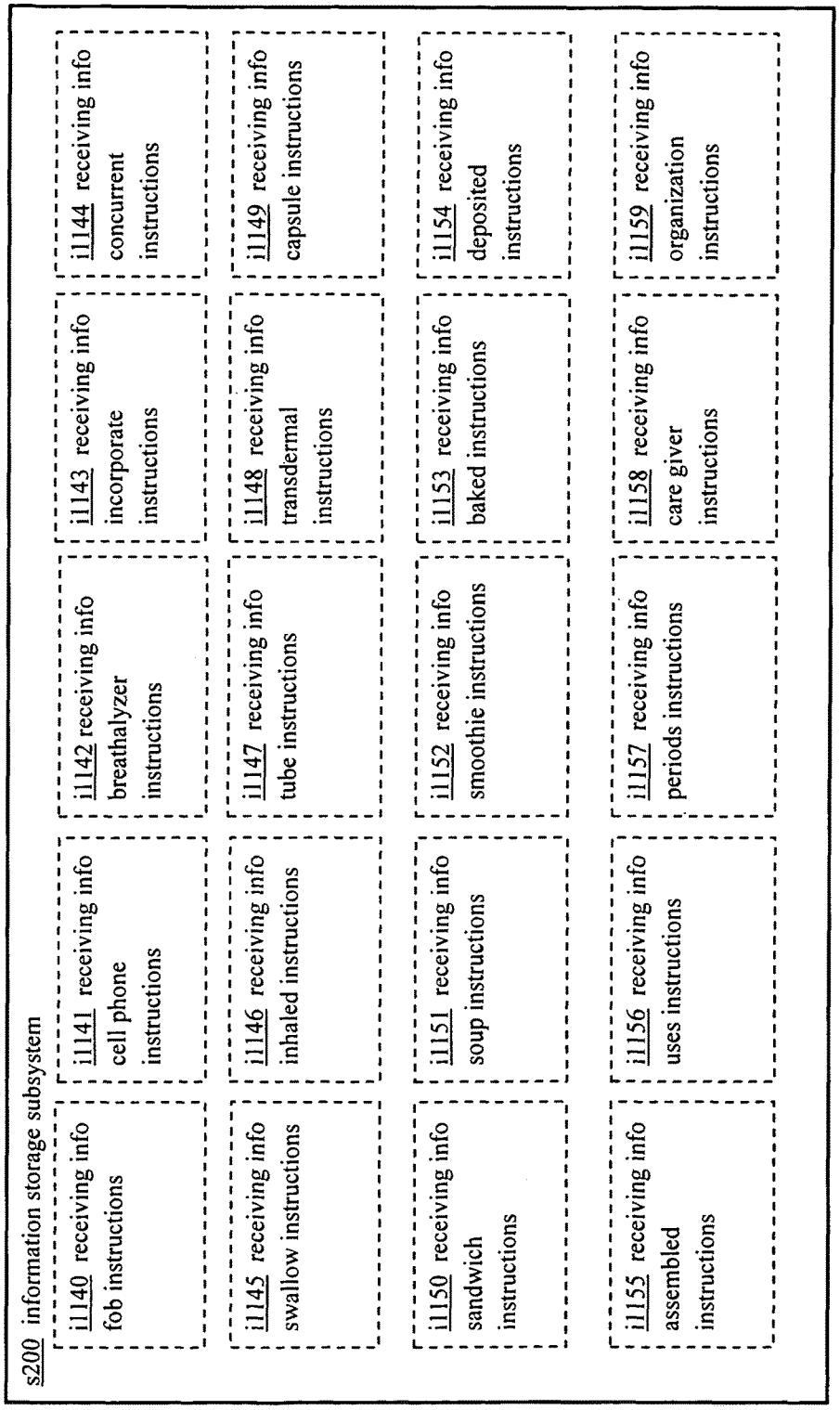
FIG. 24 is a block diagram depicting one or more exemplary instructions of the information storage subsystem s200 of the ingestible product reporting system 10 of FIG. 1.

One or more exemplary instructions depicted in FIG. 24 as being borne in an exemplary version of the non-transitory signal bearing medium n100 include one or more receiving information fob instructions i1140, one or more receiving information cell phone instructions i1141, one or more receiving information breathalyzer instructions i1142, one or more receiving information incorporate instructions i1143, one or more receiving information concurrent instructions i1144, one or more receiving information swallow instructions i1145, one or more receiving information inhaled instructions i1146, one or more receiving information tube instructions i1147, one or more receiving information transdermal instructions i1148, one or more receiving information capsule instructions i1149, one or more receiving information sandwich instructions i1150, one or more receiving information soup instructions i1151, one or more receiving information smoothie instructions i1152, one or more receiving information baked instructions i1153, one or more receiving information deposited instructions i1154, one or more receiving information assembled instructions i1155, one or more receiving information uses instructions i1156, one or more receiving information periods instructions i1157, one or more receiving information care giver instructions i1158, and one or more receiving information organization instructions i1159.

Figure 25:
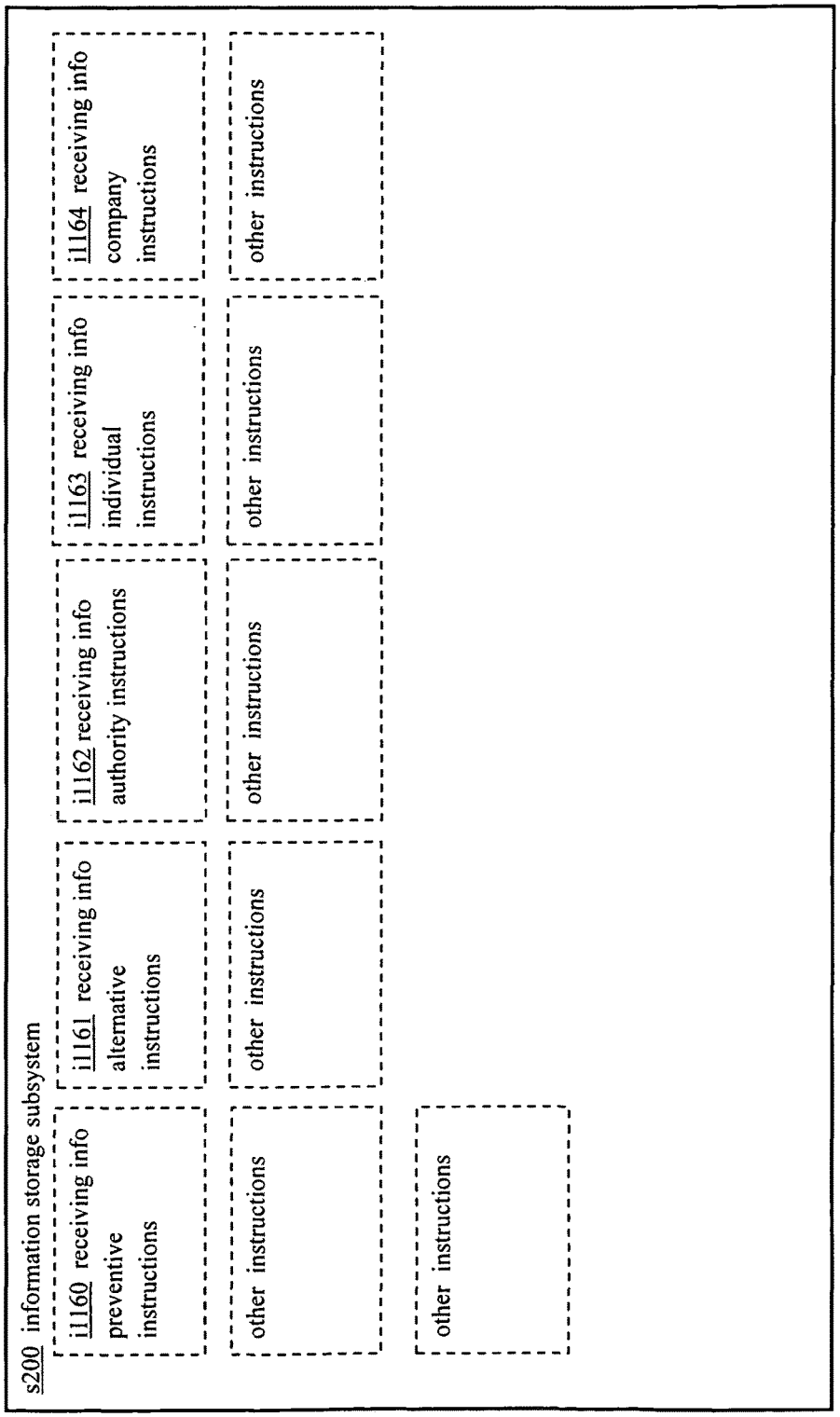
FIG. 25 is a block diagram depicting one or more exemplary instructions of the information storage subsystem s200 of the ingestible product reporting system 10 of FIG. 1.

One or more exemplary instructions depicted in FIG. 25 as being borne in an exemplary version of the non-transitory signal bearing medium n100 include one or more receiving information preventive instructions i1160, one or more receiving information alternative instructions i1161, one or more receiving information authority instructions i1162, one or more receiving information individual instructions i1163, and one or more receiving information company instructions i1164.

Figure 26:
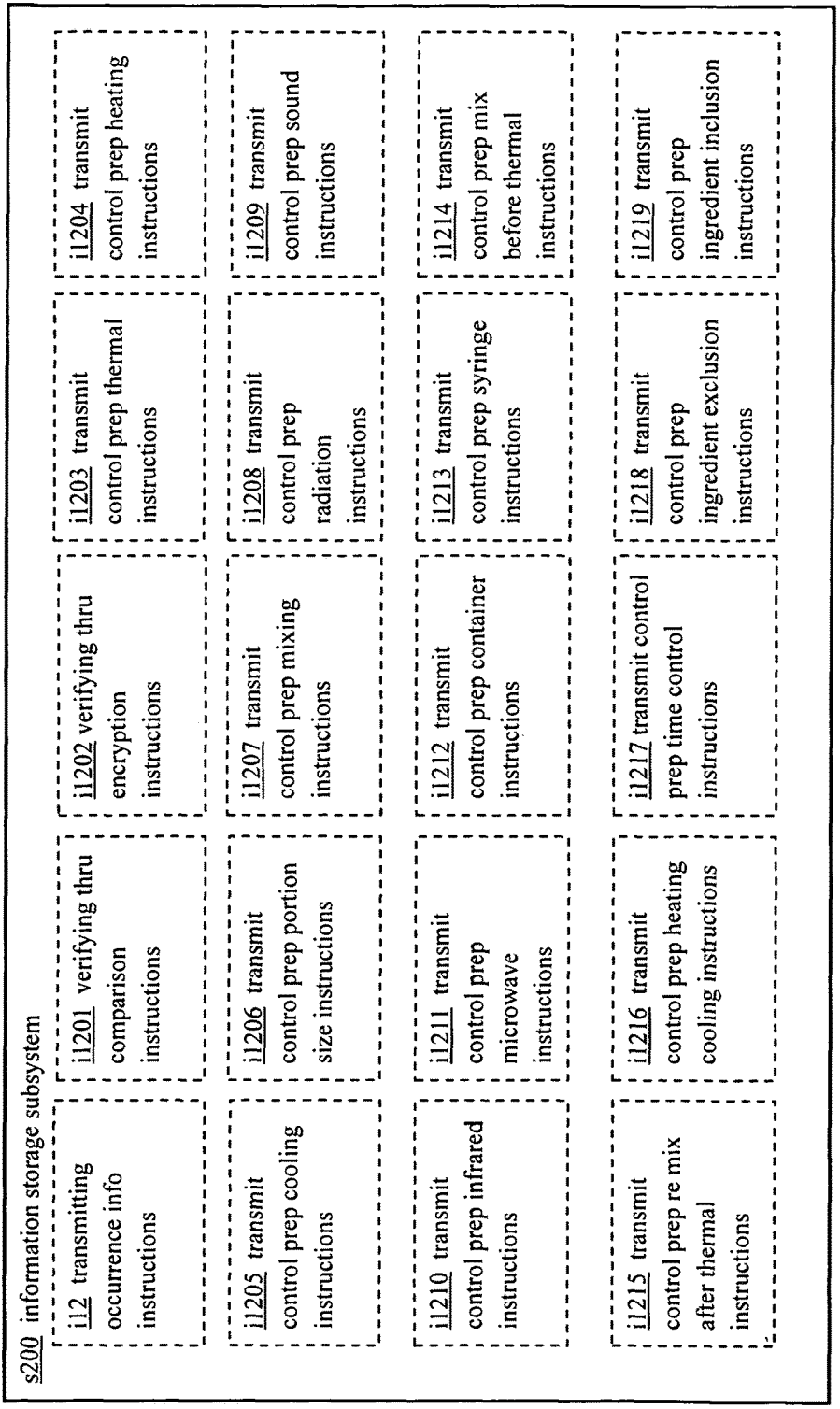
FIG. 26 is a block diagram depicting one or more exemplary instructions of the information storage subsystem s200 of the ingestible product reporting system 10 of FIG. 1.
Figure 27:
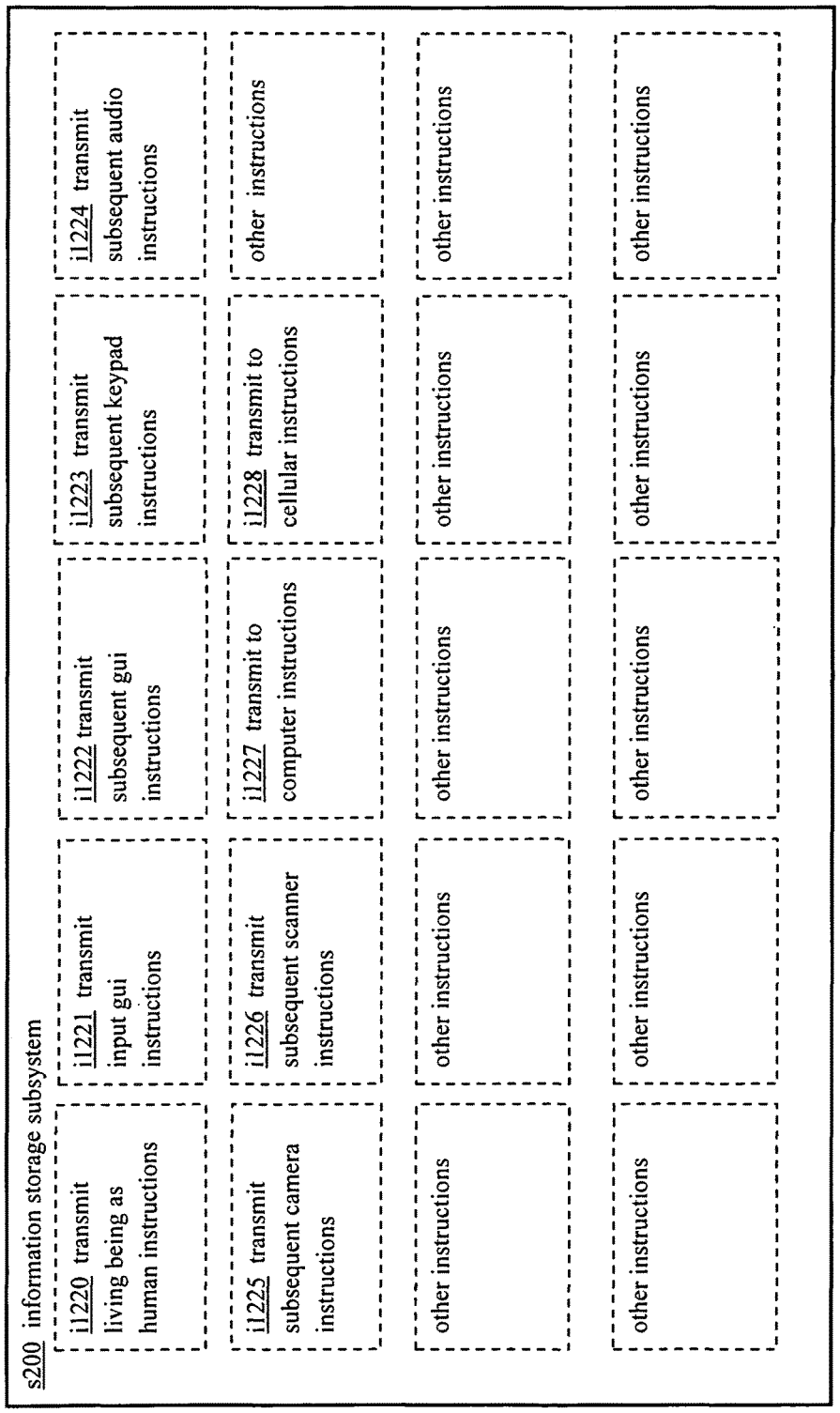
FIG. 27 is a block diagram depicting one or more exemplary instructions of the information storage subsystem s200 of the ingestible product reporting system 10 of FIG. 1.

One or more exemplary instructions depicted in FIG. 26 as being borne in an exemplary version of the non-transitory signal bearing medium n100 include one or more transmitting occurrence info instructions i12, one or more verifying thru comparison instructions i1201, one or more verifying thru encryption instructions i1202, one or more transmit control prep thermal instructions i1203, one or more transmit control prep heating instructions i1204, one or more transmit control prep cooling instructions i1205, one or more transmit control prep portion size instructions i1206, one or more transmit control prep mixing instructions i1207, one or more transmit control prep radiation instructions i1208, one or more transmit control prep sound instructions i1209, one or more transmit control prep infrared instructions i1210, one or more transmit control prep microwave instructions i1211, one or more transmit control prep container instructions i1212, one or more transmit control prep syringe instructions i1213, one or more transmit control prep mix before thermal instructions i1214, one or more transmit control prep re mix after thermal instructions i1215, one or more transmit control prep heating cooling instructions i1216, one or more transmit control prep time control instructions i1217, one or more transmit control prep ingredient exclusion instructions i1218, and one or more transmit control prep ingredient inclusion instructions i1219.

Implementations involve different combinations (otherwise known as "instruction") of components from the subsystems of the ingestible product reporting system 10. Some of these instruction are depicted in FIG. 21 to include one or more transmit living being as human instructions i1220, one or more transmit input gui instructions i1221, one or more transmit subsequent gui instructions i1222, one or more transmit subsequent keypad instructions i1223, one or more transmit subsequent audio instructions i1224, one or more transmit subsequent camera instructions i1225, one or more transmit subsequent scanner instructions i1226, one or more transmit to computer instructions i1227, and one or more transmit to cellular instructions i1228.

Figure 28:
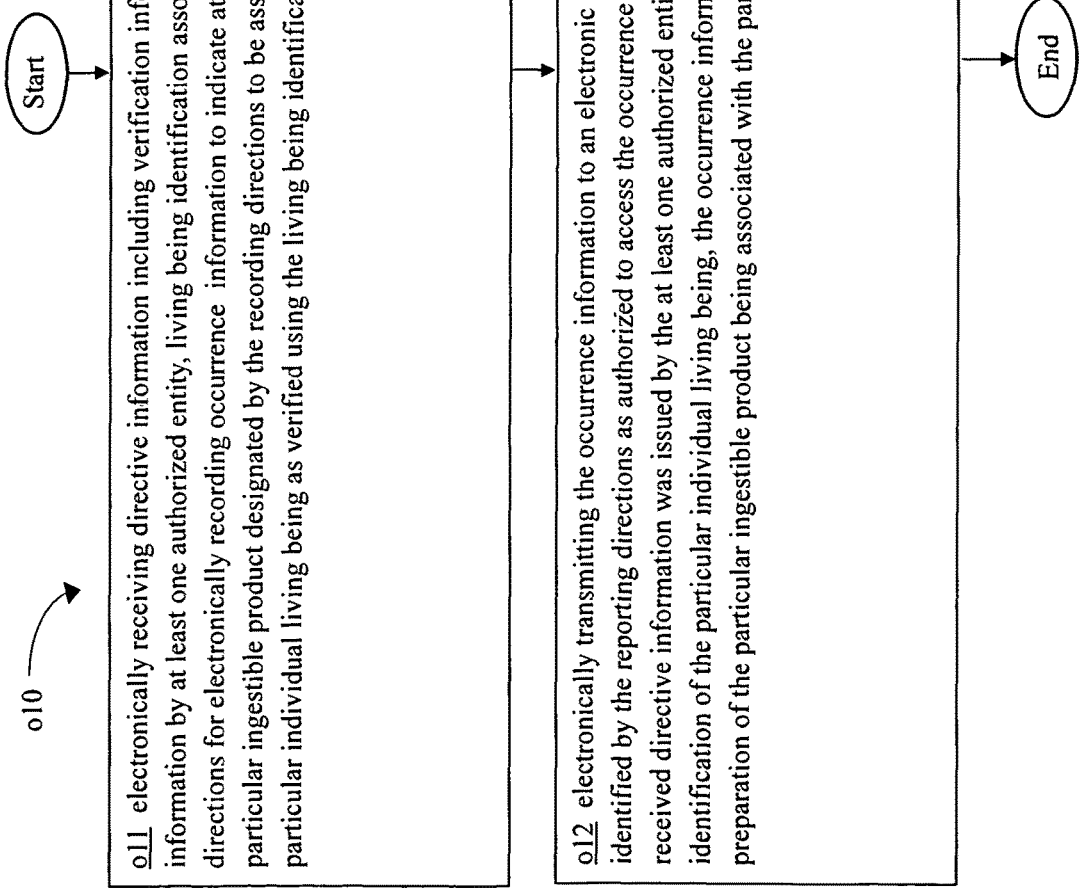
FIG. 28 is a high-level flowchart illustrating an operational flow o10 representing exemplary operations related to electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information, and electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being at least associated with the depicted exemplary implementations of the system.

An operational flow o10 as shown in FIG. 28 represents example operations related to receiving authorization information and directing fabrication of ingestible products based upon verification of the authorization.

FIG. 28 and those figures that follow may have various examples of operational flows, and explanation may be provided with respect to the above-described examples of FIGS. 1-24 and/or with respect to other examples and contexts. Nonetheless, it should be understood that the operational flows may be executed in a number of other environments and contexts, and/or in modified versions of FIGS. 1-24. Furthermore, although the various operational flows are presented in the sequence(s) illustrated, it should be understood that the various operations may be performed in other orders than those which are illustrated, or may be performed concurrently.

In FIG. 28 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 28, the operational flow o10 proceeds to operation o11 for electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information. An exemplary version of the non-transitory signal bearing medium n100 is depicted as bearing one or more receiving directive information instructions i11 that when executed will direct performance of the operation o11. In an implementation, the one or more receiving directive information instructions i11 when executed direct electronically receiving (e.g. the network cable component s502 carries information to the transceiver component s522, etc.) directive information including verification information to electronically verify issuance of the directive information by at least one authorized entity (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and reporting directions for electronically recording occurrence information to indicate at least one occurrence of at least partial preparation of a particular ingestible product (e.g. the multiprocessor component s112 directs the hard drive component s222 to store a information records indicating at least partial preparation of a smoothie, etc.) designated by the reporting directions to be associated with an electronically inputted identification of the particular individual living being (e.g. an elderly man uses the keyboard component s306) as verified using the living being identification electronically received with the directive information (e.g. the directive information includes textual identification information that can be inputted through use of a keyboard, etc.). Furthermore, the receiving directive information electrical circuitry arrangement ("elec circ arrange") e11 when activated will perform the operation o11. In an implementation, the receiving directive information electrical circuitry arrangement e11, when activated performs electronically receiving (e.g. the network cable component s502 carries information to the transceiver component s522, etc.) directive information including verification information to electronically verify issuance of the directive information by at least one authorized entity (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and reporting directions for electronically recording occurrence information to indicate at least one occurrence of at least partial preparation of a particular ingestible product (e.g. the multiprocessor component s112 directs the hard drive component s222 to store a information records indicating at least partial preparation of a smoothie, etc.) designated by the reporting directions to be associated with an electronically inputted identification of the particular individual living being (e.g. an elderly man uses the keyboard component s306) as verified using the living being identification electronically received with the directive information (e.g. the directive information includes textual identification information that can be inputted through use of a keyboard, etc.). In an implementation, the electronically receiving directive information including verification information to electronically verify issuance of the directive information by at least one authorized entity, living being identification associated with a particular individual living being, and reporting directions for electronically recording occurrence information to indicate at least one occurrence of at least partial preparation of a particular ingestible product designated by the reporting directions to be associated with an electronically inputted identification of the particular individual living being as verified using the living being identification electronically received with the directive information is carried out by electronically receiving (e.g. the network cable component s502 carries information to the transceiver component s522, etc.) directive information including verification information to electronically verify issuance of the directive information by at least one authorized entity (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and reporting directions for electronically recording occurrence information to indicate at least one occurrence of at least partial preparation of a particular ingestible product (e.g. the multiprocessor component s112 directs the hard drive component s222 to store a information records indicating at least partial preparation of a smoothie, etc.) designated by the reporting directions to be associated with an electronically inputted identification of the particular individual living being (e.g. an elderly man uses the keyboard component s306) as verified using the living being identification electronically received with the directive information (e.g. the directive information includes textual identification information that can be inputted through use of a keyboard, etc.).

Figure 29:
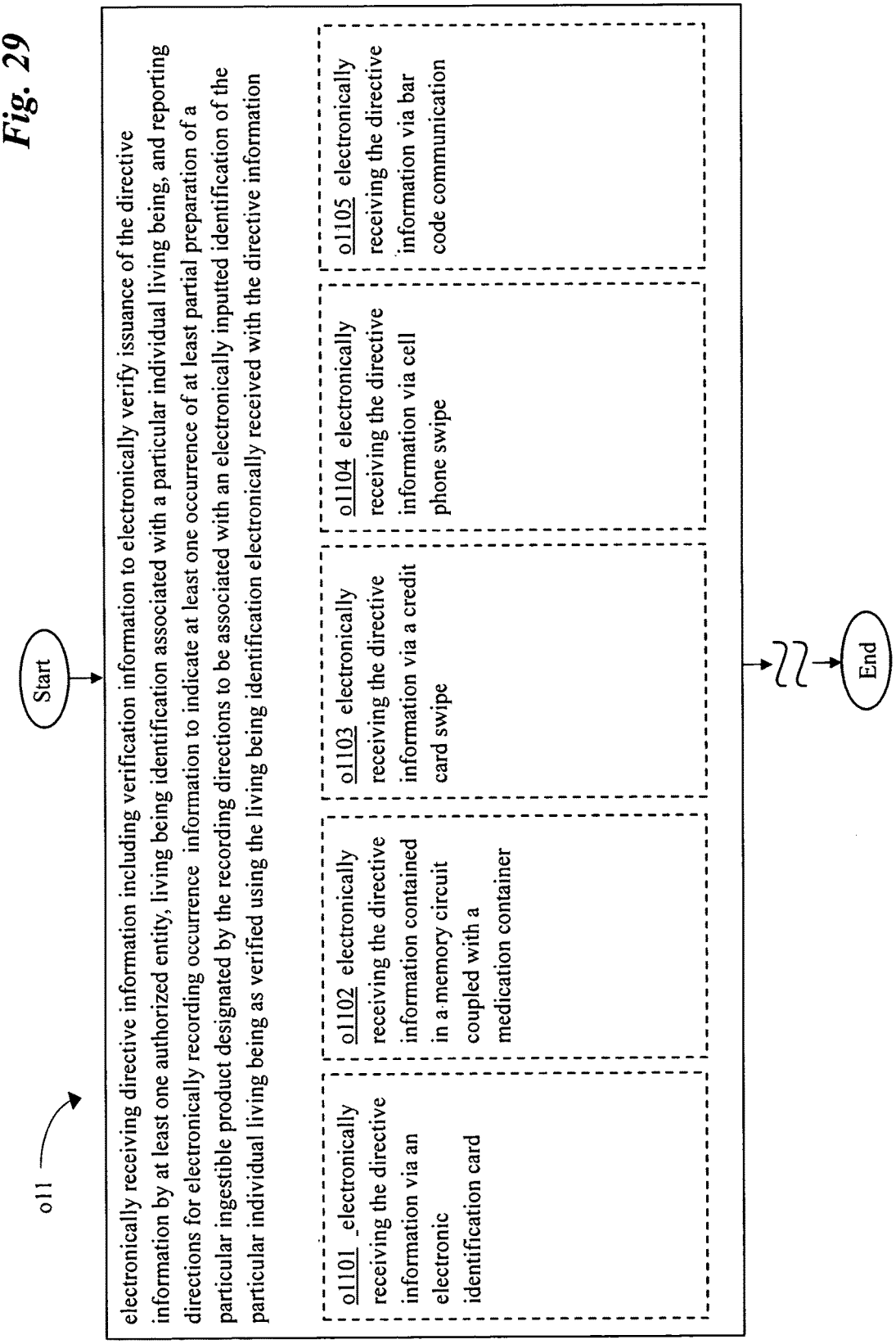
FIG. 29 is a high-level flowchart including exemplary implementations of operation O11 of FIG. 28.

In one or more implementations, as shown in FIG. 29, operation o11 includes an operation o1101 for electronically receiving the directive information via an electronic identification card. An exemplary version of the non-transitory signal bearing medium n100 is depicted as bearing one or more receiving information ID card instructions i1101 that when executed will direct performance of the operation o1101. In an implementation, the one or more receiving information ID card instructions i1101 when executed direct electronically receiving the directive information via an electronic identification card (e.g. an implementation of the receiver component s528 is configured to electronically engage with a card having memory storage holding the direction information, etc.). Furthermore, the receiving information ID card electrical circuitry arrangement ("elec circ arrange") e1101 when activated will perform the operation o1101. In an implementation, the receiving information ID card electrical circuitry arrangement e1101, when activated performs electronically receiving the directive information via an electronic identification card (e.g. an implementation of the receiver component s528 is configured to electronically engage with a card having memory storage holding the direction information, etc.). In an implementation, the electronically receiving the directive information via an electronic identification card is carried out by electronically receiving the directive information via an electronic identification card (e.g. an implementation of the receiver component s528 is configured to electronically engage with a card having memory storage holding the direction information, etc.).

In one or more implementations, operation o11 includes an operation o1102 for electronically receiving the directive information contained in a memory circuit coupled with a medication container. An exemplary version of the non-transitory signal bearing medium n100 is depicted as bearing one or more receiving information memory instructions i1102 that when executed will direct performance of the operation o1102. In an implementation, the one or more receiving information memory instructions i1102 when executed direct electronically receiving the directive information contained in a memory circuit coupled with a medication container (e.g. an implementation of the receiver component s528 is configured to electronically engage with a memory storage coupled with a medication container to receive the directive information in electronic form, etc.). Furthermore, the receiving information memory electrical circuitry arrangement e1102 when activated will perform the operation o1102. In an implementation, the receiving information memory electrical circuitry arrangement e1102, when activated performs electronically receiving the directive information contained in a memory circuit coupled with a medication container (e.g. an implementation of the receiver component s528 is configured to electronically engage with a memory storage coupled with a medication container to receive the directive information in electronic form, etc.). In an implementation, the electronically receiving the directive information contained in a memory circuit coupled with a medication container is carried out by electronically receiving the directive information contained in a memory circuit coupled with a medication container (e.g. an implementation of the receiver component s528 is configured to electronically engage with a memory storage coupled with a medication container to receive the directive information in electronic form, etc.).

In one or more implementations, operation o11 includes an operation o1103 for electronically receiving the directive information via a credit card swipe. An exemplary version of the non-transitory signal bearing medium n100 is depicted as bearing one or more receiving information credit card instructions i1103 that when executed will direct performance of the operation o1103. In an implementation, the one or more receiving information credit card instructions i1103 when executed direct electronically receiving the directive information via a credit card swipe (e.g. an implementation of the receiver component s528 is configured to electronically engage with an electronic memory stripe integrated into a credit card to receive the directive information, etc.). Furthermore, the receiving information credit card electrical circuitry arrangement e1103 when activated will perform the operation o1103. In an implementation, the receiving information credit card electrical circuitry arrangement e1103, when activated performs electronically receiving the directive information via a credit card swipe (e.g; an implementation of the receiver component s528 is configured to electronically engage with an electronic memory stripe integrated into a credit card to receive the directive information, etc.). In an implementation, the is electronically receiving the directive information via a credit card swipe carried out by electronically receiving the directive information via a credit card swipe (e.g. an implementation of the receiver component s528 is configured to electronically engage with an electronic memory stripe integrated into a credit card to receive the directive information, etc.).

In one or more implementations, operation o11 includes an operation o1104 for electronically receiving the directive information via cell phone swipe. An exemplary version of the non-transitory signal bearing medium n100 is depicted as bearing one or more receiving information cell phone instructions i1104 that when executed will direct performance of the operation o1104. In an implementation, the one or more receiving information cell phone instructions i1104 when executed direct electronically receiving the directive information via cell phone swipe (e.g. an implementation of the receiver component s528 is configured to electronically engage with an electronic memory component integrated into a cell phone to receive the directive information, etc.). Furthermore, the receiving information cell phone electrical circuitry arrangement e1104 when activated will perform the operation o1104. In an implementation, the receiving information cell phone electrical circuitry arrangement e1104, when activated performs electronically receiving the directive information via cell phone swipe (e.g. an implementation of the receiver component s528 is configured to electronically engage with an electronic memory component integrated into a cell phone to receive the directive information, etc.). In an implementation, the is electronically receiving the directive information via cell phone swipe carried out by electronically receiving the directive information via cell phone swipe (e.g. an implementation of the receiver component s528 is configured to electronically engage with an electronic memory component integrated into a cell phone to receive the directive information, etc.).

In one or more implementations, operation o11 includes an operation o1105 for electronically receiving the directive information via bar code communication. An exemplary version of the non-transitory signal bearing medium n100 is depicted as bearing one or more receiving information bar code instructions i1105 that when executed will direct performance of the operation o1105. In an implementation, the one or more receiving information bar code instructions i1105 when executed direct electronically receiving the directive information via bar code communication (e.g. an implementation of the receiver component s528 is configured to electronically read a bar code label to receive the directive information, etc.). Furthermore, the receiving information bar code electrical circuitry arrangement e1105 when activated will perform the operation o1105. In an implementation, the receiving information bar code electrical circuitry arrangement e1105, when activated performs electronically receiving the directive information via bar code communication (e.g. an implementation of the receiver component s528 is configured to electronically read a bar code label to receive the directive information, etc.). In an implementation, the electronically receiving the directive information via bar code communication is carried out by electronically receiving the directive information via bar code communication (e.g. an implementation of the receiver component s528 is configured to electronically read a bar code label to receive the directive information, etc.).

Figure 30:
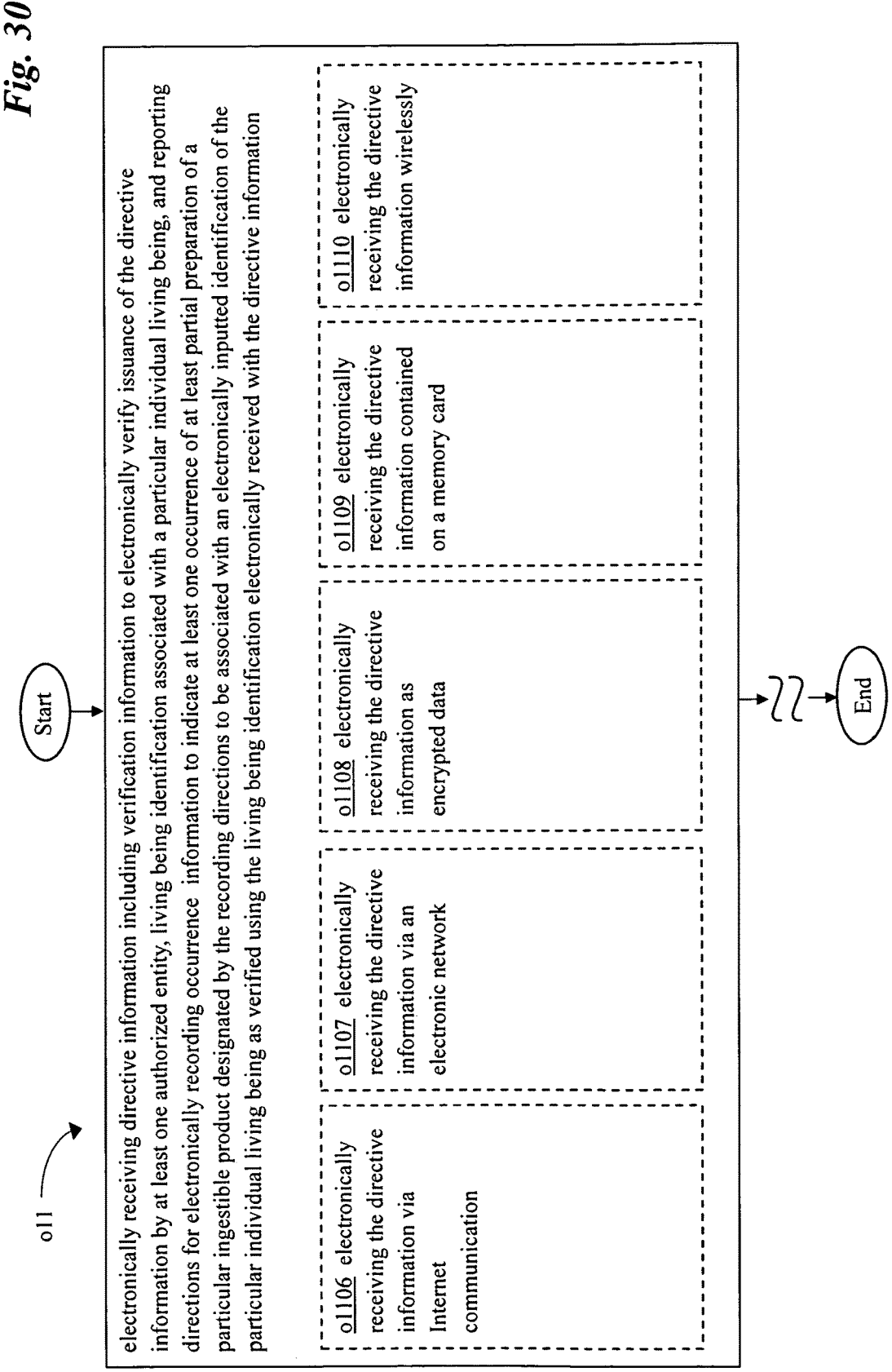
FIG. 30 is a high-level flowchart including exemplary implementations of operation O11 of FIG. 28.

In one or more implementations, as shown in FIG. 30, operation o11 includes an operation o1106 for electronically receiving the directive information via Internet communication. An exemplary version of the non-transitory signal bearing medium n100 is depicted as bearing one or more receiving information Internet instructions i1106 that when executed will direct performance of the operation o1106. In an implementation, the one or more receiving information Internet instructions i1106 when executed direct electronically receiving the directive information via Internet communication (e.g. an implementation of the receiver component s528 is configured to electronically receive through the internet network component s508 the directive information, etc.). Furthermore, the receiving information Internet electrical circuitry arrangement e1106 when activated will perform the operation o1106. In an implementation, the receiving information Internet electrical circuitry arrangement e1106, when activated performs electronically receiving the directive information via Internet communication (e.g. an implementation of the receiver component s528 is configured to electronically receive through the internet network component s508 the directive information, etc.). In an implementation, the electronically receiving the directive information via Internet communication is carried out by electronically receiving the directive information via Internet communication (e.g. an implementation of the receiver component s528 is configured to electronically receive through the internet network component s508 the directive information, etc.).

In one or more implementations, operation o11 includes an operation o1107 for electronically receiving the directive information via an electronic network. An exemplary version of the non-transitory signal bearing medium n100 is depicted as bearing one or more receiving information network instructions i1107 that when executed will direct performance of the operation o1107. In an implementation, the one or more receiving information network instructions i1107 when executed direct electronically receiving the directive information via an electronic network (e.g. an implementation of the receiver component s528 is configured to electronically engage with the network cable component s502 to receive the directive information, etc.). Furthermore, the receiving information network electrical circuitry arrangement e1107 when activated will perform the operation o1107. In an implementation, the receiving information network electrical circuitry arrangement e1107, when activated performs electronically receiving the directive information via an electronic network (e.g. an implementation of the receiver component s528 is configured to electronically engage with the network cable component s502 to receive the directive information, etc.). In an implementation, the electronically receiving the directive information via an electronic network is carried out by electronically receiving the directive information via an electronic network (e.g. an implementation of the receiver component s528 is configured to electronically engage with the network cable component s502 to receive the directive information, etc.).

In one or more implementations, operation o11 includes an operation o1108 for electronically receiving the directive information as encrypted data. An exemplary version of the non-transitory signal bearing medium n100 is depicted as bearing one or more receiving encrypted information instructions i1108 that when executed will direct performance of the operation o1108. In an implementation, the one or more receiving encrypted information instructions i1108 when executed direct electronically receiving the directive information as encrypted data (e.g. an implementation of the receiver component s528 is configured to electronically receive through the encrypted communication component s520 the directive information, etc.). Furthermore, the receiving encrypted information electrical circuitry arrangement e1108 when activated will perform the operation o1108. In an implementation, the receiving encrypted information electrical circuitry arrangement e1108, when activated performs electronically receiving the directive information as encrypted data (e.g. an implementation of the receiver component s528 is configured to electronically receive through the encrypted communication component s520 the directive information, etc.). In an implementation, the electronically receiving the directive information as encrypted data is carried out by electronically receiving the directive information as encrypted data (e.g. an implementation of the receiver component s528 is configured to electronically receive through the encrypted communication component s520 the directive information, etc.).

In one or more implementations, operation o11 includes an operation o1109 for electronically receiving the directive information contained on a memory card. An exemplary version of the non-transitory signal bearing medium n100 is depicted as bearing one or more receiving information memory card instructions i1109 that when executed will direct performance of the operation o1109. In an implementation, the one or more receiving information memory card instructions i1109 when executed direct electronically receiving the directive information contained on a memory card (e.g. an implementation of the receiver component s528 is configured to electronically engage with an electronic memory card to receive the directive information, etc.). Furthermore, the receiving information memory card electrical circuitry arrangement e1109 when activated will perform the operation o1109. In an implementation, the receiving information memory card electrical circuitry arrangement e1109, when activated performs electronically receiving the directive information contained on a memory card (e.g. an implementation of the receiver component s528 is configured to electronically engage with an electronic memory card to receive the directive information, etc.). In an implementation, the electronically receiving the directive information contained on a memory card is carried out by electronically receiving the directive information contained on a memory card (e.g. an implementation of the receiver component s528 is configured to electronically engage with an electronic memory card to receive the directive information, etc.).

In one or more implementations, operation o11 includes an operation o1110 for electronically receiving the directive information wirelessly. An exemplary version of the non-transitory signal bearing medium n100 is depicted as bearing one or more receiving information wirelessly instructions i1110 that when executed will direct performance of the operation o1110. In an implementation, the one or more receiving information wirelessly instructions i1110 when executed direct electronically receiving the directive information wirelessly (e.g. an implementation of the receiver component s528 is configured to electronically receive through the wireless network component s512 the directive information, etc.). Furthermore, the receiving information wirelessly electrical circuitry arrangement e1110 when activated will perform the operation o1110. In an implementation, the receiving information wirelessly electrical circuitry arrangement e1110, when activated performs electronically receiving the directive information wirelessly (e.g. an implementation of the receiver component s528 is configured to electronically receive through the wireless network component s512 the directive information, etc.). In an implementation, the electronically receiving the directive information wirelessly is carried out by electronically receiving the directive information wirelessly (e.g. an implementation of the receiver component s528 is configured to electronically receive through the wireless network component s512 the directive information, etc.).

Figure 31:
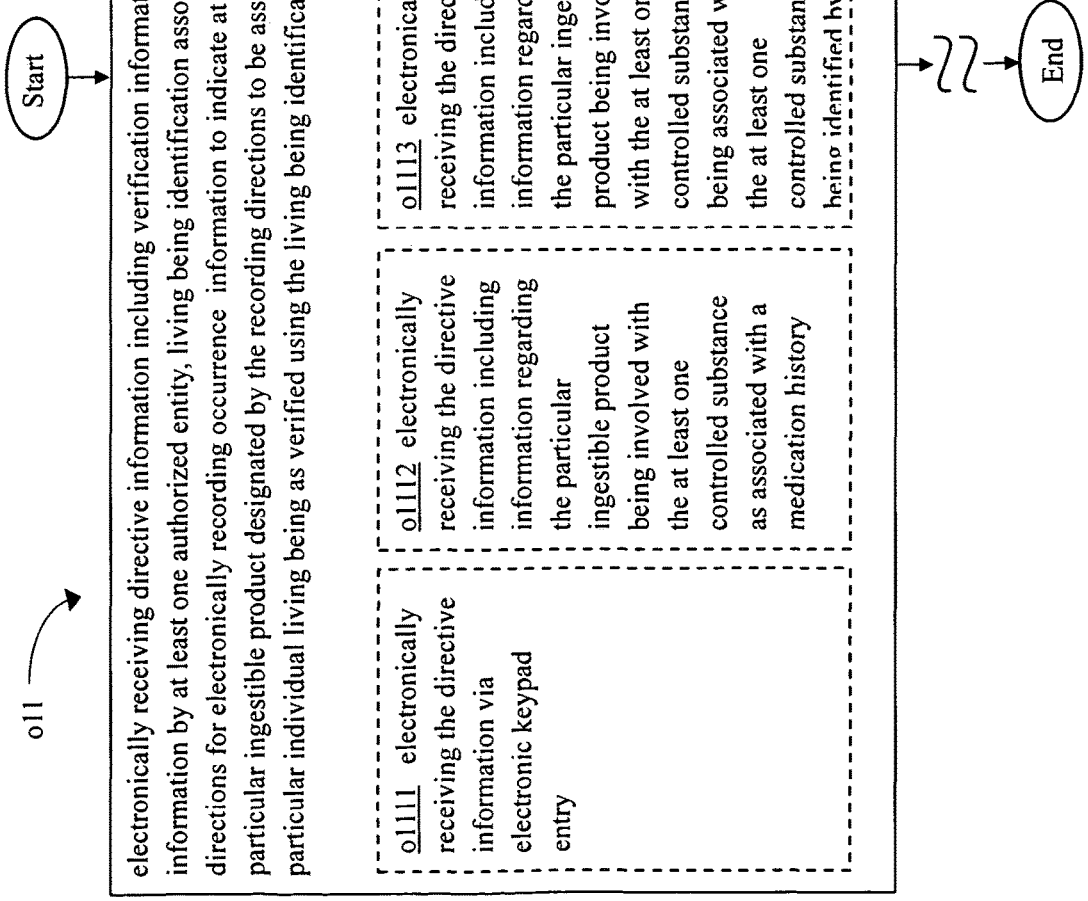
FIG. 31 is a high-level flowchart including exemplary implementations of operation O11 of FIG. 28.

In one or more implementations, as shown in FIG. 31, operation o11 includes an operation o1111 for electronically receiving the directive information via electronic keypad entry. An exemplary version of the non-transitory signal bearing medium n100 is depicted as bearing one or more receiving information keypad entry instructions i1111 that when executed will direct performance of the operation o1111. In an implementation, the one or more receiving information keypad entry instructions i1111 when executed direct electronically receiving the directive information via electronic keypad entry (e.g. an implementation of the receiver component s528 is configured to electronically engage with the keypad component s308 to receive the directive information as inputted by a user, etc.). Furthermore, the receiving information keypad entry electrical circuitry arrangement e1111 when activated will perform the operation o1111. In an implementation, the receiving information keypad entry electrical circuitry arrangement e1111, when activated performs electronically receiving the directive information via electronic keypad entry (e.g. an implementation of the receiver component s528 is configured to electronically engage with the keypad component s308 to receive the directive information as inputted by a user, etc.). In an implementation, the electronically receiving the directive information via electronic keypad entry is carried out by electronically receiving the directive information via electronic keypad entry (e.g. an implementation of the receiver component s528 is configured to electronically engage with the keypad component s308 to receive the directive information as inputted by a user, etc.).

In one or more implementations, operation o11 includes an operation o1112 for electronically receiving the directive information including information regarding the particular ingestible product being involved with the at least one controlled substance as associated with a medication history. An exemplary version of the non-transitory signal bearing medium n100 is depicted as bearing one or more receiving information meds history instructions i1112 that when executed will direct performance of the operation o1112. In an implementation, the one or more receiving information meds history instructions i1112 when executed direct electronically receiving the directive information including information regarding the particular ingestible product being involved with at least one controlled substance as associated with a medication history (e.g. an implementation of the receiver component s528 is configured to electronically engage with the processor component s102 to receive the directive information including information regarding the particular ingestible product as determined by the processor component as being involved with the at least one controlled substance and a name and control number of the medication history of the particular individual living being, etc.). Furthermore, the receiving information meds history electrical circuitry arrangement e1112 when activated will perform the operation o1112. In an implementation, the receiving information meds history electrical circuitry arrangement e1112, when activated performs electronically receiving the directive information including information regarding the particular ingestible product being involved with at least one controlled substance as associated with a medication history (e.g. an implementation of the receiver component s528 is configured to electronically engage with the processor component s102 to receive the directive information including information regarding the particular ingestible product as determined by the processor component as being involved with the at least one controlled substance and a name and control number of the medication history of the particular individual living being, etc.). In an implementation, the electronically receiving the directive information including information regarding the particular ingestible product being involved with the at least one controlled substance as associated with a medication history is carried out by electronically receiving the directive information including information regarding the particular ingestible product being involved with at least one controlled substance as associated with a medication history (e.g. an implementation of the receiver component s528 is configured to electronically engage with the processor component s102 to receive the directive information including information regarding the particular ingestible product as determined by the processor component as being involved with the at least one controlled substance and a name and control number of the medication history of the particular individual living being, etc.).

In one or more implementations, operation o11 includes an operation o1113 for electronically receiving the directive information including information regarding the particular ingestible product being involved with the at least one controlled substance being associated with the at least one controlled substance being identified by a prescription identification. An exemplary version of the non-transitory signal bearing medium n100 is depicted as bearing one or more receiving information prescription ID instructions i1113 that when executed will direct performance of the operation o1113. In an implementation, the one or more receiving information prescription ID instructions i1113 when executed direct electronically receiving the directive information including information regarding the particular ingestible product being involved with the at least one controlled substance being associated with the at least one controlled substance being identified by a prescription identification (e.g. an implementation of the receiver component s528 is configured to electronically engage with the processor component s102 to receive the directive information including information regarding the particular ingestible product being involved with the at least one controlled substance being associated with the at least one controlled substance being identified by a prescription identification, etc.). Furthermore, the receiving information prescription ID electrical circuitry arrangement e1113 when activated will perform the operation o1113. In an implementation, the receiving information prescription ID electrical circuitry arrangement e1113, when activated performs electronically receiving the directive information including information regarding the particular ingestible product being involved with the at least one controlled substance being associated with the at least one controlled substance being identified by a prescription identification (e.g. an implementation of the receiver component s528 is configured to electronically engage with the processor component s102 to receive the directive information including information regarding the particular ingestible product being involved with the at least one controlled substance being associated with the at least one controlled substance being identified by a prescription identification, etc.). In an implementation, the electronically receiving the directive information including information regarding the particular ingestible product being involved with the at least one controlled substance being associated with the at least one controlled substance being identified by a prescription identification is carried out by electronically receiving the directive information including information regarding the particular ingestible product being involved with the at least one controlled substance being associated with the at least one controlled substance being identified by a prescription identification (e.g. an implementation of the receiver component s528 is configured to electronically engage with the processor component s102 to receive the directive information including information regarding the particular ingestible product being involved with the at least one controlled substance being associated with the at least one controlled substance being identified by a prescription identification, etc.).

In one or more implementations, operation o11 includes an operation o1114 for electronically receiving the directive information including information regarding the particular ingestible product being involved with at least one controlled substance associated with a prescription serial number. An exemplary version of the non-transitory signal bearing medium n100 is depicted as bearing one or more receiving information prescription number instructions i1114 that when executed will direct performance of the operation o1114. In an implementation, the one or more receiving information prescription number instructions i1114 when executed direct electronically receiving the directive information including information regarding the particular ingestible product being involved with at least one controlled substance associated with a prescription serial number (e.g. an implementation of the receiver component s528 is configured to electronically engage with the processor component s102 to receive the directive information including information regarding the particular ingestible product being involved with at least one controlled substance associated with a prescription serial number for the controlled substance, etc.). Furthermore, the receiving information prescription number electrical circuitry arrangement e1114 when activated will perform the operation o1114. In an implementation, the receiving information prescription number electrical circuitry arrangement e1114, when activated performs electronically receiving the directive information including information regarding the particular ingestible product being involved with at least one controlled substance associated with a prescription serial number (e.g. an implementation of the receiver component s528 is configured to electronically engage with the processor component s102 to receive the directive information including information regarding the particular ingestible product being involved with at least one controlled substance associated with a prescription serial number for the controlled substance, etc.). In an implementation, the electronically receiving the directive information including information regarding the particular ingestible product being involved with at least one controlled substance associated with a prescription serial number is carried out by electronically receiving the directive information including information regarding the particular ingestible product being involved with at least one controlled substance associated with a prescription serial number (e.g. an implementation of the receiver component s528 is configured to electronically engage with the processor component s102 to receive the directive information including information regarding the particular ingestible product being involved with at least one controlled substance associated with a prescription serial number for the controlled substance, etc.).

In one or more implementations, operation o11 includes an operation o1115 for electronically receiving the directive information including information regarding the particular ingestible product being involved with at least one controlled substance associated with a data image of handwritten text. An exemplary version of the non-transitory signal bearing medium n100 is depicted as bearing one or more receiving information handwritten instructions i1115 that when executed will direct performance of the operation o1115. In an implementation, the one or more receiving information handwritten instructions i1115 when executed direct electronically receiving the directive information including information regarding the particular ingestible product being involved with at least one controlled substance associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.). Furthermore, the receiving information handwritten electrical circuitry arrangement e1115 when activated will perform the operation o1115. In an implementation, the receiving information handwritten electrical circuitry arrangement e1115, when activated performs electronically receiving the directive information including information regarding the particular ingestible product being involved with at least one controlled substance associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.). In an implementation, the electronically receiving the directive information including information regarding the particular ingestible product being involved with at least one controlled substance associated with a data image of handwritten text is carried out by electronically receiving the directive information including information regarding the particular ingestible product being involved with at least one controlled substance associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.).

Figure 32:
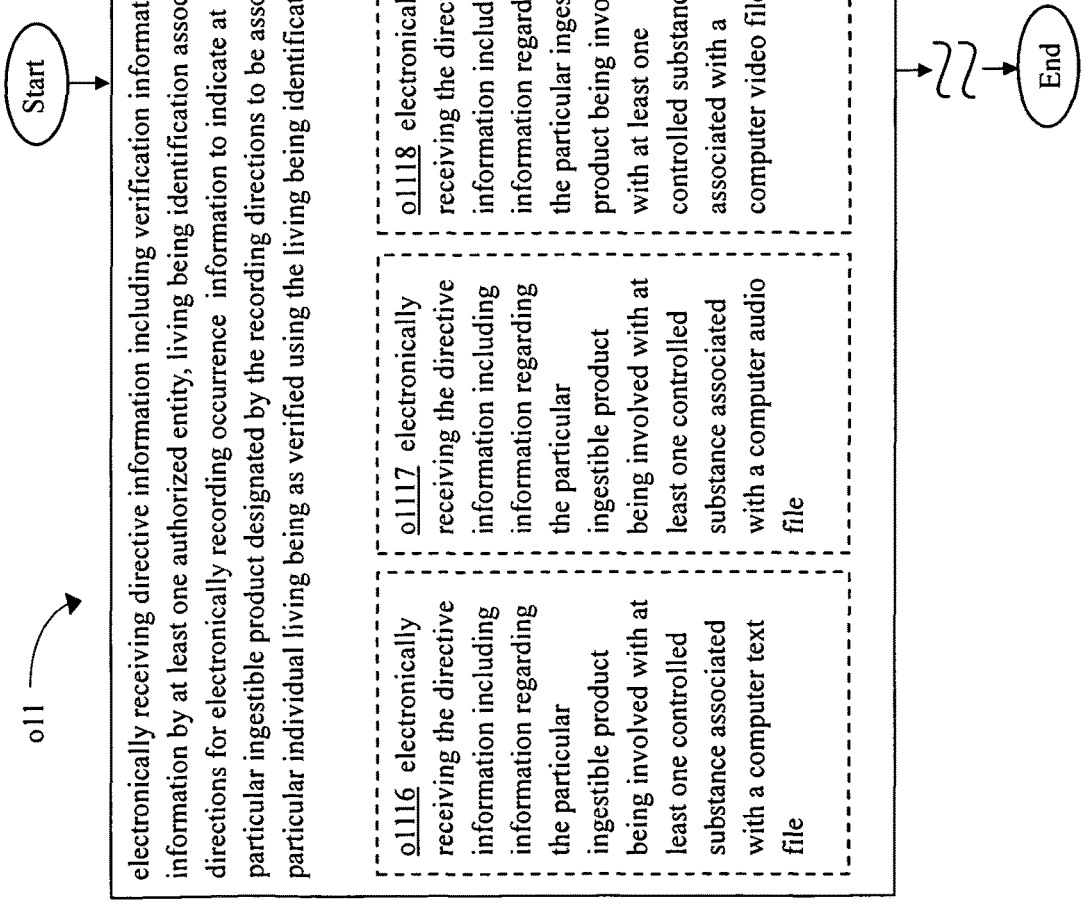
FIG. 32 is a high-level flowchart including exemplary implementations of operation O11 of FIG. 28.

In one or more implementations, as shown in FIG. 32, operation o11 includes an operation o1116 for electronically receiving the directive information including information regarding the particular ingestible product being involved with at least one controlled substance associated with a computer text file. An exemplary version of the non-transitory signal bearing medium n100 is depicted as bearing one or more receiving information text file instructions i1116 that when executed will direct performance of the operation o1116. In an implementation, the one or more receiving information text file instructions i1116 when executed direct electronically receiving the directive information including information regarding the particular ingestible product being involved with at least one controlled substance associated with a computer text file (e.g. an implementation of the receiver component s528 is configured to electronically engage with the processor component s102 information regarding the particular ingestible product being involved with at least one controlled substance identification as determined by the processor component through electronic reading of the computer text file, etc.). Furthermore, the receiving information text file electrical circuitry arrangement e1116 when activated will perform the operation o1116. In an implementation, the receiving information text file electrical circuitry arrangement e1116, when activated performs electronically receiving the directive information including information regarding the particular ingestible product being involved with at least one controlled substance associated with a computer text file (e.g. an implementation of the receiver component s528 is configured to electronically engage with the processor component s102 information regarding the particular ingestible product being involved with at least one controlled substance identification as determined by the processor component through electronic reading of the computer text file, etc.). In an implementation, the electronically receiving the directive information including information regarding the particular ingestible product being involved with at least one controlled substance associated with a computer text file is carried out by electronically receiving the directive information including information regarding the particular ingestible product being involved with at least one controlled substance associated with a computer text file (e.g. an implementation of the receiver component s528 is configured to electronically engage with the processor component s102 information regarding the particular ingestible product being involved with at least one controlled substance identification as determined by the processor component through electronic reading of the computer text file, etc.).

In one or more implementations, operation o11 includes an operation o1117 for electronically receiving the directive information including information regarding the particular ingestible product being involved with at least one controlled substance associated with a computer audio file. An exemplary version of the non-transitory signal bearing medium n100 is depicted as bearing one or more receiving information audio file instructions i1117 that when executed will direct performance of the operation o1117. In an implementation, the one or more receiving information audio file instructions i1117 when executed direct electronically receiving the directive information including information regarding the particular ingestible product being involved with at least one controlled substance associated with a computer audio file (e.g. an implementation of the receiver component s528 is configured to electronically engage with the processor component s102 to receive the directive information including information regarding the particular ingestible product being involved with at least one controlled substance as determined by the processor component through electronic reading of the computer audio file, etc.). Furthermore, the receiving information audio file electrical circuitry arrangement e1117 when activated will perform the operation o1117. In an implementation, the receiving information audio file electrical circuitry arrangement e1117, when activated performs electronically receiving the directive information including information regarding the particular ingestible product being involved with at least one controlled substance associated with a computer audio file (e.g. an implementation of the receiver component s528 is configured to electronically engage with the processor component s102 to receive the directive information including information regarding the particular ingestible product being involved with at least one controlled substance as determined by the processor component through electronic reading of the computer audio file, etc.). In an implementation, the electronically receiving the directive information including information regarding the particular ingestible product being involved with at least one controlled substance associated with a computer audio file is carried out by electronically receiving the directive information including information regarding the particular ingestible product being involved with at least one controlled substance associated with a computer audio file (e.g. an implementation of the receiver component s528 is configured to electronically engage with the processor component s102 to receive the directive information including information regarding the particular ingestible product being involved with at least one controlled substance as determined by the processor component through electronic reading of the computer audio file, etc.).

In one or more implementations, operation o11 includes an operation o1118 for electronically receiving the directive information including information regarding the particular ingestible product being involved with at least one controlled substance associated with a computer video file. An exemplary version of the non-transitory signal bearing medium n100 is depicted as bearing one or more receiving information video file instructions i1118 that when executed will direct performance of the operation o1118. In an implementation, the one or more receiving information video file instructions i1118 when executed direct electronically receiving the directive information including information regarding the particular ingestible product being involved with at least one controlled substance associated with a computer video file (e.g. an implementation of the receiver component s528 is configured to electronically engage with the processor component s102 to receive the directive information including information regarding the particular ingestible product being involved with at least one controlled substance as determined by the processor component through electronic reading of the computer video file, etc.). Furthermore, the receiving information video file electrical circuitry arrangement e1118 when activated will perform the operation o1118. In an implementation, the receiving information video file electrical circuitry arrangement e1118, when activated performs electronically receiving the directive information including information regarding the particular ingestible product being involved with at least one controlled substance associated with a computer video file (e.g. an implementation of the receiver component s528 is configured to electronically engage with the processor component s102 to receive the directive information including information regarding the particular ingestible product being involved with at least one controlled substance as determined by the processor component through electronic reading of the computer video file, etc.). In an implementation, the electronically receiving the directive information including information regarding the particular ingestible product being involved with at least one controlled substance associated with a computer video file is carried out by electronically receiving the directive information including information regarding the particular ingestible product being involved with at least one controlled substance associated with a computer video file (e.g. an implementation of the receiver component s528 is configured to electronically engage with the processor component s102 to receive the directive information including information regarding the particular ingestible product being involved with at least one controlled substance as determined by the processor component through electronic reading of the computer video file, etc.).

In one or more implementations, operation o11 includes an operation o1119 for electronically receiving the directive information including information regarding the particular ingestible product being involved with at least one controlled substance associated with an RFID tag. An exemplary version of the non-transitory signal bearing medium n100 is depicted as bearing one or more receiving information RFID instructions i1119 that when executed will direct performance of the operation o1119. In an implementation, the one or more receiving information RFID instructions i1119 when executed direct electronically receiving the directive information including information regarding the particular ingestible product being involved with at least one controlled substance associated with an RFID tag (e.g. an implementation of the receiver component s528 is configured to electronically engage with the processor component s102 to receive the directive information including information regarding the particular ingestible product being involved with at least one controlled substance as determined by the processor component through electronic reading be the radio frequency identification (RFID) sensing component s414 of the RFID tag, etc.). Furthermore, the receiving information RFID electrical circuitry arrangement e1119 when activated will perform the operation o1119. In an implementation, the receiving information RFID electrical circuitry arrangement e1119, when activated performs electronically receiving the directive information including information regarding the particular ingestible product being involved with at least one controlled substance associated with an RFID tag (e.g. an implementation of the receiver component s528 is configured to electronically engage with the processor component s102 to receive the directive information including information regarding the particular ingestible product being involved with at least one controlled substance as determined by the processor component through electronic reading be the radio frequency identification (RFID) sensing component s414 of the RFID tag, etc.). In an implementation, the electronically receiving the directive information including information regarding the particular ingestible product being involved with at least one controlled substance associated with an RFID tag is carried out by electronically receiving the directive information including information regarding the particular ingestible product being involved with at least one controlled substance associated with an RFID tag (e.g. an implementation of the receiver component s528 is configured to electronically engage with the processor component s102 to receive the directive information including information regarding the particular ingestible product being involved with at least one controlled substance as determined by the processor component through electronic reading be the radio frequency identification (RFID) sensing component s414 of the RFID tag, etc.).

In one or more implementations, operation o11 includes an operation o1120 for electronically receiving the directive information including information regarding the particular ingestible product being involved with at least one controlled substance associated with a bar code. An exemplary version of the non-transitory signal bearing medium n100 is depicted as bearing one or more receiving information bar code instructions i1120 that when executed will direct performance of the operation o1120. In an implementation, the one or more receiving information bar code instructions i1120 when executed direct electronically receiving the directive information including information regarding the particular ingestible product being involved with at least one controlled substance associated with a bar code (e.g. an implementation of the receiver component s528 is configured to electronically engage with the processor component s102 to receive the directive information including information regarding the particular ingestible product being involved with at least one controlled substance as determined by the processor component through electronic reading of the bar code, etc.). Furthermore, the receiving information bar code electrical circuitry arrangement e1120 when activated will perform the operation electronically receiving the directive information including information regarding the particular ingestible product being involved with at least one controlled substance associated with a bar code. In an implementation, the receiving information bar code electrical circuitry arrangement e1120, when activated performs electronically receiving the directive information including information regarding the particular ingestible product being involved with at least one controlled substance associated with a bar code (e.g. an implementation of the receiver component s528 is configured to electronically engage with the processor component s102 to receive the directive information including information regarding the particular ingestible product being involved with at least one controlled substance as determined by the processor component through electronic reading of the bar code, etc.). In an implementation, the electronically receiving the directive information including information regarding the particular ingestible product being involved with at least one controlled substance associated with a bar code is carried out by electronically receiving the directive information including information regarding the particular ingestible product being involved with at least one controlled substance associated with a bar code (e.g. an implementation of the receiver component s528 is configured to electronically engage with the processor component s102 to receive the directive information including information regarding the particular ingestible product being involved with at least one controlled substance as determined by the processor component through electronic reading of the bar code, etc.).

Figure 33:
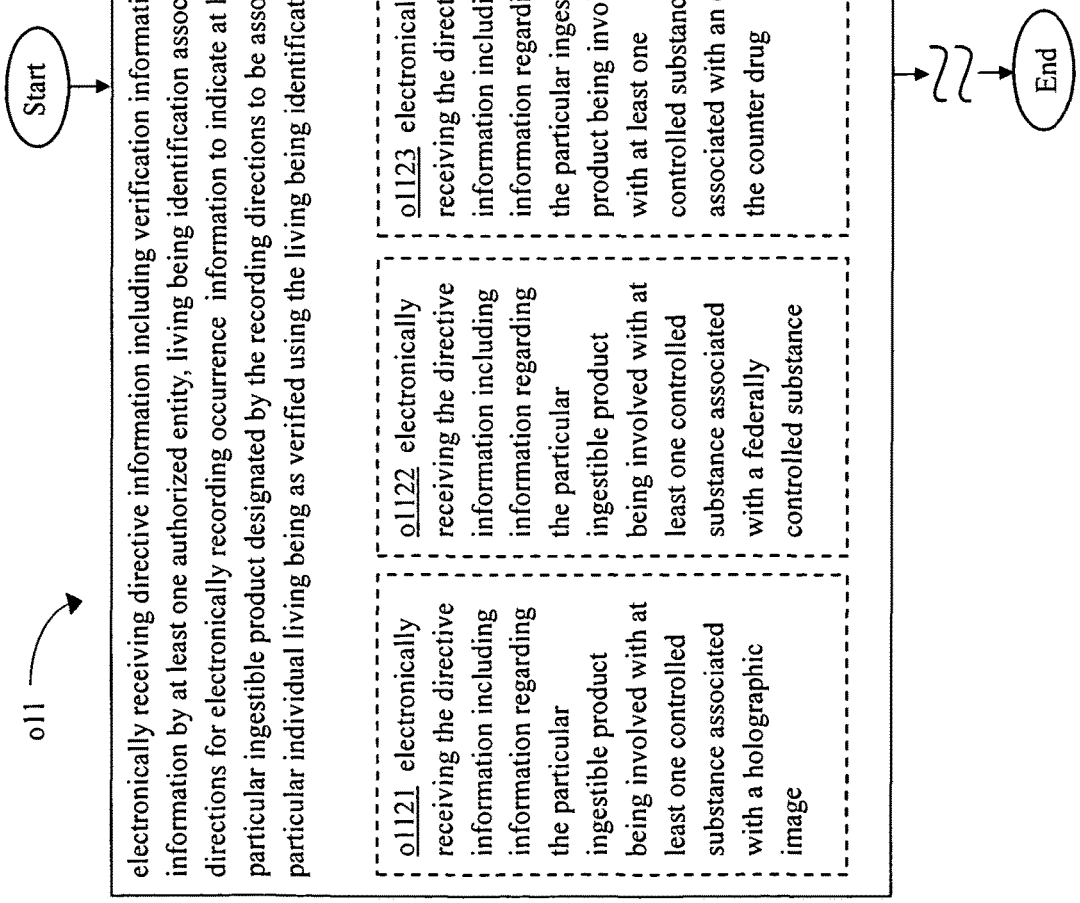
FIG. 33 is a high-level flowchart including exemplary implementations of operation O11 of FIG. 28.

In one or more implementations, as shown in FIG. 33, operation o11 includes an operation o1121 for electronically receiving the directive information including information regarding the particular ingestible product being involved with at least one controlled substance associated with a holographic image. An exemplary version of the non-transitory signal bearing medium n100 is depicted as bearing one or more receiving information holographic instructions i1121 that when executed will direct performance of the operation o1121. In an implementation, the one or more receiving information holographic instructions i1121 when executed direct electronically receiving the directive information including information regarding the particular ingestible product being involved with at least one controlled substance associated with a holographic image (e.g. an implementation of the receiver component s528 is configured to electronically engage with the processor component s102 to receive the directive information including information regarding the particular ingestible product being involved with at least one controlled substance as determined by the processor component through electronic reading of the holographic image, etc.). Furthermore, the receiving information holographic electrical circuitry arrangement e1121 when activated will perform the operation o1121. In an implementation, the receiving information holographic electrical circuitry arrangement e1121, when activated performs electronically receiving the directive information including information regarding the particular ingestible product being involved with at least one controlled substance associated with a holographic image (e.g. an implementation of the receiver component s528 is configured to electronically engage with the processor component s102 to receive the directive information including information regarding the particular ingestible product being involved with at least one controlled substance as determined by the processor component through electronic reading of the holographic image, etc.). In an implementation, the electronically receiving the directive information including information regarding the particular ingestible product being involved with at least one controlled substance associated with a holographic image is carried out by electronically receiving the directive information including information regarding the particular ingestible product being involved with at least one controlled substance associated with a holographic image (e.g. an implementation of the receiver component s528 is configured to electronically engage with the processor component s102 to receive the directive information including information regarding the particular ingestible product being involved with at least one controlled substance as determined by the processor component through electronic reading of the holographic image, etc.).

In one or more implementations, operation o11 includes an operation o1122 for electronically receiving the directive information including information regarding the particular ingestible product being involved with at least one controlled substance associated with a federally controlled substance. An exemplary version of the non-transitory signal bearing medium n100 is depicted as bearing one or more receiving information federally instructions i1122 that when executed will direct performance of the operation o1122. In an implementation, the one or more receiving information federally instructions i1122 when executed direct electronically receiving the directive information including information regarding the particular ingestible product being involved with at least one controlled substance associated with a federally controlled substance (e.g. an implementation of the receiver component s528 is configured to electronically engage with the processor component s102 to receive the directive information including information regarding the particular ingestible product being involved with at least one controlled substance as determined by the processor component to be associated with a federally controlled substance through a table lookup procedure, etc.). Furthermore, the receiving information federally electrical circuitry arrangement e1122 when activated will perform the operation o1122. In an implementation, the receiving information federally electrical circuitry arrangement e1122, when activated performs electronically receiving the directive information including information regarding the particular ingestible product being involved with at least one controlled substance associated with a federally controlled substance (e.g. an implementation of the receiver component s528 is configured to electronically engage with the processor component s102 to receive the directive information including information regarding the particular ingestible product being involved with at least one controlled substance as determined by the processor component to be associated with a federally controlled substance through a table lookup procedure, etc.). In an implementation, the electronically receiving the directive information including information regarding the particular ingestible product being involved with at least one controlled substance associated with a federally controlled substance is carried out by electronically receiving the directive information including information regarding the particular ingestible product being involved with at least one controlled substance associated with a federally controlled substance (e.g. an implementation of the receiver component s528 is configured to electronically engage with the processor component s102 to receive the directive information including information regarding the particular ingestible product being involved with at least one controlled substance as determined by the processor component to be associated with a federally controlled substance through a table lookup procedure, etc.).

In one or more implementations, operation o11 includes an operation o1123 for electronically receiving the directive information including information regarding the particular ingestible product being involved with at least one controlled substance associated with an over the counter drug. An exemplary version of the non-transitory signal bearing medium n100 is depicted as bearing one or more receiving information otc drug instructions i1123 that when executed will direct performance of the operation o1123. In an implementation, the one or more receiving information otc drug instructions i1123 when executed direct electronically receiving the directive information including information regarding the particular ingestible product being involved with at least one controlled substance associated with an over the counter drug (e.g. an implementation of the receiver component s528 is configured to electronically engage with the processor component s102 to receive the directive information including information regarding the particular ingestible product being involved with at least one controlled substance as determined by the processor component to be associated with the over the counter drug with a database query, etc.). Furthermore, the receiving information otc drug electrical circuitry arrangement e1123 when activated will perform the operation o1123. In an implementation, the receiving information otc drug electrical circuitry arrangement e1123, when activated performs electronically receiving the directive information including information regarding the particular ingestible product being involved with at least one controlled substance associated with an over the counter drug (e.g. an implementation of the receiver component s528 is configured to electronically engage with the processor component s102 to receive the directive information including information regarding the particular ingestible product being involved with at least one controlled substance as determined by the processor component to be associated with the over the counter drug with a database query, etc.). In an implementation, the electronically receiving the directive information including information regarding the particular ingestible product being involved with at least one controlled substance associated with an over the counter drug is carried out by electronically receiving the directive information including information regarding the particular ingestible product being involved with at least one controlled substance associated with an over the counter drug (e.g. an implementation of the receiver component s528 is configured to electronically engage with the processor component s102 to receive the directive information including information regarding the particular ingestible product being involved with at least one controlled substance as determined by the processor component to be associated with the over the counter drug with a database query, etc.).

In one or more implementations, operation o11 includes an operation o1124 for electronically receiving the directive information including information regarding the particular ingestible product being involved with at least one controlled substance associated with an herbal substance. An exemplary version of the non-transitory signal bearing medium n100 is depicted as bearing one or more receiving information herbal instructions i1124 that when executed will direct performance of the operation o1124. In an implementation, the one or more receiving information herbal instructions i1124 when executed direct electronically receiving the directive information including information regarding the particular ingestible product being involved with at least one controlled substance associated with an herbal substance (e.g. an implementation of the receiver component s528 is configured to electronically engage with the processor component s102 to receive the directive information including information regarding the particular ingestible product being involved with at least one controlled substance as determined by the processor component to be identifying an herbal substance, etc.). Furthermore, the receiving information herbal electrical circuitry arrangement e1124 when activated will perform the operation o1124. In an implementation, the receiving information herbal electrical circuitry arrangement e1124, when activated performs electronically receiving the directive information including information regarding the particular ingestible product being involved with at least one controlled substance associated with an herbal substance (e.g. an implementation of the receiver component s528 is configured to electronically engage with the processor component s102 to receive the directive information including information regarding the particular ingestible product being involved with at least one controlled substance as determined by the processor component to be identifying an herbal substance, etc.). In an implementation, the electronically receiving the directive information including information regarding the particular ingestible product being involved with at least one controlled substance associated with an herbal substance is carried out by electronically receiving the directive information including information regarding the particular ingestible product being involved with at least one controlled substance associated with an herbal substance (e.g. an implementation of the receiver component s528 is configured to electronically engage with the processor component s102 to receive the directive information including information regarding the particular ingestible product being involved with at least one controlled substance as determined by the processor component to be identifying an herbal substance, etc.).

In one or more implementations, operation o11 includes an operation o1125 for electronically receiving the directive information including information regarding the particular ingestible product being involved with at least one controlled substance associated with a homeopathic substance. An exemplary version of the non-transitory signal bearing medium n100 is depicted as bearing one or more receiving information homeopathic instructions i1125 that when executed will direct performance of the operation o1125. In an implementation, the one or more receiving information homeopathic instructions i1125 when executed direct electronically receiving the directive information including information regarding the particular ingestible product being involved with at least one controlled substance associated with a homeopathic substance (e.g. an implementation of the receiver component s528 is configured to electronically engage with the processor component s102 to receive the directive information including information regarding the particular ingestible product being involved with at least one controlled substance as determined by the processor component to be identifying a homeopathic substance, etc.). Furthermore, the receiving information homeopathic electrical circuitry arrangement e1125 when activated will perform the operation o1125. In an implementation, the receiving information homeopathic electrical circuitry arrangement e1125, when activated performs electronically receiving the directive information including information regarding the particular ingestible product being involved with at least one controlled substance associated with a homeopathic substance (e.g. an implementation of the receiver component s528 is configured to electronically engage with the processor component s102 to receive the directive information including information regarding the particular ingestible product being involved with at least one controlled substance as determined by the processor component to be identifying a homeopathic substance, etc.). In an implementation, the electronically receiving the directive information including information regarding the particular ingestible product being involved with at least one controlled substance associated with a homeopathic substance is carried out by electronically receiving the directive information including information regarding the particular ingestible product being involved with at least one controlled substance associated with a homeopathic substance (e.g. an implementation of the receiver component s528 is configured to electronically engage with the processor component s102 to receive the directive information including information regarding the particular ingestible product being involved with at least one controlled substance as determined by the processor component to be identifying a homeopathic substance, etc.).

Figure 34:
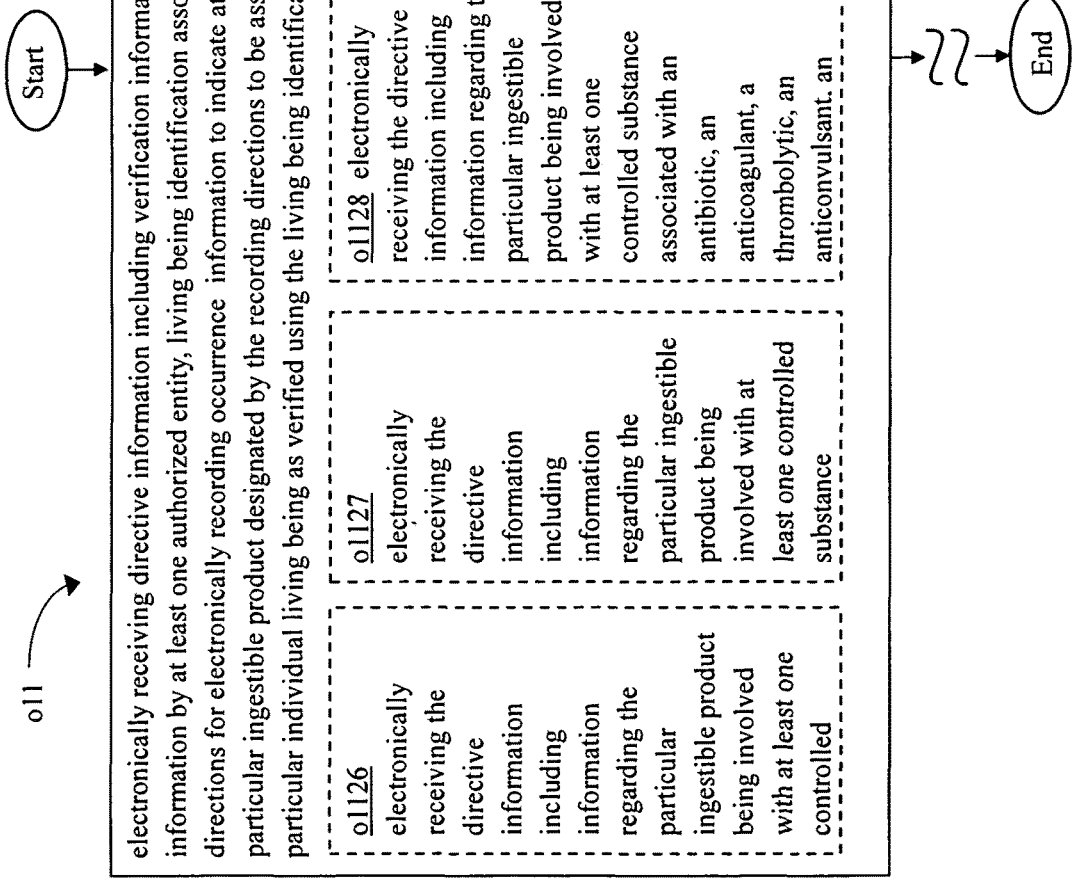
FIG. 34 is a high-level flowchart including exemplary implementations of operation O11 of FIG. 28.

In one or more implementations, as shown in FIG. 34, operation o11 includes an operation o1126 for electronically receiving the directive information including information regarding the particular ingestible product being involved with at least one controlled substance associated with a nutritional substance. An exemplary version of the non-transitory signal bearing medium n100 is depicted as bearing one or more receiving information nutritional instructions i1126 that when executed will direct performance of the operation o1126. In an implementation, the one or more receiving information nutritional instructions i1126 when executed direct electronically receiving the directive information including information regarding the particular ingestible product being involved with at least one controlled substance associated with a nutritional substance (e.g. an implementation of the receiver component s528 is configured to electronically engage with the processor component s102 to receive the directive information including information regarding the particular ingestible product being involved with at least one controlled substance as determined by the processor component to be identifying a nutritional substance, etc.). Furthermore, the receiving information nutritional electrical circuitry arrangement e1126 when activated will perform the operation o1126. In an implementation, the receiving information nutritional electrical circuitry arrangement e1126, when activated performs electronically receiving the directive information including information regarding the particular ingestible product being involved with at least one controlled substance associated with a nutritional substance (e.g. an implementation of the receiver component s528 is configured to electronically engage with the processor component s102 to receive the directive information including information regarding the particular ingestible product being involved with at least one controlled substance as determined by the processor component to be identifying a nutritional substance, etc.). In an implementation, the electronically receiving the directive information including information regarding the particular ingestible product being involved with at least one controlled substance associated with a nutritional substance is carried out by electronically receiving the directive information including information regarding the particular ingestible product being involved with at least one controlled substance associated with a nutritional substance (e.g. an implementation of the receiver component s528 is configured to electronically engage with the processor component s102 to receive the directive information including information regarding the particular ingestible product being involved with at least one controlled substance as determined by the processor component to be identifying a nutritional substance, etc.).

In one or more implementations, operation o11 includes an operation o1127 for electronically receiving the directive information including information regarding the particular ingestible product being involved with at least one controlled substance associated with an analgesic, an antacid, an antiarrhythmic, an analgesic, an antacid, an antiarrhythmic, or an antibacterial. An exemplary version of the non-transitory signal bearing medium n100 is depicted as bearing one or more receiving information first medications instructions i1127 that when executed will direct performance of the operation o1127. In an implementation, the one or more receiving information first medications instructions i1127 when executed direct electronically receiving the directive information including information regarding the particular ingestible product being involved with at least one controlled substance associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including information regarding the particular ingestible product being involved with at least one controlled substance as determined by the processor component to be identifying an analgesic, an antacid, an antiarrhythmic, an analgesic, an antacid, an antiarrhythmic, or an antibacterial, etc.)l. Furthermore, the receiving information first medications electrical circuitry arrangement e1127 when activated will perform the operation o1127. In an implementation, the receiving information first medications electrical circuitry arrangement e1127, when activated performs electronically receiving the directive information including information regarding the particular ingestible product being involved with at least one controlled substance associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including information regarding the particular ingestible product being involved with at least one controlled substance as determined by the processor component to be identifying an analgesic, an antacid, an antiarrhythmic, an analgesic, an antacid, an antiarrhythmic, or an antibacterial, etc.)l. In an implementation, the electronically receiving the directive information including information regarding the particular ingestible product being involved with at least one controlled substance associated with an analgesic, an antacid, an antiarrhythmic, an analgesic, an antacid, an antiarrhythmic, or an antibacterial is carried out by electronically receiving the directive information including information regarding the particular ingestible product being involved with at least one controlled substance associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including information regarding the particular ingestible product being involved with at least one controlled substance as determined by the processor component to be identifying an analgesic, an antacid, an antiarrhythmic, an analgesic, an antacid, an antiarrhythmic, or an antibacterial, etc.)

In one or more implementations, operation o11 includes an operation o1128 for electronically receiving the directive information including information regarding the particular ingestible product being involved with at least one controlled substance associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, or an antineoplastic. An exemplary version of the non-transitory signal bearing medium n100 is depicted as bearing one or more receiving information second medications instructions i1128 that when executed will direct performance of the operation o1128. In an implementation, the one or more receiving information second medications instructions i1128 when executed direct electronically receiving the directive information including information regarding the particular ingestible product being involved with at least one controlled substance associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including information regarding the particular ingestible product being involved with at least one controlled substance as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). Furthermore, the receiving information second medications electrical circuitry arrangement e1128 when activated will perform the operation o1128. In an implementation, the receiving information second medications electrical circuitry arrangement e1128, when activated performs electronically receiving the directive information including information regarding the particular ingestible product being involved with at least one controlled substance associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including information regarding the particular ingestible product being involved with at least one controlled substance as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). In an implementation, the electronically receiving the directive information including information regarding the particular ingestible product being involved with at least one controlled substance associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, or an antineoplastic is carried out by electronically receiving the directive information including information regarding the particular ingestible product being involved with at least one controlled substance associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including information regarding the particular ingestible product being involved with at least one controlled substance as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.).

In one or more implementations, operation o11 includes an operation o1129 for electronically receiving the directive information including information regarding the particular ingestible product being involved with at least one controlled substance associated with an antipyretic, an antiviral, an anti-ulcer agent, an antidyspeptic, an antacid, a beta-blocker, a bronchodilator, a cold treatment, or a corticosteroid. An exemplary version of the non-transitory signal bearing medium n100 is depicted as bearing one or more receiving information third medications instructions i1129 that when executed will direct performance of the operation o1129. In an implementation, the one or more receiving information third medications instructions i1129 when executed direct electronically receiving the directive information including information regarding the particular ingestible product being involved with at least one controlled substance associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including information regarding the particular ingestible product being involved with at least one controlled substance as determined by the processor component to be identifying an antipyretic, an antiviral, an anti-ulcer agent, an antidyspeptic, an antacid, a beta-blocker, a bronchodilator, a cold treatment, or a corticosteroid, etc.). Furthermore, the receiving information third medications electrical circuitry arrangement e1129 when activated will perform the operation o1129. In an implementation, the receiving information third medications electrical circuitry arrangement e1129, when activated performs electronically receiving the directive information including information regarding the particular ingestible product being involved with at least one controlled substance associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including information regarding the particular ingestible product being involved with at least one controlled substance as determined by the processor component to be identifying an antipyretic, an antiviral, an anti-ulcer agent, an antidyspeptic, an antacid, a beta-blocker, a bronchodilator, a cold treatment, or a corticosteroid, etc.). In an implementation, the electronically receiving the directive information including information regarding the particular ingestible product being involved with at least one controlled substance associated with an antipyretic, an antiviral, an anti-ulcer agent, an antidyspeptic, an antacid, a beta-blocker, a bronchodilator, a cold treatment, or a corticosteroid is carried out by electronically receiving the directive information including information regarding the particular ingestible product being involved with at least one controlled substance associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including information regarding the particular ingestible product being involved with at least one controlled substance as determined by the processor component to be identifying an antipyretic, an antiviral, an anti-ulcer agent, an antidyspeptic, an antacid, a beta-blocker, a bronchodilator, a cold treatment, or a corticosteroid, etc.).

In one or more implementations, operation o11 includes an operation o1130 for electronically receiving the directive information including information regarding the particular ingestible product being involved with at least one controlled substance associated with a cough suppressant, an antitussive, a cytotoxic agent, a decongestant, a diuretic, or an expectorant. An exemplary version of the non-transitory signal bearing medium n100 is depicted as bearing one or more receiving information fourth medications instructions i1130 that when executed will direct performance of the operation o1130. In an implementation, the one or more receiving information fourth medications instructions i1130 when executed direct electronically receiving the directive information including information regarding the particular ingestible product being involved with at least one controlled substance associated with a cough suppressant, an antitussive, a cytotoxic agent, a decongestant, a diuretic, or an expectorant (e.g. an implementation of the receiver component s528 is configured to electronically engage with the processor component s102 to receive the directive information including information regarding the particular ingestible product being involved with at least one controlled substance as determined by the processor component to be identifying a cough suppressant, an antitussive, a cytotoxic agent, a decongestant, a diuretic, or an expectorant, etc.). Furthermore, the receiving information fourth medications electrical circuitry arrangement e1130 when activated will perform the operation o1130. In an implementation, the receiving information fourth medications electrical circuitry arrangement e1130, when activated performs electronically receiving the directive information including information regarding the particular ingestible product being involved with at least one controlled substance associated with a cough suppressant, an antitussive, a cytotoxic agent, a decongestant, a diuretic, or an expectorant (e.g. an implementation of the receiver component s528 is configured to electronically engage with the processor component s102 to receive the directive information including information regarding the particular ingestible product being involved with at least one controlled substance as determined by the processor component to be identifying a cough suppressant, an antitussive, a cytotoxic agent, a decongestant, a diuretic, or an expectorant, etc.). In an implementation, the electronically receiving the directive information including information regarding the particular ingestible product being involved with at least one controlled substance associated with a cough suppressant, an antitussive, a cytotoxic agent, a decongestant, a diuretic, or an expectorant is carried out by electronically receiving the directive information including information regarding the particular ingestible product being involved with at least one controlled substance associated with a cough suppressant, an antitussive, a cytotoxic agent, a decongestant, a diuretic, or an expectorant (e.g. an implementation of the receiver component s528 is configured to electronically engage with the processor component s102 to receive the directive information including information regarding the particular ingestible product being involved with at least one controlled substance as determined by the processor component to be identifying a cough suppressant, an antitussive, a cytotoxic agent, a decongestant, a diuretic, or an expectorant, etc.).

Figure 35:
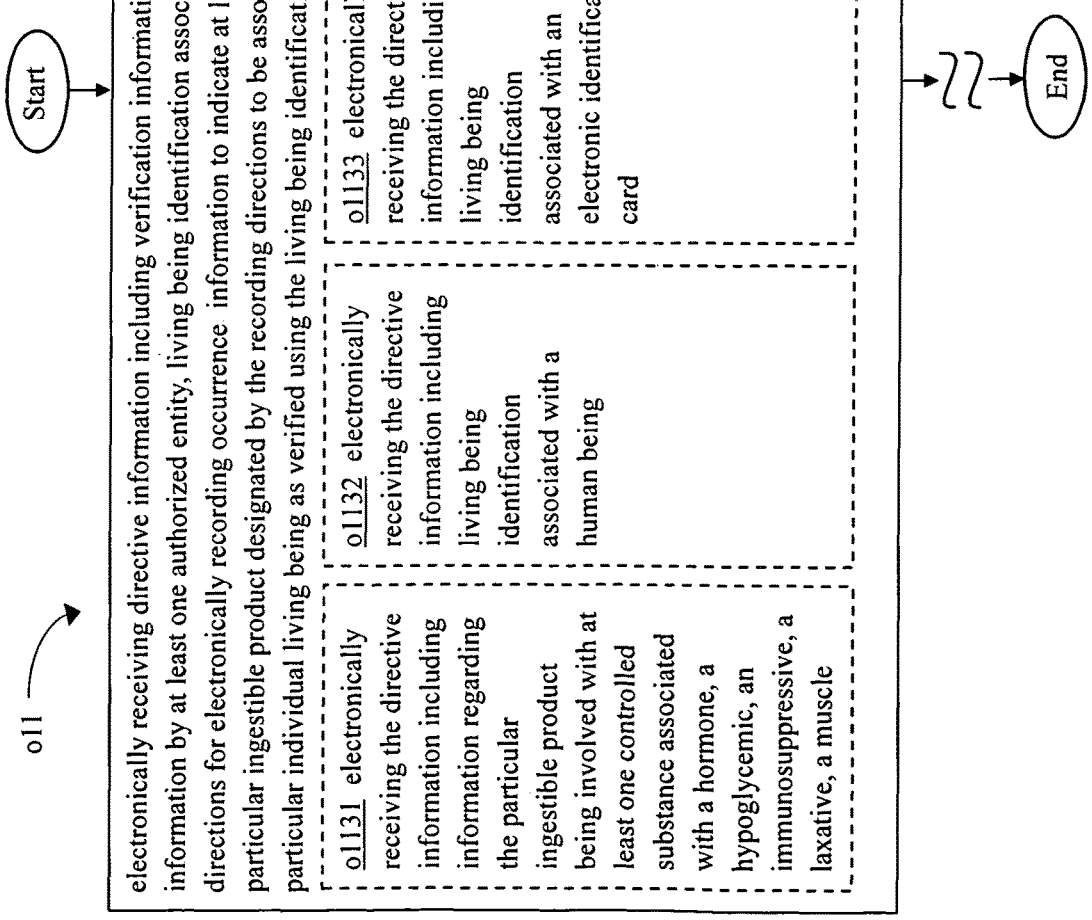
FIG. 35 is a high-level flowchart including exemplary implementations of operation O11 of FIG. 28.

In one or more implementations, as shown in FIG. 35, operation o11 includes an operation o1131 for electronically receiving the directive information including information regarding the particular ingestible product being involved with at least one controlled substance associated with a hormone, a hypoglycemic, an immunosuppressive, a laxative, a muscle relaxant, a sedative, a tranquilizer, an appetite modulator, or a vitamin. An exemplary version of the non-transitory signal bearing medium n100 is depicted as bearing one or more receiving fifth medications instructions i1131 that when executed will direct performance of the operation o1131. In an implementation, the one or more receiving fifth medications instructions i1131 when executed direct electronically receiving the directive information including information regarding the particular ingestible product being involved with at least one controlled substance associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including information regarding the particular ingestible product being involved with at least one controlled substance as determined by the processor component to be identifying a hormone, a hypoglycemic, an immunosuppressive, a laxative, a muscle relaxant, a sedative, a tranquilizer, an appetite modulator, a vitamin, or a combination thereof, etc.). Furthermore, the receiving fifth medications electrical circuitry arrangement e1131 when activated will perform the operation o1131. In an implementation, the receiving fifth medications electrical circuitry arrangement e1131, when activated performs electronically receiving the directive information including information regarding the particular ingestible product being involved with at least one controlled substance associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including information regarding the particular ingestible product being involved with at least one controlled substance as determined by the processor component to be identifying a hormone, a hypoglycemic, an immunosuppressive, a laxative, a muscle relaxant, a sedative, a tranquilizer, an appetite modulator, a vitamin, or a combination thereof, etc.). In an implementation, the electronically receiving the directive information including information regarding the particular ingestible product being involved with at least one controlled substance associated with a hormone, a hypoglycemic, an immunosuppressive, a laxative, a muscle relaxant, a sedative, a tranquilizer, an appetite modulator, or a vitamin is carried out by electronically receiving the directive information including information regarding the particular ingestible product being involved with at least one controlled substance associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including information regarding the particular ingestible product being involved with at least one controlled substance as determined by the processor component to be identifying a hormone, a hypoglycemic, an immunosuppressive, a laxative, a muscle relaxant, a sedative, a tranquilizer, an appetite modulator, a vitamin, or a combination thereof, etc.).

In one or more implementations, operation o11 includes an operation o1132 for electronically receiving the directive information including living being identification associated with a human being. An exemplary version of the non-transitory signal bearing medium n100 is depicted as bearing one or more receiving information human instructions i1132 that when executed will direct performance of the operation o1132. In an implementation, the one or more receiving information human instructions i1132 when executed direct electronically receiving the directive information including living being identification associated with a human being (e.g. an implementation of the receiver component s528 is configured to electronically engage with the processor component s102 to receive the directive information including living being identification as determined by the processor component to be identifying a human being, etc.). Furthermore, the receiving information human electrical circuitry arrangement e1132 when activated will perform the operation o1132. In an implementation, the receiving information human electrical circuitry arrangement e1132, when activated performs electronically receiving the directive information including living being identification associated with a human being (e.g. an implementation of the receiver component s528 is configured to electronically engage with the processor component s102 to receive the directive information including living being identification as determined by the processor component to be identifying a human being, etc.). In an implementation, the electronically receiving the directive information including living being identification associated with a human being is carried out by electronically receiving the directive information including living being identification associated with a human being (e.g. an implementation of the receiver component s528 is configured to electronically engage with the processor component s102 to receive the directive information including living being identification as determined by the processor component to be identifying a human being, etc.).

In one or more implementations, operation o11 includes an operation o1133 for electronically receiving the directive information including living being identification associated with an electronic identification card. An exemplary version of the non-transitory signal bearing medium n100 is depicted as bearing one or more receiving information ID card instructions i1133 that when executed will direct performance of the operation o1133. In an implementation, the one or more receiving information ID card instructions i1133 when executed direct electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.). Furthermore, the receiving information ID card electrical circuitry arrangement e1133 when activated will perform the operation o1133. In an implementation, the receiving information ID card electrical circuitry arrangement e1133, when activated performs electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.). In an implementation, the electronically receiving the directive information including living being identification associated with an electronic identification card is carried out by electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.).

In one or more implementations, operation o11 includes an operation o1134 for electronically receiving the directive information including living being identification associated with an electronic iris scan. An exemplary version of the non-transitory signal bearing medium n100 is depicted as bearing one or more receiving information iris scan instructions i1134 that when executed will direct performance of the operation o1134. In an implementation, the one or more receiving information iris scan instructions i1134 when executed direct electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.). Furthermore, the receiving information iris scan electrical circuitry arrangement e1134 when activated will perform the operation o1134. In an implementation, the receiving information iris scan electrical circuitry arrangement e1134, when activated performs electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.). In an implementation, the electronically receiving the directive information including living being identification associated with an electronic iris scan is carried out by electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.).

In one or more implementations, operation o11 includes an operation o1135 for electronically receiving the directive information including living being identification associated with an electronic voice print. An exemplary version of the non-transitory signal bearing medium n100 is depicted as bearing one or more receiving information voice instructions i1135 that when executed will direct performance of the operation o1135. In an implementation, the one or more receiving information voice instructions i1135 when executed direct electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.). Furthermore, the receiving information voice electrical circuitry arrangement e1135 when activated will perform the operation o1135. In an implementation, the receiving information voice electrical circuitry arrangement e1135, when activated performs electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.). In an implementation, the electronically receiving the directive information including living being identification associated with an electronic voice print is carried out by electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.).

Figure 36:
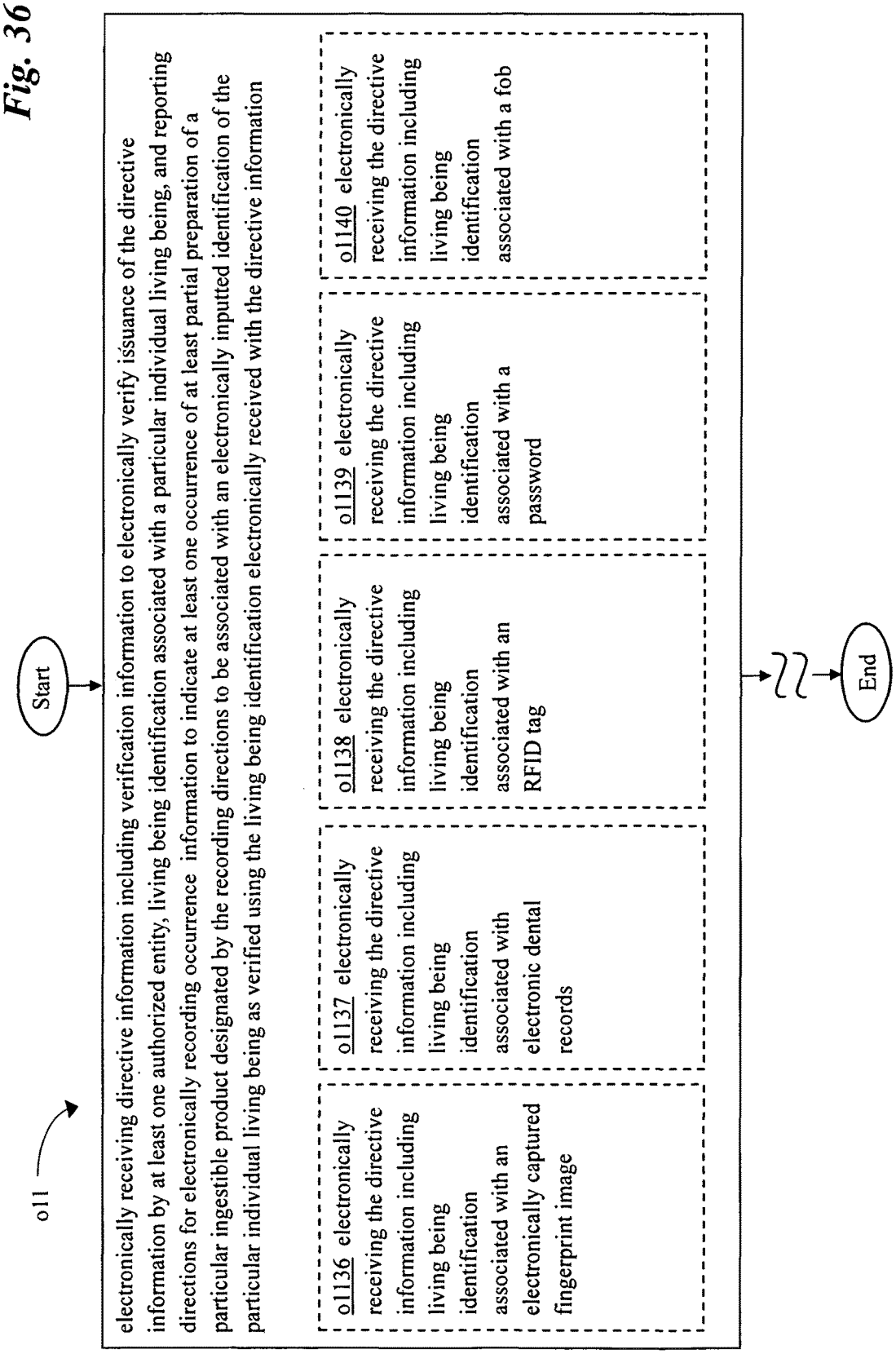
FIG. 36 is a high-level flowchart including exemplary implementations of operation O11 of FIG. 28.

In one or more implementations, as shown in FIG. 36, operation o11 includes an operation o1136 for electronically receiving the directive information including living being identification associated with an electronically captured fingerprint image. An exemplary version of the non-transitory signal bearing medium n100 is depicted as bearing one or more receiving information fingerprint instructions i1136 that when executed will direct performance of the operation o1136. In an implementation, the one or more receiving information fingerprint instructions i1136 when executed direct electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.). Furthermore, the receiving information fingerprint electrical circuitry arrangement e1136 when activated will perform the operation o1136. In an implementation, the receiving information fingerprint electrical circuitry arrangement e1136, when activated performs electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.). In an implementation, the electronically receiving the directive information including living being identification associated with an electronically captured fingerprint image is carried out by electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.).

In one or more implementations, operation o11 includes an operation o1137 for electronically receiving the directive information including living being identification associated with electronic dental records. An exemplary version of the non-transitory signal bearing medium n100 is depicted as bearing one or more receiving information dental instructions i1137 that when executed will direct performance of the operation o1137. In an implementation, the one or more receiving information dental instructions i1137 when executed direct electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.). Furthermore, the receiving information dental electrical circuitry arrangement e1137 when activated will perform the operation o1137. In an implementation, the receiving information dental electrical circuitry arrangement e1137, when activated performs electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.). In an implementation, the electronically receiving the directive information including living being identification associated with electronic dental records is carried out by electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.).

In one or more implementations, operation o11 includes an operation o1138 for electronically receiving the directive information including living being identification associated with an RFID tag. An exemplary version of the non-transitory signal bearing medium n100 is depicted as bearing one or more receiving information RFID instructions i1138 that when executed will direct performance of the operation o1138. In an implementation, the one or more receiving information RFID instructions i1138 when executed direct electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.). Furthermore, the receiving information RFID electrical circuitry arrangement e1138 when activated will perform the operation o1138. In an implementation, the receiving information RFID electrical circuitry arrangement e1138, when activated performs electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.). In an implementation, the electronically receiving the directive information including living being identification associated with an RFID tag is carried out by electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.).

In one or more implementations, operation o11 includes an operation o1139 for electronically receiving the directive information including living being identification associated with a password. An exemplary version of the non-transitory signal bearing medium n100 is depicted as bearing one or more receiving information password instructions i1139 that when executed will direct performance of the operation o1139. In an implementation, the one or more receiving information password instructions i1139 when executed direct electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.). Furthermore, the receiving information password electrical circuitry arrangement e1139 when activated will perform the operation o1139. In an implementation, the receiving information password electrical circuitry arrangement e1139, when activated performs electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.). In an implementation, the electronically receiving the directive information including living being identification associated with a password is carried out by electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.).

In one or more implementations, operation o11 includes an operation o1140 for electronically receiving the directive information including living being identification associated with a fob. An exemplary version of the non-transitory signal bearing medium n100 is depicted as bearing one or more receiving information fob instructions i1140 that when executed will direct performance of the operation o1140. In an implementation, the one or more receiving information fob instructions i1140 when executed direct electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.). Furthermore, the receiving information fob electrical circuitry arrangement e1140 when activated will perform the operation o1140. In an implementation, the receiving information fob electrical circuitry arrangement e1140, when activated performs electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.). In an implementation, the electronically receiving the directive information including living being identification associated with a fob is carried out by electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.).

Figure 37:
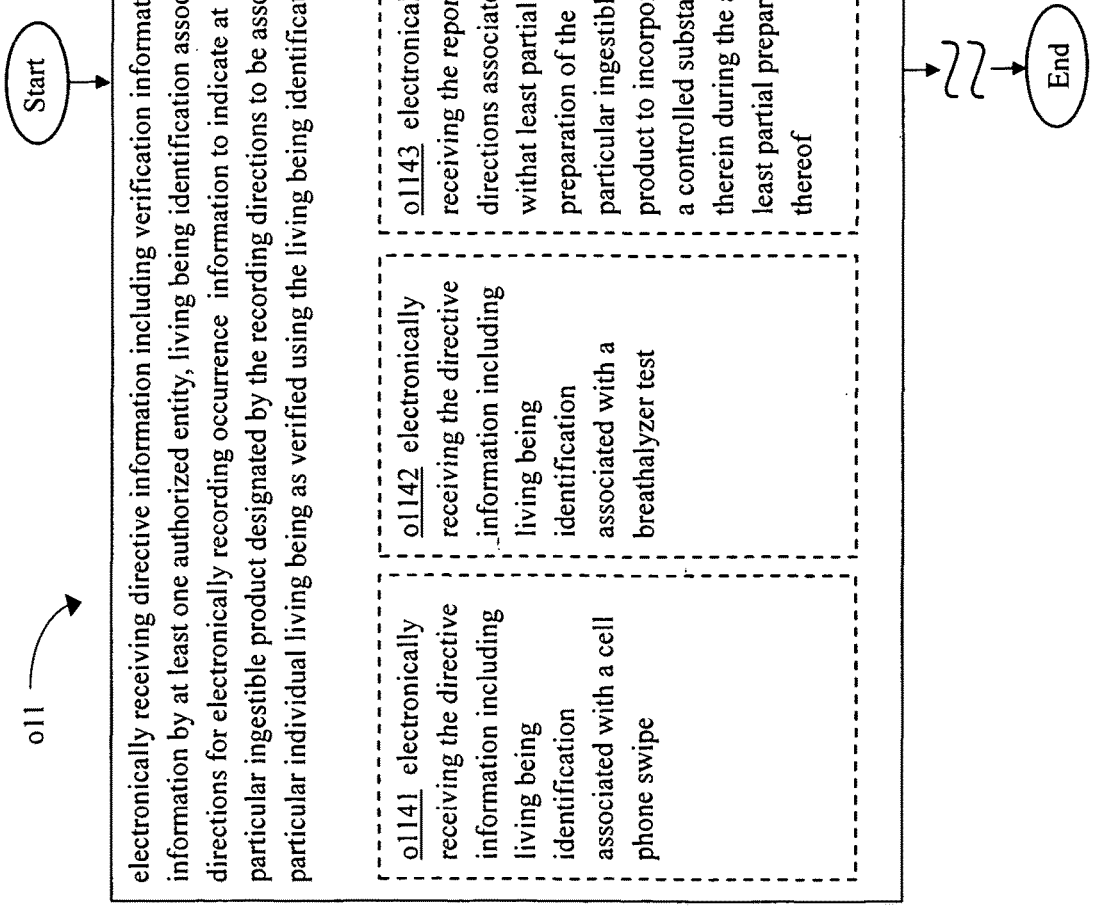
FIG. 37 is a high-level flowchart including exemplary implementations of operation O11 of FIG. 28.

In one or more implementations, as shown in FIG. 37, operation o11 includes an operation o1141 for electronically receiving the directive information including living being identification associated with a cell phone swipe. An exemplary version of the non-transitory signal bearing medium n100 is depicted as bearing one or more receiving information cell phone instructions i1141 that when executed will direct performance of the operation o1141. In an implementation, the one or more receiving information cell phone instructions i1141 when executed direct electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.). Furthermore, the receiving information cell phone electrical circuitry arrangement e1141 when activated will perform the operation o1141. In an implementation, the receiving information cell phone electrical circuitry arrangement e1141, when activated performs electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.). In an implementation, the electronically receiving the directive information including living being identification associated with a cell phone swipe is carried out by electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.).

In one or more implementations, operation o11 includes an operation o1142 for electronically receiving the directive information including living being identification associated with a breathalyzer test. An exemplary version of the non-transitory signal bearing medium n100 is depicted as bearing one or more receiving information breathalyzer instructions i1142 that when executed will direct performance of the operation o1142. In an implementation, the one or more receiving information breathalyzer instructions i1142 when executed direct electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.). Furthermore, the receiving information breathalyzer electrical circuitry arrangement e1142 when activated will perform the operation o1142. In an implementation, the receiving information breathalyzer electrical circuitry arrangement e1142, when activated performs electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.). In an implementation, the electronically receiving the directive information including living being identification associated with a breathalyzer test is carried out by electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.).

In one or more implementations, operation o11 includes an operation o1143 for electronically receiving the reporting directions associated with at least partial preparation of the particular ingestible product to incorporate a controlled substance therein during the at least partial preparation thereof. An exemplary version of the non-transitory signal bearing medium n100 is depicted as bearing one or more receiving information incorporate instructions i1143 that when executed will direct performance of the operation o1143. In an implementation, the one or more receiving information incorporate instructions i1143 when executed direct electronically receiving the reporting directions associated with at least partial preparation of the particular ingestible product to incorporate a controlled substance therein during the at least partial preparation thereof (e.g. an implementation of the receiver component s528 is configured to electronically receive the reporting directions involving engagement with the processor component s102 to direct the material processing subsystem s700 to at least partially prepare the particular ingestible product such as a sandwich to include the controlled substance as an amino acid incorporated into the sandwich, etc.). Furthermore, the receiving information incorporate electrical circuitry arrangement e1143 when activated will perform the operation o1143. In an implementation, the receiving information incorporate electrical circuitry arrangement e1143, when activated performs electronically receiving the reporting directions associated with at least partial preparation of the particular ingestible product to incorporate a controlled substance therein during the at least partial preparation thereof (e.g. an implementation of the receiver component s528 is configured to electronically receive the reporting directions involving engagement with the processor component s102 to direct the material processing subsystem s700 to at least partially prepare the particular ingestible product such as a sandwich to include the controlled substance as an amino acid incorporated into the sandwich, etc.). In an implementation, the electronically receiving the reporting directions associated with at least partial preparation of the particular ingestible product to incorporate a controlled substance therein during the at least partial preparation thereof is carried out by electronically receiving the reporting directions associated with at least partial preparation of the particular ingestible product to incorporate a controlled substance therein during the at least partial preparation thereof (e.g. an implementation of the receiver component s528 is configured to electronically receive the reporting directions involving engagement with the processor component s102 to direct the material processing subsystem s700 to at least partially prepare the particular ingestible product such as a sandwich to include the controlled substance as an amino acid incorporated into the sandwich, etc.).

In one or more implementations, operation o11 includes an operation o1144 for electronically receiving the reporting directions associated with at least partial preparation of the particular ingestible product to be ingested concurrently with ingestion of a controlled substance. An exemplary version of the non-transitory signal bearing medium n100 is depicted as bearing one or more receiving information concurrent instructions i1144 that when executed will direct performance of the operation o1144. In an implementation, the one or more receiving information concurrent instructions i1144 when executed direct electronically receiving the reporting directions associated with at least partial preparation of the particular ingestible product to be ingested concurrently with ingestion of a controlled substance (e.g. an implementation of the receiver component s528 is configured to electronically receive the reporting directions involving engagement with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.). Furthermore, the receiving information concurrent electrical circuitry arrangement e1144 when activated will perform the operation o1144. In an implementation, the receiving information concurrent electrical circuitry arrangement e1144, when activated performs electronically receiving the reporting directions associated with at least partial preparation of the particular ingestible product to be ingested concurrently with ingestion of a controlled substance (e.g. an implementation of the receiver component s528 is configured to electronically receive the reporting directions involving engagement with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.). In an implementation, the electronically receiving the reporting directions associated with at least partial preparation of the particular ingestible product to be ingested concurrently with ingestion of a controlled substance is carried out by electronically receiving the reporting directions associated with at least partial preparation of the particular ingestible product to be ingested concurrently with ingestion of a controlled substance (e.g. an implementation of the receiver component s528 is configured to electronically receive the reporting directions involving engagement with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.).

In one or more implementations, operation o11 includes an operation o1145 for electronically receiving the reporting directions associated with at least partial preparation of the particular ingestible product to be swallowed. An exemplary version of the non-transitory signal bearing medium n100 is depicted as bearing one or more receiving information swallow instructions i1145 that when executed will direct performance of the operation o1145. In an implementation, the one or more receiving information swallow instructions i1145 when executed direct electronically receiving the reporting directions associated with at least partial preparation of the particular ingestible product to be swallowed (e.g., an implementation of the receiver component s528 is configured to electronically receive the reporting directions associated with engagement with the processor component s102 to direct the material processing subsystem s700 to at least partially prepare the particular ingestible product to be swallowed such as a snack bar, etc.). Furthermore, the receiving information swallow electrical circuitry arrangement e1145 when activated will perform the operation o1145. In an implementation, the receiving information swallow electrical circuitry arrangement e1145, when activated performs electronically receiving the reporting directions associated with at least partial preparation of the particular ingestible product to be swallowed (e.g., an implementation of the receiver component s528 is configured to electronically receive the reporting directions associated with engagement with the processor component s102 to direct the material processing subsystem s700 to at least partially prepare the particular ingestible product to be swallowed such as a snack bar, etc.). In an implementation, the electronically receiving the reporting directions associated with at least partial preparation of the particular ingestible product to be swallowed is carried out by electronically receiving the reporting directions associated with at least partial preparation of the particular ingestible product to be swallowed (e.g., an implementation of the receiver component s528 is configured to electronically receive the reporting directions associated with engagement with the processor component s102 to direct the material processing subsystem s700 to at least partially prepare the particular ingestible product to be swallowed such as a snack bar, etc.).

Figure 38:
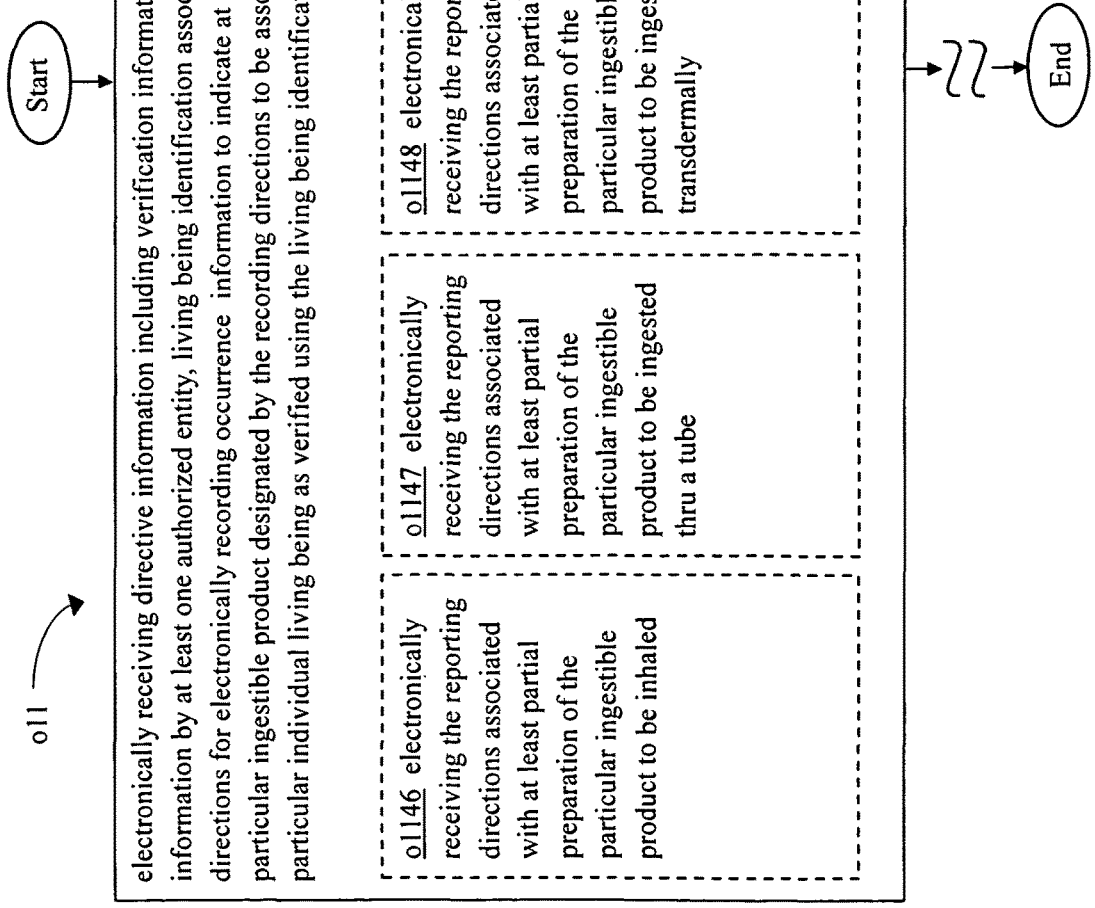
FIG. 38 is a high-level flowchart including exemplary implementations of operation O11 of FIG. 28.

In one or more implementations, as shown in FIG. 38, operation o11 includes an operation o1146 for electronically receiving the reporting directions associated with at least partial preparation of the particular ingestible product to be inhaled. An exemplary version of the non-transitory signal bearing medium n100 is depicted as bearing one or more receiving information inhaled instructions i1146 that when executed will direct performance of the operation o1146. In an implementation, the one or more receiving information inhaled instructions i1146 when executed direct electronically receiving the reporting directions associated with at least partial preparation of the particular ingestible product to be inhaled (e.g. an implementation of the receiver component s528 is configured to electronically receive the reporting directions involving engagement with the processor component s102 to direct the material processing subsystem s700 to at least partially prepare the particular ingestible product to be swallowed such as a snack bar, etc.). Furthermore, the receiving information inhaled electrical circuitry arrangement e1146 when activated will perform the operation o1146. In an implementation, the receiving information inhaled electrical circuitry arrangement e1146, when activated performs electronically receiving the reporting directions associated with at least partial preparation of the particular ingestible product to be inhaled (e.g. an implementation of the receiver component s528 is configured to electronically receive the reporting directions involving engagement with the processor component s102 to direct the material processing subsystem s700 to at least partially prepare the particular ingestible product to be swallowed such as a snack bar, etc.). In an implementation, the electronically receiving the reporting directions associated with at least partial preparation of the particular ingestible product to be inhaled is carried out by electronically receiving the reporting directions associated with at least partial preparation of the particular ingestible product to be inhaled (e.g. an implementation of the receiver component s528 is configured to electronically receive the reporting directions involving engagement with the processor component s102 to direct the material processing subsystem s700 to at least partially prepare the particular ingestible product to be swallowed such as a snack bar, etc.).

In one or more implementations, operation o11 includes an operation o1147 for electronically receiving the reporting directions associated with at least partial preparation of the particular ingestible product to be ingested thru a tube. An exemplary version of the non-transitory signal bearing medium n100 is depicted as bearing one or more receiving information tube instructions i1147 that when executed will direct performance of the operation o1147. In an implementation, the one or more receiving information tube instructions i1147 when executed direct electronically receiving the reporting directions associated with at least partial preparation of the particular ingestible product to be ingested thru a tube (e.g., an implementation of the receiver component s528 is configured to electronically receive the reporting directions involving engagement with the processor component s102 to direct the material processing subsystem s700 to at least partially prepare the particular ingestible product to be ingested through a tube such as a liquid meal replacement, etc.). Furthermore, the receiving information tube electrical circuitry arrangement e1147 when activated will perform the operation o1147. In an implementation, the receiving information tube electrical circuitry arrangement e1147, when activated performs electronically receiving the reporting directions associated with at least partial preparation of the particular ingestible product to be ingested thru a tube (e.g., an implementation of the receiver component s528 is configured to electronically receive the reporting directions involving engagement with the processor component s102 to direct the material processing subsystem s700 to at least partially prepare the particular ingestible product to be ingested through a tube such as a liquid meal replacement, etc.). In an implementation, the electronically receiving the reporting directions associated with at least partial preparation of the particular ingestible product to be ingested thru a tube is carried out by electronically receiving the reporting directions associated with at least partial preparation of the particular ingestible product to be ingested thru a tube (e.g., an implementation of the receiver component s528 is configured to electronically receive the reporting directions involving engagement with the processor component s102 to direct the material processing subsystem s700 to at least partially prepare the particular ingestible product to be ingested through a tube such as a liquid meal replacement, etc.).

In one or more implementations, operation o11 includes an operation o1148 for electronically receiving the reporting directions associated with at least partial preparation of the particular ingestible product to be ingested transdermally. An exemplary version of the non-transitory signal bearing medium n100 is depicted as bearing one or more receiving information transdermal instructions i1148 that when executed will direct performance of the operation o1148. In an implementation, the one or more receiving information transdermal instructions i1148 when executed direct electronically receiving the reporting directions including directions for at least partial preparation of the particular ingestible product to be ingested transdermally (e.g. an implementation of the receiver component s528 is configured to electronically receive the reporting directions and involving engagement with the processor component s102 to direct the material processing subsystem s700 to at least partially prepare the particular ingestible product to be ingested transdermally such as a cream, etc.). Furthermore, the receiving information transdermal electrical circuitry arrangement e1148 when activated will perform the operation o1148. In an implementation, the receiving information transdermal electrical circuitry arrangement e1148, when activated performs electronically receiving the reporting directions including directions for at least partial preparation of the particular ingestible product to be ingested transdermally (e.g. an implementation of the receiver component s528 is configured to electronically receive the reporting directions and involving engagement with the processor component s102 to direct the material processing subsystem s700 to at least partially prepare the particular ingestible product to be ingested transdermally such as a cream, etc.). In an implementation, the electronically receiving the reporting directions associated with at least partial preparation of the particular ingestible product to be ingested transdermally is carried out by electronically receiving the reporting directions including directions for at least partial preparation of the particular ingestible product to be ingested transdermally (e.g. an implementation of the receiver component s528 is configured to electronically receive the reporting directions and involving engagement with the processor component s102 to direct the material processing subsystem s700 to at least partially prepare the particular ingestible product to be ingested transdermally such as a cream, etc.).

In one or more implementations, operation o11 includes an operation o1149 for electronically receiving the reporting directions associated with at least partial preparation of the particular ingestible product to be used in a capsule form. An exemplary version of the non-transitory signal bearing medium n100 is depicted as bearing one or more receiving information capsule instructions i1149 that when executed will direct performance of the operation o1149. In an implementation, the one or more receiving information capsule instructions i1149 when executed direct electronically receiving the reporting directions including directions for at least partial preparation of the particular ingestible product to be used in a capsule form (e.g. an implementation of the receiver component s528 is configured to electronically receive the reporting directions involving engagement with the processor component s102 to direct the material processing subsystem s700 to at least partially prepare, such as through encapsulation, the particular ingestible product such as capsules, etc.). Furthermore, the receiving information capsule electrical circuitry arrangement e1149 when activated will perform the operation o1149. In an implementation, the receiving information capsule electrical circuitry arrangement e1149, when activated performs electronically receiving the reporting directions including directions for at least partial preparation of the particular ingestible product to be used in a capsule form (e.g. an implementation of the receiver component s528 is configured to electronically receive the reporting directions involving engagement with the processor component s102 to direct the material processing subsystem s700 to at least partially prepare, such as through encapsulation, the particular ingestible product such as capsules, etc.). In an implementation, the electronically receiving the reporting directions associated with at least partial preparation of the particular ingestible product to be used in a capsule form is carried out by electronically receiving the reporting directions including directions for at least partial preparation of the particular ingestible product to be used in a capsule form (e.g. an implementation of the receiver component s528 is configured to electronically receive the reporting directions involving engagement with the processor component s102 to direct the material processing subsystem s700 to at least partially prepare, such as through encapsulation, the particular ingestible product such as capsules, etc.).

In one or more implementations, operation o11 includes an operation o1150 for electronically receiving the reporting directions associated with at least partial preparation of the particular ingestible product to be used in sandwich form. An exemplary version of the non-transitory signal bearing medium n100 is depicted as bearing one or more receiving information sandwich instructions i1150 that when executed will direct performance of the operation o1150. In an implementation, the one or more receiving information sandwich instructions i1150 when executed direct electronically receiving the reporting directions including directions for at least partial preparation of the particular ingestible product to be used in sandwich form (e.g. an implementation of the receiver component s528 is configured to electronically receive the reporting directions involving engagement with the processor component s102 to direct the material processing subsystem s700 to at least partially prepare a portion of the ingestible product such as a sandwich, etc.). Furthermore, the receiving information sandwich electrical circuitry arrangement e1150 when activated will perform the operation o1150. In an implementation, the receiving information sandwich electrical circuitry arrangement e1150, when activated performs electronically receiving the reporting directions including directions for at least partial preparation of the particular ingestible product to be used in sandwich form (e.g. an implementation of the receiver component s528 is configured to electronically receive the reporting directions involving engagement with the processor component s102 to direct the material processing subsystem s700 to at least partially prepare a portion of the ingestible product such as a sandwich, etc.). In an implementation, the electronically receiving the reporting directions associated with at least partial preparation of the particular ingestible product to be used in sandwich form is carried out by electronically receiving the reporting directions including directions for at least partial preparation of the particular ingestible product to be used in sandwich form (e.g. an implementation of the receiver component s528 is configured to electronically receive the reporting directions involving engagement with the processor component s102 to direct the material processing subsystem s700 to at least partially prepare a portion of the ingestible product such as a sandwich, etc.).

Figure 39:
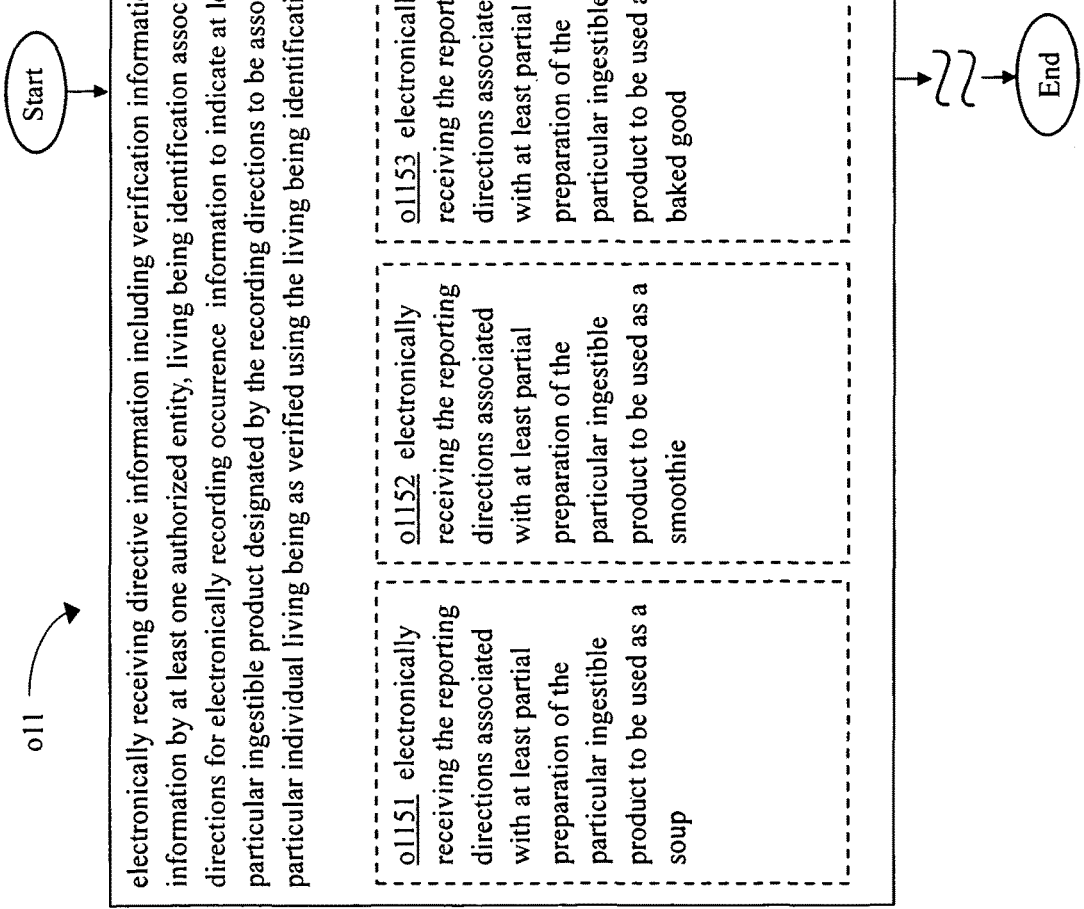
FIG. 39 is a high-level flowchart including exemplary implementations of operation O11 of FIG. 28.

In one or more implementations, as shown in FIG. 39, operation o11 includes an operation o1151 for electronically receiving the reporting directions associated with at least partial preparation of the particular ingestible product to be used as a soup. An exemplary version of the non-transitory signal bearing medium n100 is depicted as bearing one or more receiving information soup instructions i1151 that when executed will direct performance of the operation o1151. In an implementation, the one or more receiving information soup instructions i1151 when executed direct electronically receiving the reporting directions including directions for at least partial preparation of the particular ingestible product to be used as a soup (e.g. an implementation of the receiver component s528 is configured to electronically receive the reporting directions involving engagement with the processor component s102 to direct the material processing subsystem s700 to at least partially prepare a portion of the ingestible product such as a soup, etc.). Furthermore, the receiving information soup electrical circuitry arrangement e1151 when activated will perform the operation o1151. In an implementation, the receiving information soup electrical circuitry arrangement e1151, when activated performs electronically receiving the reporting directions including directions for at least partial preparation of the particular ingestible product to be used as a soup (e.g. an implementation of the receiver component s528 is configured to electronically receive the reporting directions involving engagement with the processor component s102 to direct the material processing subsystem s700 to at least partially prepare a portion of the ingestible product such as a soup, etc.). In an implementation, the electronically receiving the reporting directions associated with at least partial preparation of the particular ingestible product to be used as a soup is carried out by electronically receiving the reporting directions including directions for at least partial preparation of the particular ingestible product to be used as a soup (e.g. an implementation of the receiver component s528 is configured to electronically receive the reporting directions involving engagement with the processor component s102 to direct the material processing subsystem s700 to at least partially prepare a portion of the ingestible product such as a soup, etc.).

In one or more implementations, operation o11 includes an operation o1152 for electronically receiving the reporting directions associated with at least partial preparation of the particular ingestible product to be used as a smoothie. An exemplary version of the non-transitory signal bearing medium n100 is depicted as bearing one or more receiving information smoothie instructions i1152 that when executed will direct performance of the operation o1152. In an implementation, the one or more receiving information smoothie instructions i1152 when executed direct electronically receiving the reporting directions including directions for at least partial preparation of the particular ingestible product to be used as a smoothie (e.g. an implementation of the receiver component s528 is configured to electronically receive the reporting directions involving engagement with the processor component s102 to direct the material processing subsystem s700 to at least partially prepare a portion of the ingestible product such as a smoothie, etc.). Furthermore, the receiving information smoothie electrical circuitry arrangement e1152 when activated will perform the operation o1152. In an implementation, the receiving information smoothie electrical circuitry arrangement e1152, when activated performs electronically receiving the reporting directions including directions for at least partial preparation of the particular ingestible product to be used as a smoothie (e.g. an implementation of the receiver component s528 is configured to electronically receive the reporting directions involving engagement with the processor component s102 to direct the material processing subsystem s700 to at least partially prepare a portion of the ingestible product such as a smoothie, etc.). In an implementation, the electronically receiving the reporting directions associated with at least partial preparation of the particular ingestible product to be used as a smoothie is carried out by electronically receiving the reporting directions including directions for at least partial preparation of the particular ingestible product to be used as a smoothie (e.g. an implementation of the receiver component s528 is configured to electronically receive the reporting directions involving engagement with the processor component s102 to direct the material processing subsystem s700 to at least partially prepare a portion of the ingestible product such as a smoothie, etc.).

In one or more implementations, operation o11 includes an operation o1153 for electronically receiving the reporting directions associated with at least partial preparation of the particular ingestible product to be used as a baked good. An exemplary version of the non-transitory signal bearing medium n100 is depicted as bearing one or more receiving information baked instructions i1153 that when executed will direct performance of the operation o1153. In an implementation, the one or more receiving information baked instructions i1153 when executed direct electronically receiving the reporting directions including directions for at least partial preparation of the particular ingestible product to be used as a baked good (e.g. an implementation of the receiver component s528 is configured to electronically receive the reporting directions involving engagement with the processor component s102 to direct the material processing subsystem s700 to at least partially prepare a portion of the ingestible product such as a baked good, etc.). Furthermore, the receiving information baked electrical circuitry arrangement e1153 when activated will perform the operation o1153. In an implementation, the receiving information baked electrical circuitry arrangement e1153, when activated performs electronically receiving the reporting directions including directions for at least partial preparation of the particular ingestible product to be used as a baked good (e.g. an implementation of the receiver component s528 is configured to electronically receive the reporting directions involving engagement with the processor component s102 to direct the material processing subsystem s700 to at least partially prepare a portion of the ingestible product such as a baked good, etc.). In an implementation, the electronically receiving the reporting directions associated with at least partial preparation of the particular ingestible product to be used as a baked good is carried out by electronically receiving the reporting directions including directions for at least partial preparation of the particular ingestible product to be used as a baked good (e.g. an implementation of the receiver component s528 is configured to electronically receive the reporting directions involving engagement with the processor component s102 to direct the material processing subsystem s700 to at least partially prepare a portion of the ingestible product such as a baked good, etc.).

In one or more implementations, operation o11 includes an operation o1154 for electronically receiving the reporting directions associated with at least partial preparation of the particular ingestible product to be used as a deposited material. An exemplary version of the non-transitory signal bearing medium n100 is depicted as bearing one or more receiving information deposited instructions i1154 that when executed will direct performance of the operation o1154. In an implementation, the one or more receiving information deposited instructions i1154 when executed direct electronically receiving the reporting directions including directions for at least partial preparation of the particular ingestible product to be used as a deposited material (e.g. an implementation of the receiver component s528 is configured to electronically receive the reporting directions involving engagement with the processor component s102 to direct the material processing subsystem s700 to at least partially prepare a portion of the ingestible product as having deposited material such as a multi-layered cake, etc.). Furthermore, the receiving information deposited electrical circuitry arrangement e1154 when activated will perform the operation o1154. In an implementation, the receiving information deposited electrical circuitry arrangement e1154, when activated performs electronically receiving the reporting directions including directions for at least partial preparation of the particular ingestible product to be used as a deposited material (e.g. an implementation of the receiver component s528 is configured to electronically receive the reporting directions involving engagement with the processor component s102 to direct the material processing subsystem s700 to at least partially prepare a portion of the ingestible product as having deposited material such as a multi-layered cake, etc.). In an implementation, the electronically receiving the reporting directions associated with at least partial preparation of the particular ingestible product to be used as a deposited material is carried out by electronically receiving the reporting directions including directions for at least partial preparation of the particular ingestible product to be used as a deposited material (e.g. an implementation of the receiver component s528 is configured to electronically receive the reporting directions involving engagement with the processor component s102 to direct the material processing subsystem s700 to at least partially prepare a portion of the ingestible product as having deposited material such as a multi-layered cake, etc.).

In one or more implementations, operation o11 includes an operation o1155 for electronically receiving the reporting directions associated with at least partial preparation of the particular ingestible product to be used as an assembled concoction. An exemplary version of the non-transitory signal bearing medium n100 is depicted as bearing one or more receiving information assembled instructions i1155 that when executed will direct performance of the operation o1155. In an implementation, the one or more receiving information assembled instructions i1155 when executed direct electronically receiving the reporting directions including directions for at least partial preparation of the particular ingestible product to be used as an assembled concoction (e.g. an implementation of the receiver component s528 is configured to electronically receive the reporting directions involving engagement with the processor component s102 to direct the material processing subsystem s700 to at least partially prepare the particular ingestible product as an assembled concoction such as a decorated confection, etc.). Furthermore, the receiving information assembled electrical circuitry arrangement e1155 when activated will perform the operation o1155. In an implementation, the receiving information assembled electrical circuitry arrangement e1155, when activated performs electronically receiving the reporting directions including directions for at least partial preparation of the particular ingestible product to be used as an assembled concoction (e.g. an implementation of the receiver component s528 is configured to electronically receive the reporting directions involving engagement with the processor component s102 to direct the material processing subsystem s700 to at least partially prepare the particular ingestible product as an assembled concoction such as a decorated confection, etc.). In an implementation, the electronically receiving the reporting directions associated with at least partial preparation of the particular ingestible product to be used as an assembled concoction is carried out by electronically receiving the reporting directions including directions for at least partial preparation of the particular ingestible product to be used as an assembled concoction (e.g. an implementation of the receiver component s528 is configured to electronically receive the reporting directions involving engagement with the processor component s102 to direct the material processing subsystem s700 to at least partially prepare the particular ingestible product as an assembled concoction such as a decorated confection, etc.).

Figure 40:
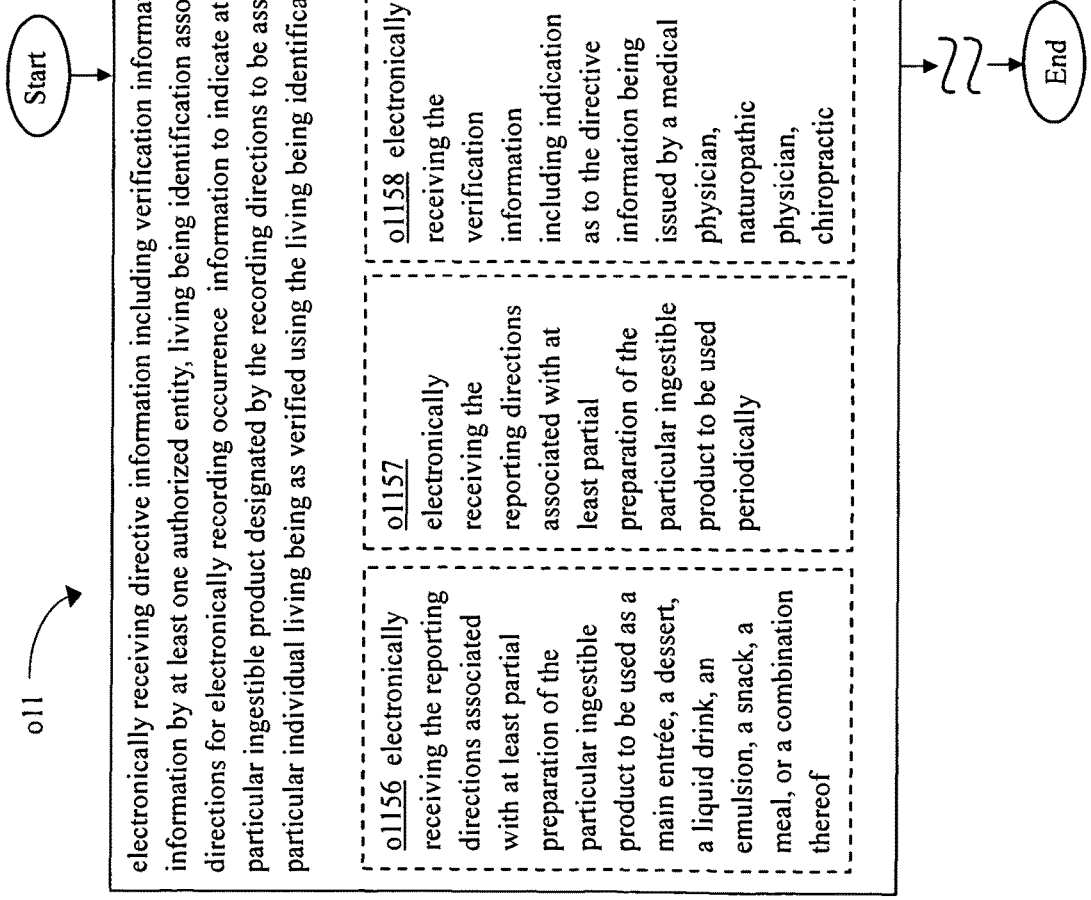
FIG. 40 is a high-level flowchart including exemplary implementations of operation O11 of FIG. 28.

In one or more implementations, as shown in FIG. 40, operation o11 includes an operation o1156 for electronically receiving the reporting directions associated with at least partial preparation of the particular ingestible product to be used as a main entrée, a dessert, a liquid drink, an emulsion, a snack, a meal, or a combination thereof. An exemplary version of the non-transitory signal bearing medium n100 is depicted as bearing one or more receiving information uses instructions i1156 that when executed will direct performance of the operation o1156. In an implementation, the one or more receiving information uses instructions i1156 when executed direct electronically receiving the reporting directions including directions for at least partial preparation of the particular ingestible product to be used as a main entrée, a dessert, a liquid drink, an emulsion, a snack, a meal, or a combination thereof (e.g. an implementation of the receiver component s528 is configured to electronically receive the reporting directions involving engagement with the processor component s102 to direct the material processing subsystem s700 to at least partially prepare the particular ingestible product such as a steak, etc.). Furthermore, the receiving information uses electrical circuitry arrangement e1156 when activated will perform the operation o1156. In an implementation, the receiving information uses electrical circuitry arrangement e1156, when activated performs electronically receiving the reporting directions including directions for at least partial preparation of the particular ingestible product to be used as a main entrée, a dessert, a liquid drink, an emulsion, a snack, a meal, or a combination thereof (e.g. an implementation of the receiver component s528 is configured to electronically receive the reporting directions involving engagement with the processor component s102 to direct the material processing subsystem s700 to at least partially prepare the particular ingestible product such as a steak, etc.). In an implementation, the electronically receiving the reporting directions associated with at least partial preparation of the particular ingestible product to be used as a main entrée, a dessert, a liquid drink, an emulsion, a snack, a meal, or a combination thereof is carried out by electronically receiving the reporting directions including directions for at least partial preparation of the particular ingestible product to be used as a main entrée, a dessert, a liquid drink, an emulsion, a snack, a meal, or a combination thereof (e.g. an implementation of the receiver component s528 is configured to electronically receive the reporting directions involving engagement with the processor component s102 to direct the material processing subsystem s700 to at least partially prepare the particular ingestible product such as a steak, etc.).

In one or more implementations, operation o11 includes an operation o1157 for electronically receiving the reporting directions associated with at least partial preparation of the particular ingestible product to be used periodically. An exemplary version of the non-transitory signal bearing medium n100 is depicted as bearing one or more receiving information periods instructions i1157 that when executed will direct performance of the operation o1157. In an implementation, the one or more receiving information periods instructions i1157 when executed direct electronically receiving the reporting directions including directions for at least partial preparation of the particular ingestible product to be used periodically (e.g. an implementation of the receiver component s528 is configured to electronically receive the reporting directions involving engagement with the processor component s102 to direct the material processing subsystem s700 to at least partially prepare the particular ingestible product such as once a week, etc.). Furthermore, the receiving information periods electrical circuitry arrangement e1157 when activated will perform the operation o1157. In an implementation, the receiving information periods electrical circuitry arrangement e1157, when activated performs electronically receiving the reporting directions including directions for at least partial preparation of the particular ingestible product to be used periodically (e.g. an implementation of the receiver component s528 is configured to electronically receive the reporting directions involving engagement with the processor component s102 to direct the material processing subsystem s700 to at least partially prepare the particular ingestible product such as once a week, etc.). In an implementation, the electronically receiving the reporting directions associated with at least partial preparation of the particular ingestible product to be used periodically is carried out by electronically receiving the reporting directions including directions for at least partial preparation of the particular ingestible product to be used periodically (e.g. an implementation of the receiver component s528 is configured to electronically receive the reporting directions involving engagement with the processor component s102 to direct the material processing subsystem s700 to at least partially prepare the particular ingestible product such as once a week, etc.).

In one or more implementations, operation o11 includes an operation o1158 for electronically receiving the verification information including indication as to the directive information being issued by a medical physician, naturopathic physician, chiropractic physician, physician, nurse practitioner, nurse, dentist, or a combination thereof. An exemplary version of the non-transitory signal bearing medium n100 is depicted as bearing one or more receiving information care giver instructions i1158 that when executed will direct performance of the operation o1158. In an implementation, the one or more receiving information care giver instructions i1158 when executed direct electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.). Furthermore, the receiving information care giver electrical circuitry arrangement e1158 when activated will perform the operation o1158. In an implementation, the receiving information care giver electrical circuitry arrangement e1158, when activated performs electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.). In an implementation, the electronically receiving the verification information including indication as to the directive information being issued by a medical physician, naturopathic physician, chiropractic physician, physician, nurse practitioner, nurse, dentist, or a combination thereof is carried out by electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.).

In one or more implementations, operation o11 includes an operation o1159 for electronically receiving the verification information including indication as to the directive information being issued by a hospital, medical clinic, a research institution, a pharmacy, a pharmaceutical company, a computer software company, or a combination thereof. An exemplary version of the non-transitory signal bearing medium n100 is depicted as bearing one or more receiving information organization instructions i1159 that when executed will direct performance of the operation o1159. In an implementation, the one or more receiving information organization instructions i1159 when executed direct electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.). Furthermore, the receiving information organization electrical circuitry arrangement e1159 when activated will perform the operation o1159. In an implementation, the receiving information organization electrical circuitry arrangement e1159, when activated performs electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.). In an implementation, the electronically receiving the verification information including indication as to the directive information being issued by a hospital, medical clinic, a research institution, a pharmacy, a pharmaceutical company, a computer software company, or a combination thereof is carried out by electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.).

In one or more implementations, operation o11 includes an operation o1160 for electronically receiving the verification information including indication as to the directive information being issued by a provider of preventive medicine, a provider of therapeutic medicine, a provider of maintenance care, a provider of palliative care, a provider of folk medicine, or a combination thereof. An exemplary version of the non-transitory signal bearing medium n100 is depicted as bearing one or more receiving information preventive instructions i1160 that when executed will direct performance of the operation o1160. In an implementation, the one or more receiving information preventive instructions i1160 when executed direct electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.). Furthermore, the receiving information preventive electrical circuitry arrangement e1160 when activated will perform the operation o1160. In an implementation, the receiving information preventive electrical circuitry arrangement e1160, when activated performs electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.). In an implementation, the electronically receiving the verification information including indication as to the directive information being issued by a provider of preventive medicine, a provider of therapeutic medicine, a provider of maintenance care, a provider of palliative care, a provider of folk medicine, or a combination thereof is carried out by electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.).

Figure 41:
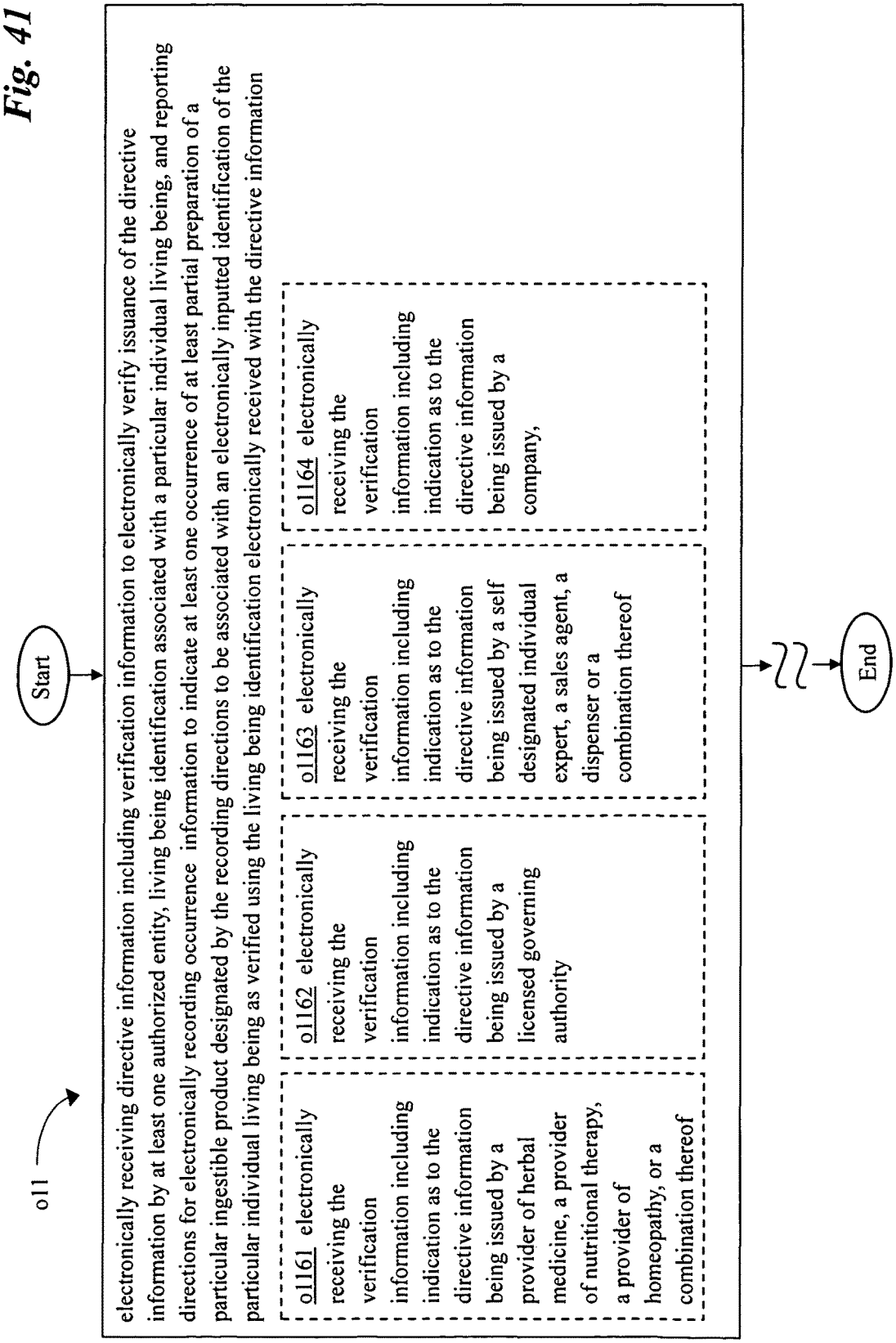
FIG. 41 is a high-level flowchart including exemplary implementations of operation O11 of FIG. 28.

In one or more implementations, as shown in FIG. 41, operation o11 includes an operation o1161 for electronically receiving the verification information including indication as to the directive information being issued by a provider of herbal medicine, a provider of nutritional therapy, a provider of homeopathy, or a combination thereof. An exemplary version of the non-transitory signal bearing medium n100 is depicted as bearing one or more receiving information alternative instructions i1161 that when executed will direct performance of the operation o1161. In an implementation, the one or more receiving information alternative instructions i1161 when executed direct electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.). Furthermore, the receiving information alternative electrical circuitry arrangement e1161 when activated will perform the operation o1161. In an implementation, the receiving information alternative electrical circuitry arrangement e1161, when activated performs electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.). In an implementation, the electronically receiving the verification information including indication as to the directive information being issued by a provider of herbal medicine, a provider of nutritional therapy, a provider of homeopathy, or a combination thereof is carried out by electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.).

In one or more implementations, operation o11 includes an operation o1162 for electronically receiving the verification information including indication as to the directive information being issued by a licensed governing authority. An exemplary version of the non-transitory signal bearing medium n100 is depicted as bearing one or more receiving information authority instructions i1162 that when executed will direct performance of the operation o1162. In an implementation, the one or more receiving information authority instructions i1162 when executed direct electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.). Furthermore, the receiving information authority electrical circuitry arrangement e1162 when activated will perform the operation o1162. In an implementation, the receiving information authority electrical circuitry arrangement e1162, when activated performs electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.). In an implementation, the electronically receiving the verification information including indication as to the directive information being issued by a licensed governing authority is carried out by electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.).

In one or more implementations, operation o11 includes an operation o1163 for electronically receiving the verification information including indication as to the directive information being issued by a self designated individual expert, a sales agent, a dispenser or a combination thereof. An exemplary version of the non-transitory signal bearing medium n100 is depicted as bearing one or more receiving information individual instructions i1163 that when executed will direct performance of the operation o1163. In an implementation, the one or more receiving information individual instructions i1163 when executed direct electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.). Furthermore, the receiving information individual electrical circuitry arrangement e1163 when activated will perform the operation o1163. In an implementation, the receiving information individual electrical circuitry arrangement e1163, when activated performs electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.). In an implementation, the electronically receiving the verification information including indication as to the directive information being issued by a self designated individual expert, a sales agent, a dispenser or a combination thereof is carried out by electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.).

In one or more implementations, operation o11 includes an operation o1164 for electronically receiving the verification information including indication as to the directive information being issued by a company. An exemplary version of the non-transitory signal bearing medium n100 is depicted as bearing one or more receiving information company instructions i1164 that when executed will direct performance of the operation o1164. In an implementation, the one or more receiving information company instructions i1164 when executed direct electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.). Furthermore, the receiving information company electrical circuitry arrangement e1164 when activated will perform the operation o1164. In an implementation, the receiving information company electrical circuitry arrangement e1164, when activated performs electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.). In an implementation, the electronically receiving the verification information including indication as to the directive information being issued by a company, is carried out by electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.).

As shown in FIG. 28, the operational flow o10 proceeds to operation o12 for electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being. An exemplary version of the non-transitory signal bearing medium n100 is depicted as bearing one or more transmitting occurrence info instructions i12 that when executed will direct performance of the operation o12. In an implementation, the one or more transmitting occurrence info instructions i12 when executed direct electronically transmitting the occurrence information to an electronic receiving device (e.g. the wireless network component s512 transmits the occurrence information to a wireless receiving device, etc.) to be accessed by at least one recipient identified by the reporting directions as authorized to access the occurrence information (e.g. a particular physician is identified by the reporting directions as authorized to access the occurrence information as a recipient, etc.) subsequent to verification that the electronically received directive information was issued by the at least one authorized entity (e.g. the microprocessor s102 determines that the received directive information was issued by an authorized entity such as a physician a particular hospital) and subsequent to the electronic inputting of the identification of the particular individual living being (e.g. the scanner component s338 is used to scan the iris of a human adult as the particular individual living being to identify the human adult, etc.) the occurrence information indicating the at least one occurrence of at least partial preparation of the particular ingestible product being associated with the particular individual living being (e.g. the central processing unit s104 directs the material processing subsystem s700 to at least partially prepare a multi-layered dessert, etc.). Furthermore, the transmitting occurrence info electrical circuitry arrangement e12 when activated will perform the operation o12. In an implementation, the transmitting occurrence info electrical circuitry arrangement e12, when activated performs electronically transmitting the occurrence information to an electronic receiving device (e.g. the wireless network component s512 transmits the occurrence information to a wireless receiving device, etc.) to be accessed by at least one recipient identified by the reporting directions as authorized to access the occurrence information (e.g. a particular physician is identified by the reporting directions as authorized to access the occurrence information as a recipient, etc.) subsequent to verification that the electronically received directive information was issued by the at least one authorized entity (e.g. the microprocessor s102 determines that the received directive information was issued by an authorized entity such as a physician a particular hospital) and subsequent to the electronic inputting of the identification of the particular individual living being (e.g. the scanner component s338 is used to scan the iris of a human adult as the particular individual living being to identify the human adult, etc.) the occurrence information indicating the at least one occurrence of at least partial preparation of the particular ingestible product being associated with the particular individual living being (e.g. the central processing unit s104 directs the material processing subsystem s700 to at least partially prepare a multi-layered dessert, etc.). In an implementation, the electronically transmitting the occurrence information to an electronic receiving device to be accessed by at least one recipient identified by the reporting directions as authorized to access the occurrence information subsequent to verification that the electronically received directive information was issued by the at least one authorized entity and subsequent to the electronic inputting of the identification of the particular individual living being, the occurrence information indicating the at least one occurrence of at least partial preparation of the particular ingestible product being associated with the particular individual living being is carried out by electronically transmitting the occurrence information to an electronic receiving device (e.g. the wireless network component s512 transmits the occurrence information to a wireless receiving device, etc.) to be accessed by at least one recipient identified by the reporting directions as authorized to access the occurrence information (e.g. a particular physician is identified by the reporting directions as authorized to access the occurrence information as a recipient, etc.) subsequent to verification that the electronically received directive information was issued by the at least one authorized entity (e.g. the microprocessor s102 determines that the received directive information was issued by an authorized entity such as a physician a particular hospital) and subsequent to the electronic inputting of the identification of the particular individual living being (e.g. the scanner component s338 is used to scan the iris of a human adult as the particular individual living being to identify the human adult, etc.) the occurrence information indicating the at least one occurrence of at least partial preparation of the particular ingestible product being associated with the particular individual living being (e.g. the central processing unit s104 directs the material processing subsystem s700 to at least partially prepare a multi-layered dessert, etc.).

Figure 42:
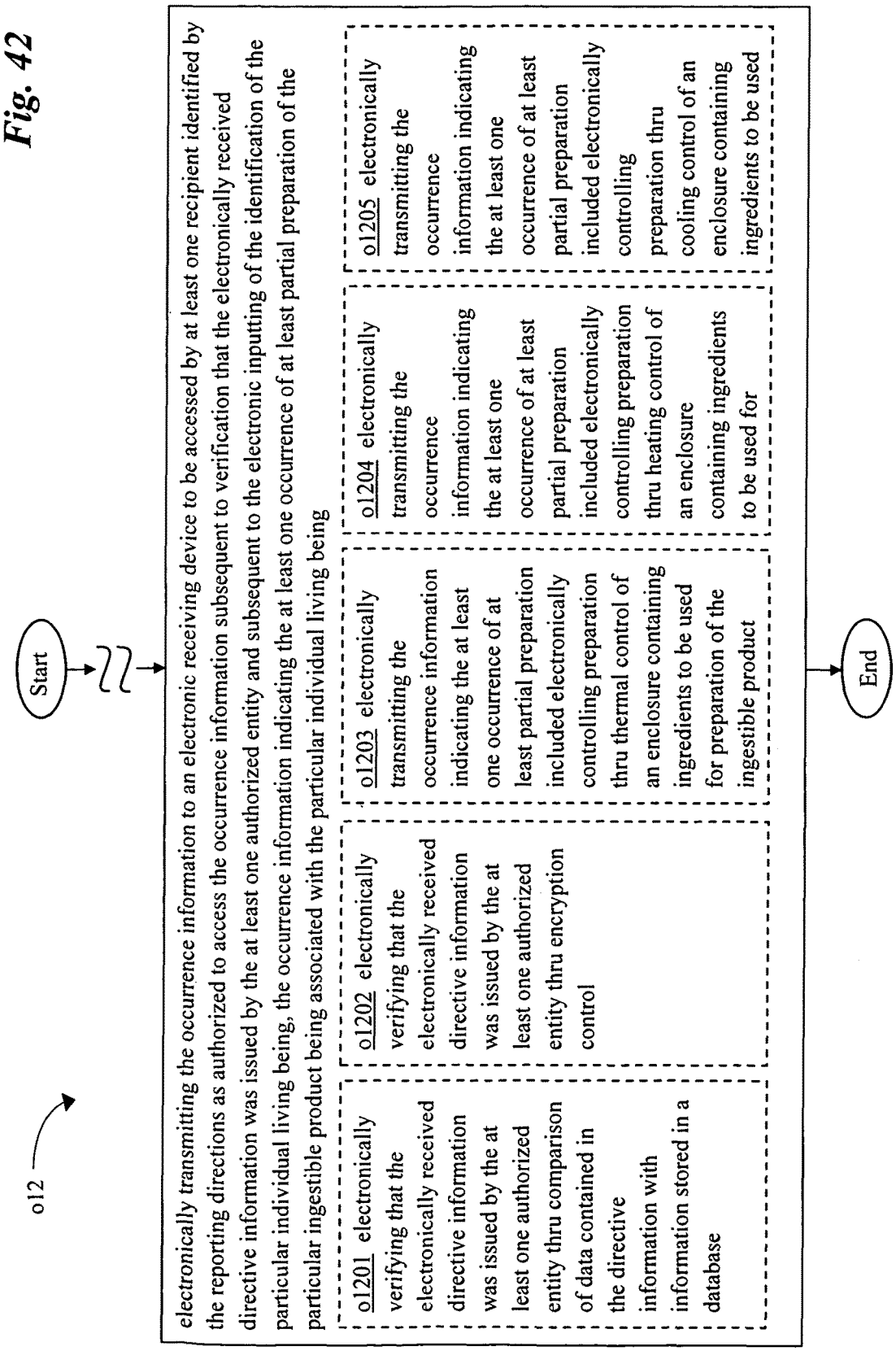
FIG. 42 is a high-level flowchart including exemplary implementations of operation O12 of FIG. 28.

In one or more implementations, as shown in FIG. 42, operation o12 includes an operation o1201 for electronically verifying that the electronically received directive information was issued by the at least one authorized entity thru comparison of data contained in the directive information with information stored in a database. An exemplary version of the non-transitory signal bearing medium n100 is depicted as bearing one or more verifying thru comparison instructions i1201 that when executed will direct performance of the operation o1201. In an implementation, the one or more verifying thru comparison instructions i1201 when executed direct electronically verifying that the electronically received directive information was issued by the at least one authorized entity thru comparison of data contained in the directive information with information stored in a database (e.g. an implementation of the processor component s102 is configured to electronically compare data contained in the directive information and received by the receiver component s528 with information stored in the hard drive component s222, etc.). Furthermore, the verifying thru comparison electrical circuitry arrangement e1201 when activated will perform the operation o1201. In an implementation, the verifying thru comparison electrical circuitry arrangement e1201, when activated performs electronically verifying that the electronically received directive information was issued by the at least one authorized entity thru comparison of data contained in the directive information with information stored in a database (e.g. an implementation of the processor component s102 is configured to electronically compare data contained in the directive information and received by the receiver component s528 with information stored in the hard drive component s222, etc.). In an implementation, the electronically verifying that the electronically received directive information was issued by the at least one authorized entity thru comparison of data contained in the directive information with information stored in a database is carried out by electronically verifying that the electronically received directive information was issued by the at least one authorized entity thru comparison of data contained in the directive information with information stored in a database (e.g. an implementation of the processor component s102 is configured to electronically compare data contained in the directive information and received by the receiver component s528 with information stored in the hard drive component s222, etc.).

In one or more implementations, operation o12 includes an operation o1202 for electronically verifying that the electronically received directive information was issued by the at least one authorized entity thru encryption control. An exemplary version of the non-transitory signal bearing medium n100 is depicted as bearing one or more verifying thru encryption instructions i1202 that when executed will direct performance of the operation o1202. In an implementation, the one or more verifying thru encryption instructions i1202 when executed direct electronically verifying that the electronically received directive information was issued by the at least one authorized entity thru encryption control (e.g. an implementation of the processor component s102 is configured to electronically implement an encryption key control that a physician was authorized to issue the controlled substance information pertaining to a pharmaceutical medication, etc.). Furthermore, the verifying thru encryption electrical circuitry arrangement e1202 when activated will perform the operation o1202. In an implementation, the verifying thru encryption electrical circuitry arrangement e1202, when activated performs electronically verifying that the electronically received directive information was issued by the at least one authorized entity thru encryption control (e.g. an implementation of the processor component s102 is configured to electronically implement an encryption key control that a physician was authorized to issue the controlled substance information pertaining to a pharmaceutical medication, etc.). In an implementation, the electronically verifying that the electronically received directive information was issued by the at least one authorized entity thru encryption control is carried out by electronically verifying that the electronically received directive information was issued by the at least one authorized entity thru encryption control (e.g. an implementation of the processor component s102 is configured to electronically implement an encryption key control that a physician was authorized to issue the controlled substance information pertaining to a pharmaceutical medication, etc.).

In one or more implementations, operation o12 includes an operation o1203 for electronically transmitting the occurrence information indicating the at least one occurrence of at least partial preparation included electronically controlling preparation thru thermal control of an enclosure containing ingredients to be used for preparation of the ingestible product. An exemplary version of the non-transitory signal bearing medium n100 is depicted as bearing one or more transmit control prep thermal instructions i1203 that when executed will direct performance of the operation o1203. In an implementation, the one or more transmit control prep thermal instructions i1203 when executed direct electronically transmitting the occurrence information indicating the at least one occurrence of at least partial preparation included electronically controlling preparation thru thermal control of an enclosure containing ingredients to be used for preparation of the ingestible product (e.g. the internet network component s508 is configured to transmit the occurrence information indicating the at least one occurrence of at least partial preparation including an implementation of the processor component s102 is configured to electronically control the laser component s708 according to a temperature profile included in the directive information, etc.). Furthermore, the transmit control prep thermal electrical circuitry arrangement e1203 when activated will perform the operation o1203. In an implementation, the transmit control prep thermal electrical circuitry arrangement e1203, when activated performs electronically transmitting the occurrence information indicating the at least one occurrence of at least partial preparation included electronically controlling preparation thru thermal control of an enclosure containing ingredients to be used for preparation of the ingestible product (e.g. the internet network component s508 is configured to transmit the occurrence information indicating the at least one occurrence of at least partial preparation including an implementation of the processor component s102 is configured to electronically control the laser component s708 according to a temperature profile included in the directive information, etc.). In an implementation, the electronically transmitting the occurrence information indicating the at least one occurrence of at least partial preparation included electronically controlling preparation thru thermal control of an enclosure containing ingredients to be used for preparation of the ingestible product is carried out by electronically transmitting the occurrence information indicating the at least one occurrence of at least partial preparation included electronically controlling preparation thru thermal control of an enclosure containing ingredients to be used for preparation of the ingestible product (e.g. the internet network component s508 is configured to transmit the occurrence information indicating the at least one occurrence of at least partial preparation including an implementation of the processor component s102 is configured to electronically control the laser component s708 according to a temperature profile included in the directive information, etc.).

In one or more implementations, operation o12 includes an operation o1204 for electronically transmitting the occurrence information indicating the at least one occurrence of at least partial preparation included electronically controlling preparation thru heating control of an enclosure containing ingredients to be used for preparation of the ingestible product. An exemplary version of the non-transitory signal bearing medium n100 is depicted as bearing one or more transmit control prep heating instructions i1204 that when executed will direct performance of the operation o1204. In an implementation, the one or more transmit control prep heating instructions i1204 when executed direct electronically transmitting the occurrence information indicating the at least one occurrence of at least partial preparation included electronically controlling preparation thru heating control of an enclosure containing ingredients to be used for preparation of the ingestible product (e.g. the optical network component s504 is configured to transmit the occurrence information indicating the at least one occurrence of at least partial preparation including an implementation of the processor component s102 is configured to electronically control the heating component s702 according to a temperature profile included in the directive information, etc.). Furthermore, the verifying thru comparison electrical circuitry arrangement e1204 when activated will perform the operation o1204. In an implementation, the transmit control prep heating electrical circuitry arrangement e1204, when activated performs electronically transmitting the occurrence information indicating the at least one occurrence of at least partial preparation included electronically controlling preparation thru heating control of an enclosure containing ingredients to be used for preparation of the ingestible product (e.g. the optical network component s504 is configured to transmit the occurrence information indicating the at least one occurrence of at least partial preparation including an implementation of the processor component s102 is configured to electronically control the heating component s702 according to a temperature profile included in the directive information, etc.). In an implementation, the electronically transmitting the occurrence information indicating the at least one occurrence of at least partial preparation included electronically controlling preparation thru heating control of an enclosure containing ingredients to be used for preparation of the ingestible product is carried out by electronically transmitting the occurrence information indicating the at least one occurrence of at least partial preparation included electronically controlling preparation thru heating control of an enclosure containing ingredients to be used for preparation of the ingestible product (e.g. the optical network component s504 is configured to transmit the occurrence information indicating the at least one occurrence of at least partial preparation including an implementation of the processor component s102 is configured to electronically control the heating component s702 according to a temperature profile included in the directive information, etc.).

In one or more implementations, operation o12 includes an operation o1205 for electronically transmitting the occurrence information indicating the at least one occurrence of at least partial preparation included electronically controlling preparation thru cooling control of an enclosure containing ingredients to be used for preparation of the ingestible product. An exemplary version of the non-transitory signal bearing medium n100 is depicted as bearing one or more transmit control prep cooling instructions i1205 that when executed will direct performance of the operation o1205. In an implementation, the one or more transmit control prep cooling instructions i1205 when executed direct electronically transmitting the occurrence information indicating the at least one occurrence of at least partial preparation included electronically controlling preparation thru cooling control of an enclosure containing ingredients to be used for preparation of the ingestible product (e.g. the wireless network component s510 is configured to transmit the occurrence information indicating the at least one occurrence of at least partial preparation including an implementation of the processor component s102 is configured to electronically control the cooling component s704 according to a temperature profile included in the directive information, etc.). Furthermore, the transmit control prep cooling electrical circuitry arrangement e1205 when activated will perform the operation o1205. In an implementation, the transmit control prep cooling electrical circuitry arrangement e1205, when activated performs electronically transmitting the occurrence information indicating the at least one occurrence of at least partial preparation included electronically controlling preparation thru cooling control of an enclosure containing ingredients to be used for preparation of the ingestible product (e.g. the wireless network component s510 is configured to transmit the occurrence information indicating the at least one occurrence of at least partial preparation including an implementation of the processor component s102 is configured to electronically control the cooling component s704 according to a temperature profile included in the directive information, etc.). In an implementation, the electronically transmitting the occurrence information indicating the at least one occurrence of at least partial preparation included electronically controlling preparation thru cooling control of an enclosure containing ingredients to be used for preparation of the ingestible product is carried out by electronically transmitting the occurrence information indicating the at least one occurrence of at least partial preparation included electronically controlling preparation thru cooling control of an enclosure containing ingredients to be used for preparation of the ingestible product (e.g. the wireless network component s510 is configured to transmit the occurrence information indicating the at least one occurrence of at least partial preparation including an implementation of the processor component s102 is configured to electronically control the cooling component s704 according to a temperature profile included in the directive information, etc.).

Figure 43:
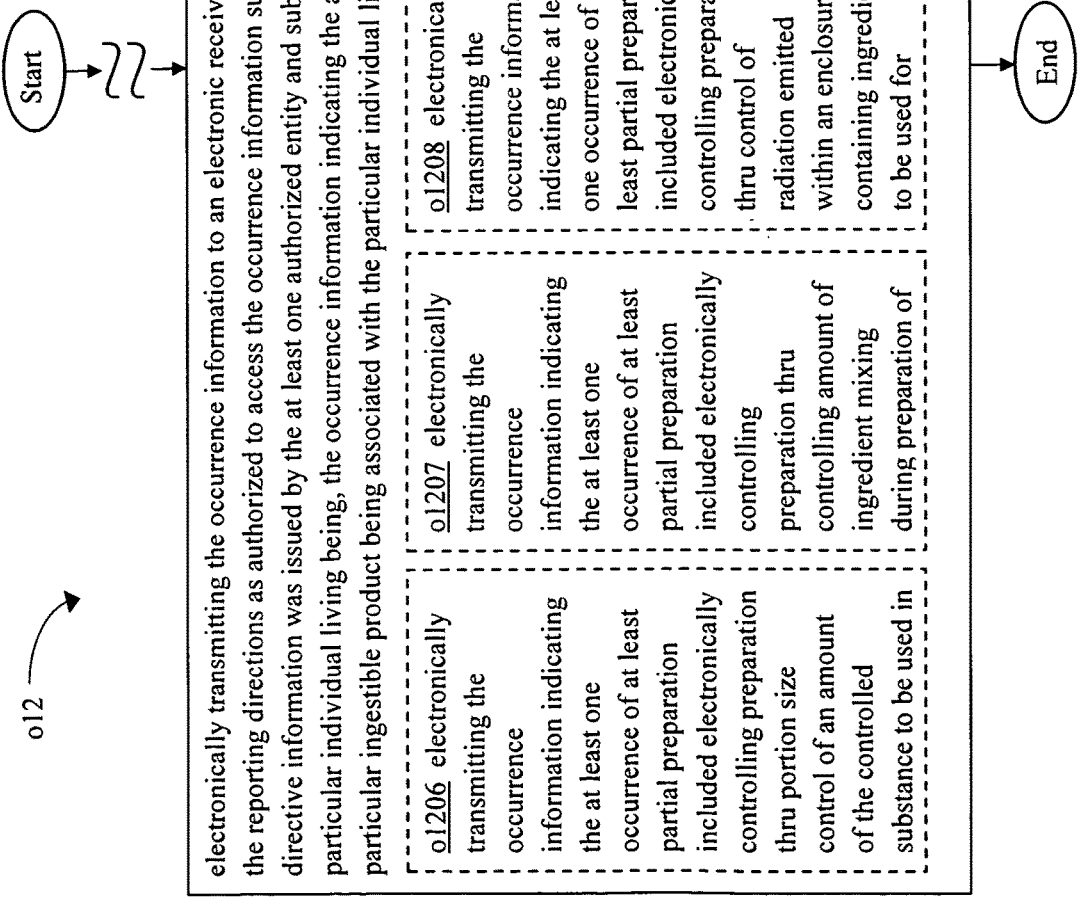
FIG. 43 is a high-level flowchart including exemplary implementations of operation O12 of FIG. 28.

In one or more implementations, as shown in FIG. 43, operation o12 includes an operation o1206 for electronically transmitting the occurrence information indicating the at least one occurrence of at least partial preparation included electronically controlling preparation thru portion size control of an amount of the controlled substance to be used in preparation of the ingestible product. An exemplary version of the non-transitory signal bearing medium n100 is depicted as bearing one or more transmit control prep portion size instructions i1206 that when executed will direct performance of the operation o1206. In an implementation, the one or more transmit control prep portion size instructions i1206 when executed direct electronically transmitting the occurrence information indicating the at least one occurrence of at least partial preparation included electronically controlling preparation thru portion size control of an amount of the controlled substance to be used in preparation of the ingestible product (e.g. the wired network component s512 is configured to transmit the occurrence information indicating the at least one occurrence of at least partial preparation including an implementation of the processor component s102 is configured to electronically control the sorting component s728 according to a ingredient size distribution profile included in the directive information, etc.). Furthermore, the transmit control prep portion size electrical circuitry arrangement e1206 when activated will perform the operation o1205. In an implementation, the transmit control prep portion size electrical circuitry arrangement e1206, when activated performs electronically transmitting the occurrence information indicating the at least one occurrence of at least partial preparation included electronically controlling preparation thru portion size control of an amount of the controlled substance to be used in preparation of the ingestible product (e.g. the wired network component s512 is configured to transmit the occurrence information indicating the at least one occurrence of at least partial preparation including an implementation of the processor component s102 is configured to electronically control the sorting component s728 according to a ingredient size distribution profile included in the directive information, etc.). In an implementation, the electronically transmitting the occurrence information indicating the at least one occurrence of at least partial preparation included electronically controlling preparation thru portion size control of an amount of the controlled substance to be used in preparation of the ingestible product is carried out by electronically transmitting the occurrence information indicating the at least one occurrence of at least partial preparation included electronically controlling preparation thru portion size control of an amount of the controlled substance to be used in preparation of the ingestible product (e.g. the wired network component s512 is configured to transmit the occurrence information indicating the at least one occurrence of at least partial preparation including an implementation of the processor component s102 is configured to electronically control the sorting component s728 according to a ingredient size distribution profile included in the directive information, etc.).

In one or more implementations, operation o12 includes an operation o1207 for electronically transmitting the occurrence information indicating the at least one occurrence of at least partial preparation included electronically controlling preparation thru controlling amount of ingredient mixing during preparation of the ingestible product. An exemplary version of the non-transitory signal bearing medium n100 is depicted as bearing one or more transmit control prep mixing instructions i1207 that when executed will direct performance of the operation o1207. In an implementation, the one or more transmit control prep mixing instructions i1207 when executed direct electronically transmitting the occurrence information indicating the at least one occurrence of at least partial preparation included electronically controlling preparation thru controlling amount of ingredient mixing during preparation of the ingestible product (e.g. the cellular network component s514 is configured to transmit the occurrence information indicating the at least one occurrence of at least partial preparation including an implementation of the processor component s102 is configured to electronically control the mixer component s716 according to a mixing profile included in the directive information, etc.). Furthermore, the transmit control prep mixing electrical circuitry arrangement e1207 when activated will perform the operation o1207. In an implementation, the transmit control prep mixing electrical circuitry arrangement e1207, when activated performs electronically transmitting the occurrence information indicating the at least one occurrence of at least partial preparation included electronically controlling preparation thru controlling amount of ingredient mixing during preparation of the ingestible product (e.g. the cellular network component s514 is configured to transmit the occurrence information indicating the at least one occurrence of at least partial preparation including an implementation of the processor component s102 is configured to electronically control the mixer component s716 according to a mixing profile included in the directive information, etc.). In an implementation, the electronically transmitting the occurrence information indicating the at least one occurrence of at least partial preparation included electronically controlling preparation thru controlling amount of ingredient mixing during preparation of the ingestible product is carried out by electronically transmitting the occurrence information indicating the at least one occurrence of at least partial preparation included electronically controlling preparation thru controlling amount of ingredient mixing during preparation of the ingestible product (e.g. the cellular network component s514 is configured to transmit the occurrence information indicating the at least one occurrence of at least partial preparation including an implementation of the processor component s102 is configured to electronically control the mixer component s716 according to a mixing profile included in the directive information, etc.).

In one or more implementations, operation o12 includes an operation o1208 for electronically transmitting the occurrence information indicating the at least one occurrence of at least partial preparation included electronically controlling preparation thru control of radiation emitted within an enclosure containing ingredients to be used for preparation of the ingestible product. An exemplary version of the non-transitory signal bearing medium n100 is depicted as bearing one or more transmit control prep radiation instructions i1208 that when executed will direct performance of the operation o1208. In an implementation, the one or more transmit control prep radiation instructions i1208 when executed direct electronically transmitting the occurrence information indicating the at least one occurrence of at least partial preparation included electronically controlling preparation thru control of radiation emitted within an enclosure containing ingredients to be used for preparation of the ingestible product (e.g. the wide area network component s516 is configured to transmit the occurrence information indicating the at least one occurrence of at least partial preparation including an implementation of the processor component s102 is configured to electronically control the energy emitting component s724 configured to emit radiation according to a radiation profile included in the directive information, etc.). Furthermore, the transmit control prep radiation electrical circuitry arrangement e1208 when activated will perform the operation o1208. In an implementation, the transmit control prep radiation electrical circuitry arrangement e1208, when activated performs electronically transmitting the occurrence information indicating the at least one occurrence of at least partial preparation included electronically controlling preparation thru control of radiation emitted within an enclosure containing ingredients to be used for preparation of the ingestible product (e.g. the wide area network component s516 is configured to transmit the occurrence information indicating the at least one occurrence of at least partial preparation including an implementation of the processor component s102 is configured to electronically control the energy emitting component s724 configured to emit radiation according to a radiation profile included in the directive information, etc.). In an implementation, the electronically transmitting the occurrence information indicating the at least one occurrence of at least partial preparation included electronically controlling preparation thru control of radiation emitted within an enclosure containing ingredients to be used for preparation of the ingestible product is carried out by electronically transmitting the occurrence information indicating the at least one occurrence of at least partial preparation included electronically controlling preparation thru control of radiation emitted within an enclosure containing ingredients to be used for preparation of the ingestible product (e.g. the wide area network component s516 is configured to transmit the occurrence information indicating the at least one occurrence of at least partial preparation including an implementation of the processor component s102 is configured to electronically control the energy emitting component s724 configured to emit radiation according to a radiation profile included in the directive information, etc.).

In one or more implementations, operation o12 includes an operation o1209 for electronically transmitting the occurrence information indicating the at least one occurrence of at least partial preparation included electronically controlling preparation thru control of sound emitted within an enclosure containing ingredients to be used for preparation of the ingestible product. An exemplary version of the non-transitory signal bearing medium n100 is depicted as bearing one or more transmit control prep sound instructions i1209 that when executed will direct performance of the operation o1209. In an implementation, the one or more transmit control prep sound instructions i1209 when executed direct electronically transmitting the occurrence information indicating the at least one occurrence of at least partial preparation included electronically controlling preparation thru control of sound emitted within an enclosure containing ingredients to be used for preparation of the ingestible product (e.g. the local area network component s518 is configured to transmit the occurrence information indicating the at least one occurrence of at least partial preparation including an implementation of the processor component s102 is configured to electronically control the acoustic energy component s718 according to an acoustic energy profile included in the directive information, etc.). Furthermore, the transmit control prep sound electrical circuitry arrangement e1209 when activated will perform the operation o1209. In an implementation, the transmit control prep sound electrical circuitry arrangement e1209, when activated performs electronically transmitting the occurrence information indicating the at least one occurrence of at least partial preparation included electronically controlling preparation thru control of sound emitted within an enclosure containing ingredients to be used for preparation of the ingestible product (e.g. the local area network component s518 is configured to transmit the occurrence information indicating the at least one occurrence of at least partial preparation including an implementation of the processor component s102 is configured to electronically control the acoustic energy component s718 according to an acoustic energy profile included in the directive information, etc.). In an implementation, the electronically transmitting the occurrence information indicating the at least one occurrence of at least partial preparation included electronically controlling preparation thru control of sound emitted within an enclosure containing ingredients to be used for preparation of the ingestible product is carried out by electronically transmitting the occurrence information indicating the at least one occurrence of at least partial preparation included electronically controlling preparation thru control of sound emitted within an enclosure containing ingredients to be used for preparation of the ingestible product (e.g. the local area network component s518 is configured to transmit the occurrence information indicating the at least one occurrence of at least partial preparation including an implementation of the processor component s102 is configured to electronically control the acoustic energy component s718 according to an acoustic energy profile included in the directive information, etc.).

In one or more implementations, operation o12 includes an operation o1210 for electronically transmitting the occurrence information indicating the at least one occurrence of at least partial preparation included electronically controlling preparation thru control of infrared radiation emitted within an enclosure containing ingredients to be used for preparation of the ingestible product. An exemplary version of the non-transitory signal bearing medium n100 is depicted as bearing one or more transmit control prep infrared instructions i1210 that when executed will direct performance of the operation o1210. In an implementation, the one or more transmit control prep infrared instructions i1210 when executed direct electronically transmitting the occurrence information indicating the at least one occurrence of at least partial preparation included electronically controlling preparation thru control of infrared radiation emitted within an enclosure containing ingredients to be used for preparation of the ingestible product (e.g. the encrypted communication component s520 is configured to transmit the occurrence information indicating the at least one occurrence of at least partial preparation including an implementation of the processor component s102 is configured to electronically control the infrared component s730 according to a temperature profile included in the directive information, etc.). Furthermore, the transmit control prep infrared electrical circuitry arrangement e1210 when activated will perform the operation o1210. In an implementation, the transmit control prep infrared electrical circuitry arrangement e1210, when activated performs electronically transmitting the occurrence information indicating the at least one occurrence of at least partial preparation included electronically controlling preparation thru control of infrared radiation emitted within an enclosure containing ingredients to be used for preparation of the ingestible product (e.g. the encrypted communication component s520 is configured to transmit the occurrence information indicating the at least one occurrence of at least partial preparation including an implementation of the processor component s102 is configured to electronically control the infrared component s730 according to a temperature profile included in the directive information, etc.). In an implementation, the electronically transmitting the occurrence information indicating the at least one occurrence of at least partial preparation included electronically controlling preparation thru control of infrared radiation emitted within an enclosure containing ingredients to be used for preparation of the ingestible product is carried out by electronically transmitting the occurrence information indicating the at least one occurrence of at least partial preparation included electronically controlling preparation thru control of infrared radiation emitted within an enclosure containing ingredients to be used for preparation of the ingestible product (e.g. the encrypted communication component s520 is configured to transmit the occurrence information indicating the at least one occurrence of at least partial preparation including an implementation of the processor component s102 is configured to electronically control the infrared component s730 according to a temperature profile included in the directive information, etc.).

Figure 44:
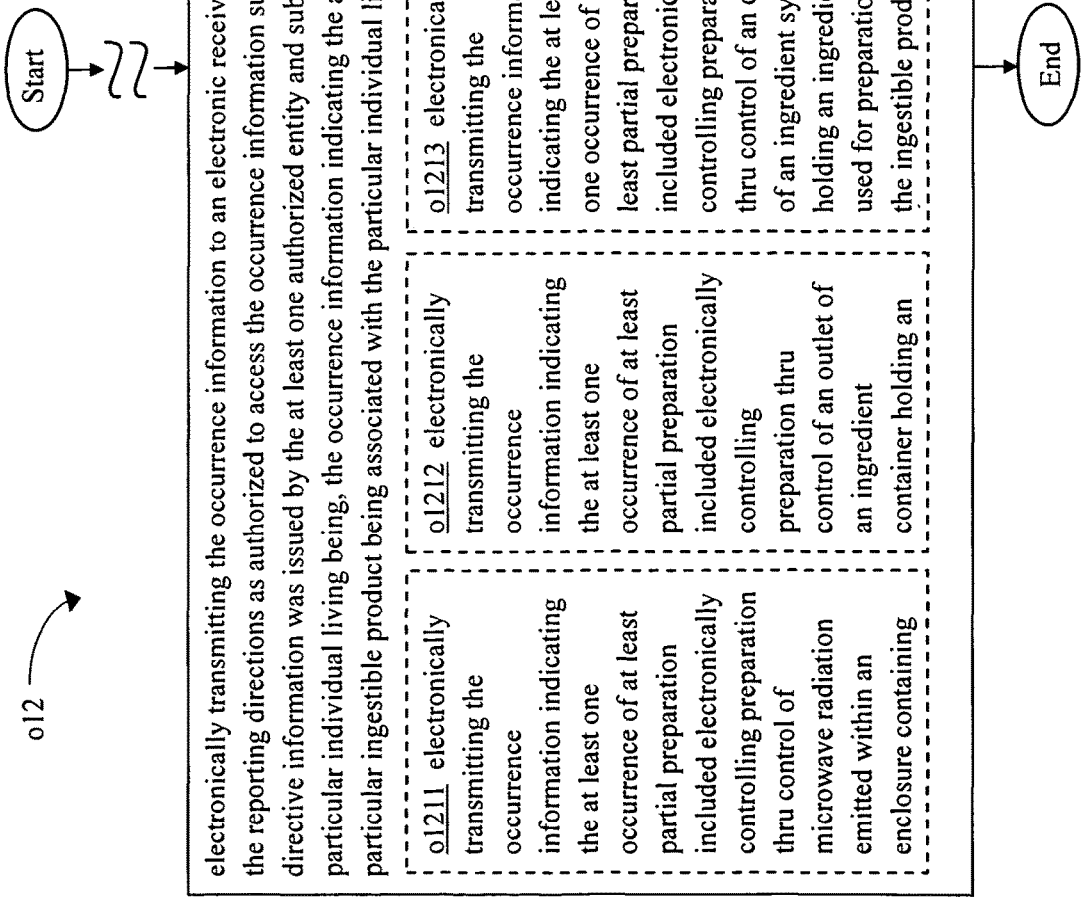
FIG. 44 is a high-level flowchart including exemplary implementations of operation O12 of FIG. 28.

In one or more implementations, as shown in FIG. 44, operation o12 includes an operation o1211 for electronically transmitting the occurrence information indicating the at least one occurrence of at least partial preparation included electronically controlling preparation thru control of microwave radiation emitted within an enclosure containing ingredients to be used for preparation of the ingestible product. An exemplary version of the non-transitory signal bearing medium n100 is depicted as bearing one or more transmit control prep microwave instructions i1211 that when executed will direct performance of the operation o1211. In an implementation, the one or more transmit control prep microwave instructions i1211 when executed direct electronically transmitting the occurrence information indicating the at least one occurrence of at least partial preparation included electronically controlling preparation thru control of microwave radiation emitted within an enclosure containing ingredients to be used for preparation of the ingestible product (e.g. the transceiver component s522 is configured to transmit the occurrence information indicating the at least one occurrence of at least partial preparation including an implementation of the processor component s102 is configured to electronically control the microwave component s706 according to a temperature profile included in the directive information, etc.). Furthermore, the transmit control prep microwave electrical circuitry arrangement e1211 when activated will perform the operation o1211. In an implementation, the transmit control prep microwave electrical circuitry arrangement e1211, when activated performs electronically transmitting the occurrence information indicating the at least one occurrence of at least partial preparation included electronically controlling preparation thru control of microwave radiation emitted within an enclosure containing ingredients to be used for preparation of the ingestible product (e.g. the transceiver component s522 is configured to transmit the occurrence information indicating the at least one occurrence of at least partial preparation including an implementation of the processor component s102 is configured to electronically control the microwave component s706 according to a temperature profile included in the directive information, etc.). In an implementation, the electronically transmitting the occurrence information indicating the at least one occurrence of at least partial preparation included electronically controlling preparation thru control of microwave radiation emitted within an enclosure containing ingredients to be used for preparation of the ingestible product is carried out by electronically transmitting the occurrence information indicating the at least one occurrence of at least partial preparation included electronically controlling preparation thru control of microwave radiation emitted within an enclosure containing ingredients to be used for preparation of the ingestible product (e.g. the transceiver component s522 is configured to transmit the occurrence information indicating the at least one occurrence of at least partial preparation including an implementation of the processor component s102 is configured to electronically control the microwave component s706 according to a temperature profile included in the directive information, etc.).

In one or more implementations, operation o12 includes an operation o1212 for electronically transmitting the occurrence information indicating the at least one occurrence of at least partial preparation included electronically controlling preparation thru control of an outlet of an ingredient container holding an ingredient used for preparation of the ingestible product. An exemplary version of the non-transitory signal bearing medium n100 is depicted as bearing one or more transmit control prep container instructions i1212 that when executed will direct performance of the operation o1212. In an implementation, the one or more transmit control prep container instructions i1212 when executed direct electronically transmitting the occurrence information indicating the at least one occurrence of at least partial preparation included electronically controlling preparation thru control of an outlet of an ingredient container holding an ingredient used for preparation of the ingestible product (e.g. the transmitter component s526 is configured to transmit the occurrence information indicating the at least one occurrence of at least partial preparation including an implementation of the processor component s102 is configured to electronically control an outlet of the material storage component s734 configured as an ingredient container according to an access profile included in the directive information, etc.). Furthermore, the transmit control prep container electrical circuitry arrangement e1212 when activated will perform the operation o1212. In an implementation, the transmit control prep container electrical circuitry arrangement e1212, when activated performs electronically transmitting the occurrence information indicating the at least one occurrence of at least partial preparation included electronically controlling preparation thru control of an outlet of an ingredient container holding an ingredient used for preparation of the ingestible product (e.g. the transmitter component s526 is configured to transmit the occurrence information indicating the at least one occurrence of at least partial preparation including an implementation of the processor component s102 is configured to electronically control an outlet of the material storage component s734 configured as an ingredient container according to an access profile included in the directive information, etc.). In an implementation, the electronically transmitting the occurrence information indicating the at least one occurrence of at least partial preparation included electronically controlling preparation thru control of an outlet of an ingredient container holding an ingredient used for preparation of the ingestible product is carried out by electronically transmitting the occurrence information indicating the at least one occurrence of at least partial preparation included electronically controlling preparation thru control of an outlet of an ingredient container holding an ingredient used for preparation of the ingestible product (e.g. the transmitter component s526 is configured to transmit the occurrence information indicating the at least one occurrence of at least partial preparation including an implementation of the processor component s102 is configured to electronically control an outlet of the material storage component s734 configured as an ingredient container according to an access profile included in the directive information, etc.).

In one or more implementations, operation o12 includes an operation o1213 for electronically transmitting the occurrence information indicating the at least one occurrence of at least partial preparation included electronically controlling preparation thru control of an outlet of an ingredient syringe holding an ingredient used for preparation of the ingestible product. An exemplary version of the non-transitory signal bearing medium n100 is depicted as bearing one or more transmit control prep syringe instructions i1213 that when executed will direct performance of the operation o1213. In an implementation, the one or more transmit control prep syringe instructions i1213 when executed direct electronically transmitting the occurrence information indicating the at least one occurrence of at least partial preparation included electronically controlling preparation thru control of an outlet of an ingredient syringe holding an ingredient used for preparation of the ingestible product (e.g. the internet network component s502 is configured to transmit the occurrence information indicating the at least one occurrence of at least partial preparation including an implementation of the processor component s102 is configured to electronically control an outlet of the material storage component s734 configured as an ingredient syringe according to an access profile included in the directive information, etc.). Furthermore, the transmit control prep syringe electrical circuitry arrangement e1213 when activated will perform the operation o1213. In an implementation, the transmit control prep syringe electrical circuitry arrangement e1213, when activated performs electronically transmitting the occurrence information indicating the at least one occurrence of at least partial preparation included electronically controlling preparation thru control of an outlet of an ingredient syringe holding an ingredient used for preparation of the ingestible product (e.g. the internet network component s502 is configured to transmit the occurrence information indicating the at least one occurrence of at least partial preparation including an implementation of the processor component s102 is configured to electronically control an outlet of the material storage component s734 configured as an ingredient syringe according to an access profile included in the directive information, etc.). In an implementation, the electronically transmitting the occurrence information indicating the at least one occurrence of at least partial preparation included electronically controlling preparation thru control of an outlet of an ingredient syringe holding an ingredient used for preparation of the ingestible product is carried out by electronically transmitting the occurrence information indicating the at least one occurrence of at least partial preparation included electronically controlling preparation thru control of an outlet of an ingredient syringe holding an ingredient used for preparation of the ingestible product (e.g. the internet network component s502 is configured to transmit the occurrence information indicating the at least one occurrence of at least partial preparation including an implementation of the processor component s102 is configured to electronically control an outlet of the material storage component s734 configured as an ingredient syringe according to an access profile included in the directive information, etc.).

In one or more implementations, operation o12 includes an operation o1214 for electronically transmitting the occurrence information indicating the at least one occurrence of at least partial preparation included electronically controlling preparation thru control of mixing of at least some of the ingredients used to prepare the ingestible product before thermal treatment of the ingredients. An exemplary version of the non-transitory signal bearing medium n100 is depicted as bearing one or more transmit control prep mix before thermal instructions i1214 that when executed will direct performance of the operation o1214. In an implementation, the one or more transmit control prep mix before thermal-instructions i1214 when executed direct electronically controlling preparation thru control of mixing of at least some of the ingredients used to prepare the ingestible product before thermal treatment of the ingredients (e.g. the optical network component s504 is configured to transmit the occurrence information indicating the at least one occurrence of at least partial preparation including an implementation of the processor component s102 is configured to electronically control the mixer component s716 according to a mixing profile included in the directive information, etc.). Furthermore, the transmit control prep mix before thermal electrical circuitry arrangement e1214 when activated will perform the operation o1214. In an implementation, the transmit control prep mix before thermal electrical circuitry arrangement e1214, when activated performs electronically controlling preparation thru control of mixing of at least some of the ingredients used to prepare the ingestible product before thermal treatment of the ingredients (e.g. the optical network component s504 is configured to transmit the occurrence information indicating the at least one occurrence of at least partial preparation including an implementation of the processor component s102 is configured to electronically control the mixer component s716 according to a mixing profile included in the directive information, etc.). In an implementation, the electronically transmitting the occurrence information indicating the at least one occurrence of at least partial preparation included electronically controlling preparation thru control of mixing of at least some of the ingredients used to prepare the ingestible product before thermal treatment of the ingredients is carried out by electronically controlling preparation thru control of mixing of at least some of the ingredients used to prepare the ingestible product before thermal treatment of the ingredients (e.g. the optical network component s504 is configured to transmit the occurrence information indicating the at least one occurrence of at least partial preparation including an implementation of the processor component s102 is configured to electronically control the mixer component s716 according to a mixing profile included in the directive information, etc.).

In one or more implementations, operation o12 includes an operation o1215 for electronically transmitting the occurrence information indicating the at least one occurrence of at least partial preparation included electronically controlling preparation thru control of blending of at least some of the ingredients used to prepare the ingestible product after thermal treatment of the ingredients. An exemplary version of the non-transitory signal bearing medium n100 is depicted as bearing one or more transmit control prep re mix after thermal instructions i1215 that when executed will direct performance of the operation o1215. In an implementation, the one or more transmit control prep re mix after thermal instructions i1215 when executed direct electronically transmitting the occurrence information indicating the at least one occurrence of at least partial preparation included electronically controlling preparation thru control of blending of at least some of the ingredients used to prepare the ingestible product after thermal treatment of the ingredients (e.g. the waveguide network component s506 is configured to transmit the occurrence information indicating the at least one occurrence of at least partial preparation including an implementation of the processor component s102 is configured to electronically control the blending component s714 according to a blending profile involving some of the ingredients used to prepare the ingestible product included in the directive information, etc.). Furthermore, the transmit control prep re mix after thermal electrical circuitry arrangement e1215 when activated will perform the operation o1215. In an implementation, the transmit control prep re mix after thermal electrical circuitry arrangement e1215, when activated performs electronically transmitting the occurrence information indicating the at least one occurrence of at least partial preparation included electronically controlling preparation thru control of blending of at least some of the ingredients used to prepare the ingestible product after thermal treatment of the ingredients (e.g. the waveguide network component s506 is configured to transmit the occurrence information indicating the at least one occurrence of at least partial preparation including an implementation of the processor component s102 is configured to electronically control the blending component s714 according to a blending profile involving some of the ingredients used to prepare the ingestible product included in the directive information, etc.). In an implementation, the electronically transmitting the occurrence information indicating the at least one occurrence of at least partial preparation included electronically controlling preparation thru control of blending of at least some of the ingredients used to prepare the ingestible product after thermal treatment of the ingredients is carried out by electronically transmitting the occurrence information indicating the at least one occurrence of at least partial preparation included electronically controlling preparation thru control of blending of at least some of the ingredients used to prepare the ingestible product after thermal treatment of the ingredients (e.g. the waveguide network component s506 is configured to transmit the occurrence information indicating the at least one occurrence of at least partial preparation including an implementation of the processor component s102 is configured to electronically control the blending component s714 according to a blending profile involving some of the ingredients used to prepare the ingestible product included in the directive information, etc.).

Figure 45:
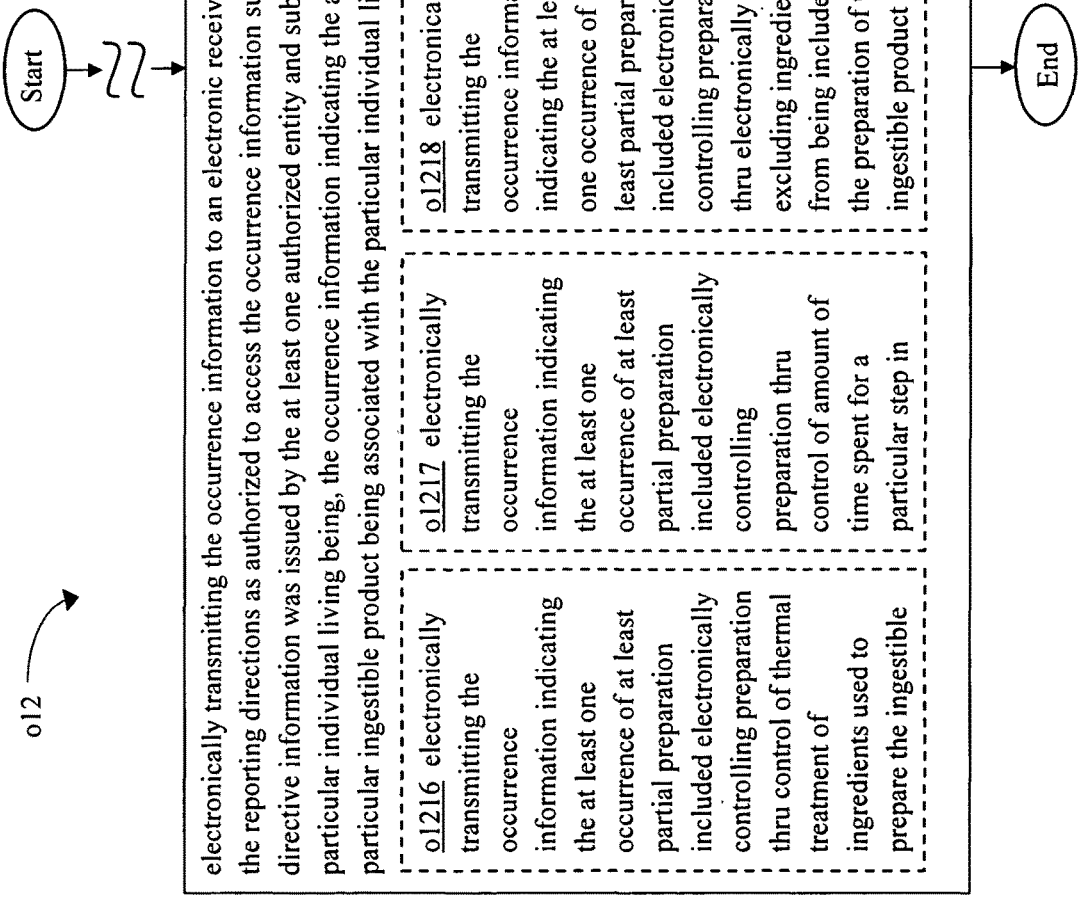
FIG. 45 is a high-level flowchart including exemplary implementations of operation O12 of FIG. 28.

In one or more implementations, as shown in FIG. 45, operation o12 includes an operation o1216 for electronically transmitting the occurrence information indicating the at least one occurrence of at least partial preparation included electronically controlling preparation thru control of thermal treatment of ingredients used to prepare the ingestible product, the thermal treatment including heating, cooling, or a combination thereof of the ingredients. An exemplary version of the non-transitory signal bearing medium n100 is depicted as bearing one or more transmit control prep heating cooling instructions i1216 that when executed will direct performance of the operation o1216. In an implementation, the one or more transmit control prep heating cooling instructions i1216 when executed direct electronically transmitting the occurrence information indicating the at least one occurrence of at least partial preparation included electronically controlling preparation thru control of thermal treatment of ingredients used to prepare the ingestible product, the thermal treatment including heating, cooling, or a combination thereof of the ingredients (e.g. the internet network component s508 is configured to transmit the occurrence information indicating the at least one occurrence of at least partial preparation including an implementation of the processor component s102 is configured to electronically control the heating component s702 and/or the cooling component s704 according to a thermal profile included in the directive information, etc.). Furthermore, the transmit control prep heating cooling electrical circuitry arrangement e1216 when activated will perform the operation o1216. In an implementation, the transmit control prep heating cooling electrical circuitry arrangement e1216, when activated performs electronically transmitting the occurrence information indicating the at least one occurrence of at least partial preparation included electronically controlling preparation thru control of thermal treatment of ingredients used to prepare the ingestible product, the thermal treatment including heating, cooling, or a combination thereof of the ingredients (e.g. the internet network component s508 is configured to transmit the occurrence information indicating the at least one occurrence of at least partial preparation including an implementation of the processor component s102 is configured to electronically control the heating component s702 and/or the cooling component s704 according to a thermal profile included in the directive information, etc.). In an implementation, the electronically transmitting the occurrence information indicating the at least one occurrence of at least partial preparation included electronically controlling preparation thru control of thermal treatment of ingredients used to prepare the ingestible product, the thermal treatment including heating, cooling, or a combination thereof of the ingredients is carried out by electronically transmitting the occurrence information indicating the at least one occurrence of at least partial preparation included electronically controlling preparation thru control of thermal treatment of ingredients used to prepare the ingestible product, the thermal treatment including heating, cooling, or a combination thereof of the ingredients (e.g. the internet network component s508 is configured to transmit the occurrence information indicating the at least one occurrence of at least partial preparation including an implementation of the processor component s102 is configured to electronically control the heating component s702 and/or the cooling component s704 according to a thermal profile included in the directive information, etc.).

In one or more implementations, operation o12 includes an operation o1217 for electronically transmitting the occurrence information indicating the at least one occurrence of at least partial preparation included electronically controlling preparation thru control of amount of time spent for a particular step in preparation of the ingestible product. An exemplary version of the non-transitory signal bearing medium n100 is depicted as bearing one or more transmit control prep time control instructions i1217 that when executed will direct performance of the operation o1217. In an implementation, the one or more transmit control prep time control instructions i1217 when executed direct electronically transmitting the occurrence information indicating the at least one occurrence of at least partial preparation included electronically controlling preparation thru control of amount of time spent for a particular step in preparation of the ingestible product (e.g. the wireless network component s510 is configured to transmit the occurrence information indicating the at least one occurrence of at least partial preparation including an implementation of the processor component s102 is configured to electronically control components of the material processing subsystem s700 based upon an internal clock of the processor according to a time profile included in the directive information, etc.). Furthermore, the transmit control prep time control electrical circuitry arrangement e1217 when activated will perform the operation o1217. In an implementation, the transmit control prep time control electrical circuitry arrangement e1217, when activated performs electronically transmitting the occurrence information indicating the at least one occurrence of at least partial preparation included electronically controlling preparation thru control of amount of time spent for a particular step in preparation of the ingestible product (e.g. the wireless network component s510 is configured to transmit the occurrence information indicating the at least one occurrence of at least partial preparation including an implementation of the processor component s102 is configured to electronically control components of the material processing subsystem s700 based upon an internal clock of the processor according to a time profile included in the directive information, etc.). In an implementation, the electronically transmitting the occurrence information indicating the at least one occurrence of at least partial preparation included electronically controlling preparation thru control of amount of time spent for a particular step in preparation of the ingestible product is carried out by electronically transmitting the occurrence information indicating the at least one occurrence of at least partial preparation included electronically controlling preparation thru control of amount of time spent for a particular step in preparation of the ingestible product (e.g. the wireless network component s510 is configured to transmit the occurrence information indicating the at least one occurrence of at least partial preparation including an implementation of the processor component s102 is configured to electronically control components of the material processing subsystem s700 based upon an internal clock of the processor according to a time profile included in the directive information, etc.).

In one or more implementations, operation o12 includes an operation o1218 for electronically transmitting the occurrence information indicating the at least one occurrence of at least partial preparation included electronically controlling preparation thru electronically excluding ingredients from being included in the preparation of the ingestible product. An exemplary version of the non-transitory signal bearing medium n100 is depicted as bearing one or more transmit control prep ingredient exclusion instructions i1218 that when executed will direct performance of the operation o1218. In an implementation, the one or more transmit control prep ingredient exclusion instructions i1218 when executed direct electronically transmitting the occurrence information indicating the at least one occurrence of at least partial preparation included electronically controlling preparation thru electronically excluding ingredients from being included in the preparation of the ingestible product (e.g. the wired network component s512 is configured to transmit the occurrence information indicating the at least one occurrence of at least partial preparation including an implementation of the processor component s102 is configured to electronically control the sorting component s728 to exclude one or more ingredients from being included in the ingestible product according to an exclusion profile included in the directive information, etc.). Furthermore, the transmit control prep ingredient exclusion electrical circuitry arrangement e1218 when activated will perform the operation o1218. In an implementation, the transmit control prep ingredient exclusion electrical circuitry arrangement e1218, when activated performs electronically transmitting the occurrence information indicating the at least one occurrence of at least partial preparation included electronically controlling preparation thru electronically excluding ingredients from being included in the preparation of the ingestible product (e.g. the wired network component s512 is configured to transmit the occurrence information indicating the at least one occurrence of at least partial preparation including an implementation of the processor component s102 is configured to electronically control the sorting component s728 to exclude one or more ingredients from being included in the ingestible product according to an exclusion profile included in the directive information, etc.). In an implementation, the electronically transmitting the occurrence information indicating the at least one occurrence of at least partial preparation included electronically controlling preparation thru electronically excluding ingredients from being included in the preparation of the ingestible product is carried out by electronically transmitting the occurrence information indicating the at least one occurrence of at least partial preparation included electronically controlling preparation thru electronically excluding ingredients from being included in the preparation of the ingestible product (e.g. the wired network component s512 is configured to transmit the occurrence information indicating the at least one occurrence of at least partial preparation including an implementation of the processor component s102 is configured to electronically control the sorting component s728 to exclude one or more ingredients from being included in the ingestible product according to an exclusion profile included in the directive information, etc.).

In one or more implementations, operation o12 includes an operation o1219 for electronically transmitting the occurrence information indicating the at least one occurrence of at least partial preparation included electronically controlling preparation thru electronically including ingredients in the preparation of the ingestible product. An exemplary version of the non-transitory signal bearing medium n100 is depicted as bearing one or more transmit control prep ingredient inclusion instructions i1219 that when executed will direct performance of the operation o1219. In an implementation, the one or more transmit control prep ingredient inclusion instructions i1219 when executed direct electronically transmitting the occurrence information indicating the at least one occurrence of at least partial preparation included electronically controlling preparation thru electronically including ingredients in the preparation of the ingestible product (e.g. the cellular network component s514 is configured to transmit the occurrence information indicating the at least one occurrence of at least partial preparation including an implementation of the processor component s102 is configured to electronically control the sorting component s728 to include one or more ingredients in the ingestible product according to an inclusion profile included in the directive information, etc.). Furthermore, the transmit control prep ingredient inclusion electrical circuitry arrangement e1219 when activated will perform the operation o1219. In an implementation, the transmit control prep ingredient inclusion electrical circuitry arrangement e1219, when activated performs electronically transmitting the occurrence information indicating the at least one occurrence of at least partial preparation included electronically controlling preparation thru electronically including ingredients in the preparation of the ingestible product (e.g. the cellular network component s514 is configured to transmit the occurrence information indicating the at least one occurrence of at least partial preparation including an implementation of the processor component s102 is configured to electronically control the sorting component s728 to include one or more ingredients in the ingestible product according to an inclusion profile included in the directive information, etc.). In an implementation, the electronically transmitting the occurrence information indicating the at least one occurrence of at least partial preparation included electronically controlling preparation thru electronically including ingredients in the preparation of the ingestible product is carried out by electronically transmitting the occurrence information indicating the at least one occurrence of at least partial preparation included electronically controlling preparation thru electronically including ingredients in the preparation of the ingestible product (e.g. the cellular network component s514 is configured to transmit the occurrence information indicating the at least one occurrence of at least partial preparation including an implementation of the processor component s102 is configured to electronically control the sorting component s728 to include one or more ingredients in the ingestible product according to an inclusion profile included in the directive information, etc.).

In one or more implementations, operation o12 includes an operation o1220 for electronically transmitting the occurrence information indicating the at least one occurrence of at least partial preparation of the particular ingestible product as being associated with the particular individual living being as a human being. A non-transitory signal bearing medium includes one or more transmit living being as human instructions i1220 that when executed will direct performance of the operation o1220. In an implementation, the one or more transmit living being as human instructions i1220 when executed direct electronically transmitting (e.g., the internet network component s508 is configured to transmit the occurrence information indicating the at least one occurrence of at least partial preparation, etc.) the occurrence information indicating the at least one occurrence of at least partial preparation of the particular ingestible product as being associated with the particular individual living being as a human being (e.g. the occurrence information indicates that the particular ingestible product is prepared as a electrolyte replacement drink for an exercising human athlete, etc.). Furthermore, the transmit living being as human electrical circuitry arrangement e1220 when activated will perform the operation o1220. In an implementation, the transmit living being as human electrical circuitry arrangement e1220, when activated performs electronically transmitting (e.g., the internet network component s508 is configured to transmit the occurrence information indicating the at least one occurrence of at least partial preparation, etc.) the occurrence information indicating the at least one occurrence of at least partial preparation of the particular ingestible product as being associated with the particular individual living being as a human being (e.g. the occurrence information indicates that the particular ingestible product is prepared as a electrolyte replacement drink for an exercising human athlete, etc.). In an implementation, the electronically transmitting the occurrence information indicating the at least one occurrence of at least partial preparation of the particular ingestible product as being associated with the particular individual living being as a human being is carried out by electronically transmitting (e.g., the internet network component s508 is configured to transmit the occurrence information indicating the at least one occurrence of at least partial preparation, etc.) the occurrence information indicating the at least one occurrence of at least partial preparation of the particular ingestible product as being associated with the particular individual living being as a human being (e.g. the occurrence information indicates that the particular ingestible product is prepared as a electrolyte replacement drink for an exercising human athlete, etc.).

Figure 46:
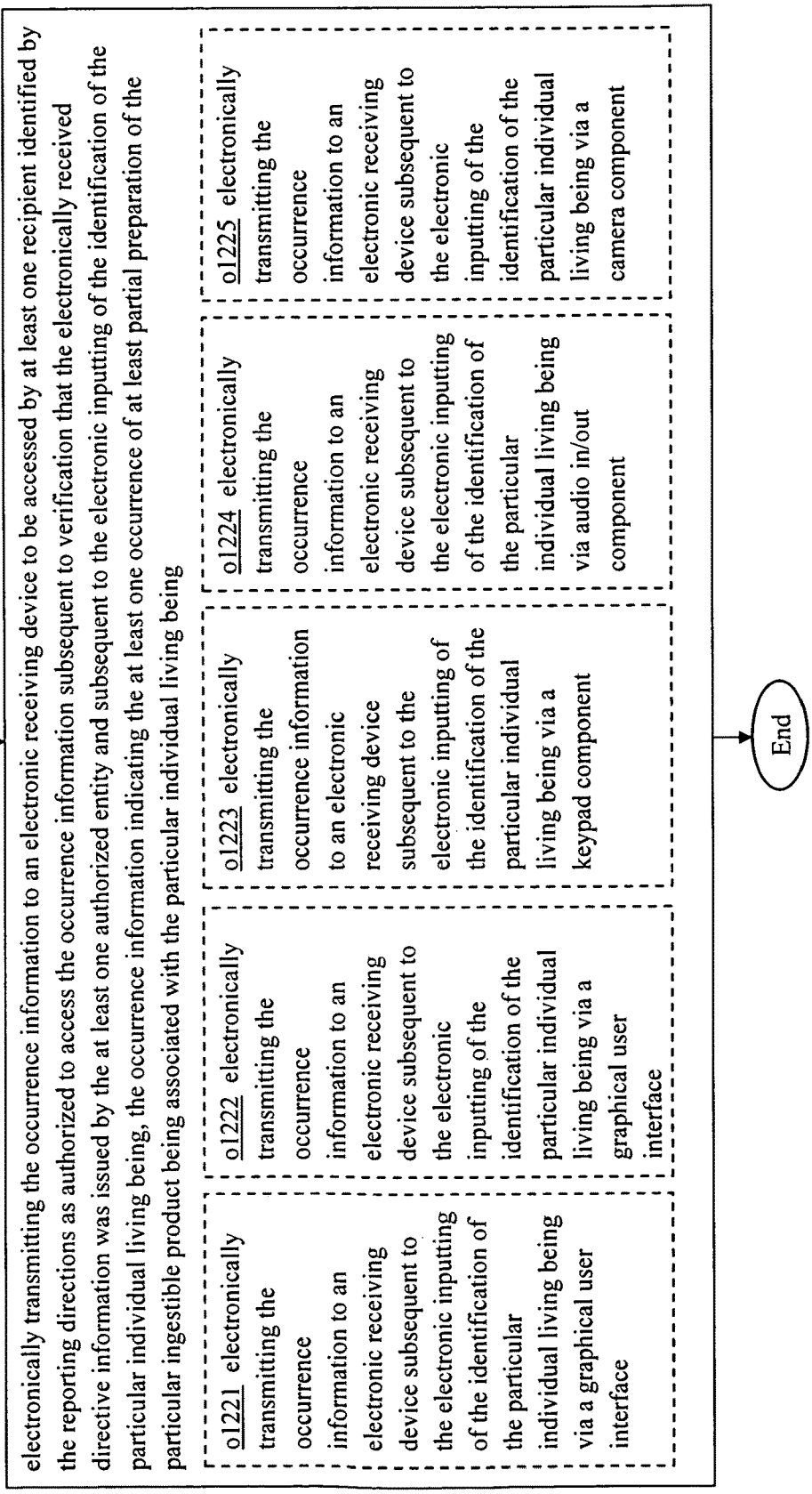
FIG. 46 is a high-level flowchart including exemplary implementations of operation O12 of FIG. 28.

In one or more implementations, as shown in FIG. 46, operation o12 includes an operation o1221 for electronically transmitting the occurrence information to an electronic receiving device subsequent to the electronic inputting of the identification of the particular individual living being via a graphical user interface. A non-transitory signal bearing medium includes one or more transmit input gui instructions i1221 that when executed will direct performance of the operation o1221. In an implementation, the one or more transmit input gui instructions i1221 when executed direct electronically transmitting (e.g. the optical network component s504 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.). Furthermore, the transmit input gui electrical circuitry arrangement e1221 when activated will perform the operation o1221. In an implementation, the transmit input gui electrical circuitry arrangement e1221, when activated performs electronically transmitting (e.g. the optical network component s504 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.). In an implementation, the electronically transmitting the occurrence information to an electronic receiving device subsequent to the electronic inputting of the identification of the particular individual living being via a graphical user interface is carried out by electronically transmitting (e.g. the optical network component s504 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.).

In one or more implementations, operation o12 includes an operation o1222 for electronically transmitting the occurrence information to an electronic receiving device subsequent to the electronic inputting of the identification of the particular individual living being via a graphical user interface. A non-transitory signal bearing medium includes one or more transmit subsequent gui instructions i1222 that when executed will direct performance of the operation o1222. In an implementation, the one or more transmit subsequent gui instructions i1222 when executed direct electronically transmitting (e.g. the wireless network component s510 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.). Furthermore, the transmit subsequent gui electrical circuitry arrangement e1222 when activated will perform the operation o1222. In an implementation, the transmit subsequent gui electrical circuitry arrangement e1222, when activated performs electronically transmitting (e.g. the wireless network component s510 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.). In an implementation, the electronically transmitting the occurrence information to an electronic receiving device subsequent to the electronic inputting of the identification of the particular individual living being via a graphical user interface is carried out by electronically transmitting (e.g. the wireless network component s510 is configured to transmit the occurrence information indicating the at least one occurrence of at least partial preparation, etc.) the occurrence information to an electronic receiving device subsequent to the electronic inputting of the identification of the particular individual living being via a graphical user interface (e.g. a human inputs identification information via the graphical user interface component s302, etc.).

In one or more implementations, operation o12 includes an operation o1223 for electronically transmitting the occurrence information to an electronic receiving device subsequent to the electronic inputting of the identification of the particular individual living being via a keypad component. A non-transitory signal bearing medium includes one or more transmit subsequent keypad instructions i1223 that when executed will direct performance of the operation o1223. In an implementation, the one or more transmit subsequent keypad instructions i1223 when executed direct electronically transmitting (e.g. the wired network component s512 is configured to transmit the occurrence information indicating the at least one occurrence of at least partial preparation, etc.) the occurrence information to an electronic receiving device subsequent to the electronic inputting of the identification of the particular individual living being via a keypad component (e.g. a human inputs identification information via the keyboard component s306, etc.). Furthermore, the transmit subsequent keypad electrical circuitry arrangement e1223 when activated will perform the operation o1223. In an implementation, the transmit subsequent keypad electrical circuitry arrangement e1223, when activated performs electronically transmitting (e.g. the wired network component s512 is configured to transmit the occurrence information indicating the at least one occurrence of at least partial preparation, etc.) the occurrence information to an electronic receiving device subsequent to the electronic inputting of the identification of the particular individual living being via a keypad component (e.g. a human inputs identification information via the keyboard component s306, etc.). In an implementation, the electronically transmitting, the occurrence information to an electronic receiving device subsequent to the electronic inputting of the identification of the particular individual living being via a keypad component is carried out by electronically transmitting (e.g. the wired network component s512 is configured to transmit the occurrence information indicating the at least one occurrence of at least partial preparation, etc.) the occurrence information to an electronic receiving device subsequent to the electronic inputting of the identification of the particular individual living being via a keypad component (e.g. a human inputs identification information via the keyboard component s306, etc.).

In one or more implementations, operation o12 includes an operation o1224 for electronically transmitting the occurrence information to an electronic receiving device subsequent to the electronic inputting of the identification of the particular individual living being via audio in/out component. A non-transitory signal bearing medium includes one or more transmit subsequent audio instructions i1224 that when executed will direct performance of the operation o1224. In an implementation, the one or more transmit subsequent audio instructions i1224 when executed direct electronically transmitting (e.g. the cellular network component s514 is configured to transmit the occurrence information indicating the at least one occurrence of at least partial preparation, etc.) the occurrence information to an electronic receiving device subsequent to the electronic inputting of the identification of the particular individual living being via audio in/out component (e.g. a human inputs identification information via the audio in/out component s328, etc.). Furthermore, the transmit subsequent audio electrical circuitry arrangement e1224 when activated will perform the operation o1224. In an implementation, the transmit subsequent audio electrical circuitry arrangement e1224, when activated performs electronically transmitting (e.g. the cellular network component s514 is configured to transmit the occurrence information indicating the at least one occurrence of at least partial preparation, etc.) the occurrence information to an electronic receiving device subsequent to the electronic inputting of the identification of the particular individual living being via audio in/out component (e.g. a human inputs identification information via the audio in/out component s328, etc.). In an implementation, the electronically transmitting the occurrence information to an electronic receiving device subsequent to the electronic inputting of the identification of the particular individual living being via audio in/out component is carried out by electronically transmitting (e.g. the cellular network component s514 is configured to transmit the occurrence information indicating the at least one occurrence of at least partial preparation, etc.) the occurrence information to an electronic receiving device subsequent to the electronic inputting of the identification of the particular individual living being via audio in/out component (e.g. a human inputs identification information via the audio in/out component s328, etc.).

In one or more implementations, operation o12 includes an operation o1225 for electronically transmitting the occurrence information to an electronic receiving device subsequent to the electronic inputting of the identification of the particular individual living being via a camera component. A non-transitory signal bearing medium includes one or more transmit subsequent camera instructions i1225 that when executed will direct performance of the operation o1225. In an implementation, the one or more transmit subsequent camera instructions i1225 when executed direct electronically transmitting (e.g. the wide area network component s516 is configured to transmit the occurrence information indicating the at least one occurrence of at least partial preparation, etc.) the occurrence information to an electronic receiving device subsequent to the electronic inputting of the identification of the particular individual living being via a camera component (e.g. a human inputs identification information via the camera component s336, etc.). Furthermore, the transmit subsequent camera electrical circuitry arrangement e1225 when activated will perform the operation o1225. In an implementation, the transmit subsequent camera electrical circuitry arrangement e1225, when activated performs electronically transmitting (e.g. the wide area network component s516 is configured to transmit the occurrence information indicating the at least one occurrence of at least partial preparation, etc.) the occurrence information to an electronic receiving device subsequent to the electronic inputting of the identification of the particular individual living being via a camera component (e.g. a human inputs identification information via the camera component s336, etc.). In an implementation, the electronically transmitting the occurrence information to an electronic receiving device subsequent to the electronic inputting of the identification of the particular individual living being via a camera component is carried out by electronically transmitting (e.g. the wide area network component s516 is configured to transmit the occurrence information indicating the at least one occurrence of at least partial preparation, etc.) the occurrence information to an electronic receiving device subsequent to the electronic inputting of the identification of the particular individual living being via a camera component (e.g. a human inputs identification information via the camera component s336, etc.).

Figure 47:
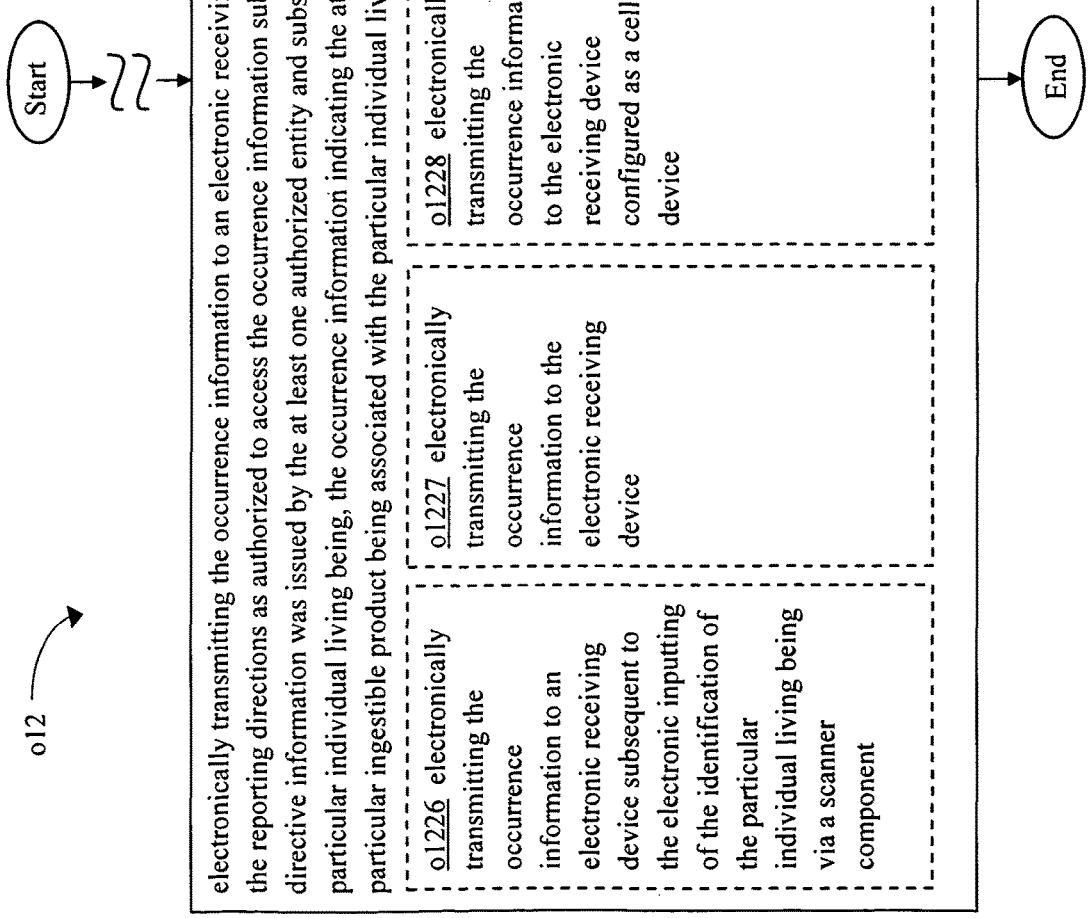
FIG. 47 is a high-level flowchart including exemplary implementations of operation O12 of FIG. 28.

In one or more implementations, as shown in FIG. 47, operation o12 includes an operation o1226 for electronically transmitting the occurrence information to an electronic receiving device subsequent to the electronic inputting of the identification of the particular individual living being via a scanner component. A non-transitory signal bearing medium includes one or more transmit subsequent scanner instructions i1226 that when executed will direct performance of the operation o1226. In an implementation, the one or more transmit subsequent scanner instructions i1226 when executed direct electronically transmitting (e.g. the local area network component s518 is configured to transmit the occurrence information indicating the at least one occurrence of at least partial preparation, etc.) the occurrence information to an electronic receiving device subsequent to the electronic inputting of the identification of the particular individual living being via a scanner component (e.g. a human inputs identification information via the scanner component s338, etc.). Furthermore, the transmit subsequent scanner electrical circuitry arrangement e1226 when activated will perform the operation o1226. In an implementation, the transmit subsequent scanner electrical circuitry arrangement e1226, when activated performs electronically transmitting (e.g. the local area network component s518 is configured to transmit the occurrence information indicating the at least one occurrence of at least partial preparation, etc.) the occurrence information to an electronic receiving device subsequent to the electronic inputting of the identification of the particular individual living being via a scanner component (e.g. a human inputs identification information via the scanner component s338, etc.). In an implementation, the electronically transmitting the occurrence information to an electronic receiving device subsequent to the electronic inputting of the identification of the particular individual living being via a scanner component is carried out by electronically transmitting (e.g. the local area network component s518 is configured to transmit the occurrence information indicating the at least one occurrence of at least partial preparation, etc.) the occurrence information to an electronic receiving device subsequent to the electronic inputting of the identification of the particular individual living being via a scanner component (e.g. a human inputs identification information via the scanner component s338, etc.).

In one or more implementations, operation o12 includes an operation o1227 for electronically transmitting the occurrence information to the electronic receiving device. A non-transitory signal bearing medium includes one or more transmit to computer instructions i1227 that when executed will direct performance of the operation o1227. In an implementation, the one or more transmit to computer instructions i1227 when executed direct electronically transmitting (e.g. the encrypted communication component s520 is configured to transmit the occurrence information indicating the at least one occurrence of at least partial preparation, etc.) the occurrence information to the electronic receiving device configured as a networked computer (e.g. the communication component s520 is configured to transmit the occurrence information in a format to be received by the electronic receiving device as a networked computer, etc.). Furthermore, the transmit to computer electrical circuitry arrangement e1227 when activated will perform the operation o1227. In an implementation, the transmit to computer electrical circuitry arrangement e1227, when activated performs electronically transmitting (e.g. the encrypted communication component s520 is configured to transmit the occurrence information indicating the at least one occurrence of at least partial preparation, etc.) the occurrence information to the electronic receiving device configured as a networked computer (e.g. the communication component s520 is configured to transmit the occurrence information in a format to be received by the electronic receiving device as a networked computer, etc.). In an implementation, the electronically transmitting the occurrence information to the electronic receiving device is carried out by electronically transmitting (e.g. the encrypted communication component s520 is configured to transmit the occurrence information indicating the at least one occurrence of at least partial preparation, etc.) the occurrence information to the electronic receiving device configured as a networked computer (e.g. the communication component s520 is configured to transmit the occurrence information in a format to be received by the electronic receiving device as a networked computer, etc.).

In one or more implementations, operation o12 includes an operation o1228 for electronically transmitting the occurrence information to the electronic receiving device configured as a cellular device. A non-transitory signal bearing medium includes one or more transmit to cellular instructions i1228 that when executed will direct performance of the operation o1228. In an implementation, the one or more transmit to cellular instructions i1228 when executed direct electronically transmitting (e.g. the transceiver component s522 is configured to transmit the occurrence information indicating the at least one occurrence of at least partial preparation, etc.) the occurrence information to the electronic receiving device configured as a cellular device (e.g. the communication component s520 is configured to transmit the occurrence information in a format to be received by the electronic receiving device as a cellular device, etc.). Furthermore, the transmit to cellular electrical circuitry arrangement e1228 when activated will perform the operation o1228. In an implementation, the transmit to cellular electrical circuitry arrangement e1228, when activated performs electronically transmitting (e.g. the transceiver component s522 is configured to transmit the occurrence information indicating the at least one occurrence of at least partial preparation, etc.) the occurrence information to the electronic receiving device configured as a cellular device (e.g. the communication component s520 is configured to transmit the occurrence information in a format to be received by the electronic receiving device as a cellular device, etc.). In an implementation, the electronically transmitting the occurrence information to the electronic receiving device configured as a cellular device is carried out by electronically transmitting (e.g. the transceiver component s522 is configured to transmit the occurrence information indicating the at least one occurrence of at least partial preparation, etc.) the occurrence information to the electronic receiving device configured as a cellular device (e.g. the communication component s520 is configured to transmit the occurrence information in a format to be received by the electronic receiving device as a cellular device, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (the virtually any combination being limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (the virtually any combination being limited to patentable subject matter under 35 U.S.C. 101) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:
1. A system, comprising:
 a vending machine, including at least:
  at least one production machine configured for preparation of one or more ingestible products incorporating one or more controlled substances;
  at least one processing device; and
  at least one non-transitory computer-readable medium including at least one or more instructions which, when executed by the at least one processing device, configure the at least one processing device as at least:

circuitry configured for receiving at least one identity of at least one particular living being;

circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being;

circuitry configured for obtaining at least one verification of controlled substance directive issuance authorization of the issuer of the directive information;

circuitry configured for obtaining at least one verification of authorship of the directive information by the issuer;

circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship;

circuitry configured for recording occurrence information indicative of the preparation of the at least one particular ingestible product via the at least one production machine; and circuitry configured for controlling at least one dispensing, by the at least one production machine, of the at least one prepared particular ingestible product for collection by the at least one particular living being.

2. The system of claim 1, wherein circuitry configured for receiving at least one identity of at least one particular living being comprises:

circuitry configured for receiving at least one identity of at least one particular living being via a credit card swipe.

3. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being via bar code communication, including at least receiving at least one identification of at least one prescription as the directive information via at least one prescription serial number encoded as at least a portion of at least one bar code.

4. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being subsequent to receiving the at least one identity of the at least one particular living being, the directive information transmitted by at least one computing device operated by the issuer of the directive information via internet communication; and wherein circuitry configured for obtaining at least one verification of controlled substance directive issuance authorization of the issuer of the directive information includes at least:

circuitry configured for transmitting at least one request for verification of controlled substance directive issuance authorization of the issuer of the directive information, including at least transmitting the at least one request for verification via internet communication to at least one computing device other than the at least one computing device operated by the issuer of the directive information.

5. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being via an electronic network.

6. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being as encrypted data.

7. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being wirelessly.

8. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding one or more of at least one computer video file or at least one computer audio file bearing at least one indication of the directive information.

9. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding at least one prescription serial number of at least one prescription designated for the at least one particular living being.

10. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding at least one data image of at least some handwritten text.

11. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding at least one computer text file.

12. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding at least one RFID tag.

13. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being including at least some information regarding at least one holographic image.

14. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being, the directive information including at least some information regarding at least one controlled substance for incorporation in the at least one particular ingestible product for preparation via the at least one production machine, the at least one controlled substance designated by the issuer of the directive information for ingestion by the at least one particular living being.

15. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being, the directive information including at least information regarding at least one herbal substance in addition to the at least one controlled substance for incorporation in the at least one particular ingestible product for preparation via the at least one production machine.

16. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being, the directive information including at least information regarding at least one homeopathic substance in addition to the at least one controlled substance for incorporation in the at least one particular ingestible product for preparation via the at least one production machine.

17. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being, the directive information including at least information regarding at least one nutritional substance in addition to the at least one controlled substance for incorporation in the at least one particular ingestible product for preparation via the at least one production machine.

18. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being, the directive information including at least information regarding at least one controlled substance associated with at least one of an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, or an antineoplastic for incorporation in the at least one particular ingestible product for preparation via the at least one production machine.

19. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being, the directive information including at least information regarding at least one controlled substance associated with at least one of an antipyretic, an antiviral, an anti-ulcer agent, an antidyspeptic, an antacid, a beta blocker, a bronchodilator, a cold treatment, or a corticosteroid for incorporation in the at least one particular ingestible product for preparation via the at least one production machine.

20. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being, the directive information including at least information regarding at least one controlled substance associated with at least one of a hormone, a hypoglycemic, an immunosuppressive, a laxative, a muscle relaxant, a sedative, a tranquilizer, an appetite modulator, or a vitamin for incorporation in the at least one particular ingestible product for preparation via the at least one production machine.

21. The system of claim 1, wherein circuitry configured for receiving at least one identity of at least one particular living being comprises:
    circuitry configured for receiving at least one identity of at least one particular living being via at least one of an electronic identification card, an electronic voice print, or a password.

22. The system of claim 1, wherein circuitry configured for receiving at least one identity of at least one particular living being comprises:
    circuitry configured for receiving at least one identity of at least one particular living being via at least one breathalyzer test.

23. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
    circuitry configured for receiving directive information relating to the at least one particular living being including at least one or more indications of at least one particular ingestible product including at least one controlled substance designated by the issuer of the directive information to be swallowed by the at least one particular living being.

24. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
 circuitry configured for receiving directive information relating to the at least one particular living being including at least one or more indications of at least one particular ingestible product including at least one controlled substance designated by the issuer of the directive information to be inhaled by the at least one particular living being.

25. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
 circuitry configured for receiving directive information relating to the at least one particular living being including at least one or more indications of at least one particular ingestible product including at least one controlled substance designated by the issuer of the directive information to be ingested transdermally by the at least one particular living being.

26. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
 circuitry configured for receiving directive information relating to the at least one particular living being including at least one or more indications of at least one particular ingestible product including at least one controlled substance designated by the issuer of the directive information to be used at least one of in sandwich form, as a smoothie, or as a baked good by the at least one particular living being.

27. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
 circuitry configured for receiving directive information relating to the at least one particular living being including at least one or more indications of at least one particular ingestible product designated by the issuer of the directive information to be used as an assembled concoction by the at least one particular living being.

28. The system of claim 1, wherein circuitry configured for obtaining at least one verification of controlled substance directive issuance authorization of the issuer of the directive information comprises:
 circuitry configured for obtaining at least one verification of the issuer of the directive information being at least one of a medical physician, a naturopathic physician, a chiropractic physician, a physician, a nurse practitioner, a nurse, or a dentist.

29. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:
 circuitry configured for controlling temperature of an enclosure containing one or more ingredients to be used for preparation of the at least one particular ingestible product.

30. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:
 circuitry configured for controlling an amount of ingredient mixing during preparation of the at least one particular ingestible product.

31. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:
 circuitry configured for controlling infrared radiation emitted within an enclosure containing one or more ingredients to be used for preparation of the at least one particular ingestible product.

32. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:

circuitry configured for controlling microwave radiation emitted within an enclosure containing one or more ingredients to be used for preparation of the at least one particular ingestible product.

33. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:

circuitry configured for controlling an outlet of an ingredient container holding an ingredient used for preparation of the at least one particular ingestible product.

34. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:

circuitry configured for controlling mixing of one or more ingredients used to prepare the at least one particular ingestible product.

35. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:

circuitry configured for controlling blending of one or more ingredients used to prepare the at least one particular ingestible product.

36. The system of claim 1, wherein circuitry configured for controlling the at least one production machine to prepare the at least one particular ingestible product, including at least incorporating the at least one controlled substance, based at least partially on (i) the circuitry configured for receiving the at least one identity, (ii) the circuitry configured for receiving the directive information, (iii) the circuitry configured for obtaining the at least one verification of controlled substance directive issuance authorization, and (iv) the circuitry configured for obtaining the at least one verification of authorship comprises:

circuitry configured for controlling an amount of time spent for a particular step in preparation of the at least one particular ingestible product.

37. The system of claim 1, wherein circuitry configured for receiving at least one identity of at least one particular living being comprises:

circuitry configured for receiving at least one identity of at least one particular living being via at least some biometric information.

38. The system of claim 1, wherein circuitry configured for obtaining at least one verification of authorship of the directive information by the issuer comprises:

circuitry configured for verifying the authorship of the directive information based at least partly on biometric information received in association with receiving the directive information, including at least confirming whether the biometric information received in association with receiving the directive information is indicative of the purported issuer of the directive information.

39. The system of claim 1, wherein circuitry configured for obtaining at least one verification of authorship of the directive information by the issuer comprises:

circuitry configured for obtaining at least one verification of authorship of the directive information by the issuer, including at least comparing at least one recording bearing the directive information purportedly issued by a particular issuer with at least one voice print associated with the particular issuer to confirm actual authorship of the directive information by the purported issuer.

40. The system of claim 1, wherein circuitry configured for obtaining at least one verification of controlled substance directive issuance authorization of the issuer of the directive information comprises:

circuitry configured for requesting at least one verification of controlled substance directive issuance authorization of the issuer of the directive information, including at least transmitting an indication of identity of the issuer of the directive to at least one license governing authority to confirm current controlled substance directive issuance authorization by the at least one license governing authority for the issuer of the directive.

41. The system of claim 1, wherein circuitry configured for recording occurrence information indicative of preparation of the at least one particular ingestible product via the at least one production machine comprises:

circuitry configured for transmitting the occurrence information to at least one electronic receiving device accessible by at least one recipient identified within one or more reporting directions of the directive information as authorized to access the occurrence information subsequent to verification of authorship of the directive information by the issuer and subsequent to verification that the issuer of the directive information is authorized for controlled substance directive issuance.

42. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:

circuitry configured for receiving directive information relating to the at least one particular living being, the directive information including at least one or more indications of identity of at least one of a physician or a pharmacist who is an issuer of the directive information and one or more indications of at least one particular ingestible product including at least one controlled substance for preparation via the at least one production machine, the at least one particular ingestible product designated by the at least one of a physician or a pharmacist for ingestion by the at least one particular living being.

43. The system of claim 1, wherein circuitry configured for obtaining at least one verification of controlled substance directive issuance authorization of the issuer of the directive information comprises:
circuitry configured for transmitting to at least one state licensing authority governing issuance of controlled substance directives at least one request for verification that the issuer of the directive information is currently authorized by the at least one state licensing authority to issue controlled substance directives.

44. The system of claim 1, wherein circuitry configured for receiving at least one identity of at least one particular living being comprises:
circuitry configured for receiving at least one identity of at least one particular living being via at least some information contained in a memory circuitry coupled with a medication container.

45. The system of claim 1, wherein circuitry configured for receiving at least one identity of at least one particular living being comprises:
circuitry configured for receiving at least one identity of at least one particular living being via an electronic iris scan of the at least one particular living being.

46. The system of claim 1, wherein circuitry configured for receiving at least one identity of at least one particular living being comprises:
circuitry configured for receiving at least one identity of at least one particular living being via an electronically captured fingerprint image of the at least one particular living being.

47. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
circuitry configured for receiving directive information including one or more indications of at least one particular ingestible product as a carrier of at least one controlled substance for preparation via the at least one production machine.

48. The system of claim 1, wherein circuitry configured for receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being comprises:
circuitry configured for receiving directive information including one or more indications of at least one particular ingestible product designated by the issuer of the directive information for ingestion by the at least one particular living being according to at least one requirement.

49. The system of claim 48, wherein circuitry configured for receiving directive information including one or more indications of at least one particular ingestible product designated by the issuer of the directive information for ingestion by the at least one particular living being according to at least one requirement comprises:
circuitry configured for receiving directive information including one or more indications of at least one particular ingestible product designated by the issuer of the directive information for ingestion by the at least one particular living being according to at least one requirement including at least one pharmaceutical medication to treat a respiratory infection for a young child with a respiratory infection that requires treatment.

50. A method, comprising:
providing a vending machine, including at least:
at least one production machine configured for preparation of one or more ingestible products incorporating one or more controlled substances;
receiving at least one identity of at least one particular living being;
receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being;
obtaining at least one verification of controlled substance directive issuance authorization of the issuer of the directive information;
obtaining at least one verification of authorship of the directive information by the issuer;
controlling the at least one production machine to prepare the at least one particular ingestible product, including at least incorporating the at least one controlled substance, based at least partially on (i) the receiving the at least one identity, (ii) the receiving the directive information, (iii) the obtaining the at least one verification of controlled substance directive issuance authorization, and (iv) the obtaining the at least one verification of authorship;
recording occurrence information indicative of preparation of the at least one particular ingestible product via the at least one production machine; and
controlling at least one dispensing, by the at least one production machine, of the at least one prepared particular ingestible product for collection by the at least one particular living being,
wherein at least one of the receiving, obtaining, controlling, or recording is at least partially implemented via at least one processing device.

51. A system, comprising:
a vending machine, including at least:
at least one production machine configured for preparation of one or more ingestible products incorporating one or more controlled substances at least one processing device; and at least one non-transitory computer-readable medium including at least one or more instructions which, when executed on the at least one processing device, causes the at least one processing device to perform one or more operations including at least:

receiving at least one identity of at least one particular living being;

receiving directive information relating to the at least one particular living being, the directive information including at least one or more indications of identity of an issuer of the directive information and one or more indications of at least one particular ingestible product including at least one controlled substance for preparation via the at least one production machine, the at least one particular ingestible product designated by the issuer of the directive information for ingestion by the at least one particular living being;

obtaining at least one verification of controlled substance directive issuance authorization of the issuer of the directive information;

obtaining at least one verification of authorship of the directive information by the issuer;

controlling the at least one production machine to prepare the at least one particular ingestible product, including at least incorporating the at least one controlled substance, based at least partially on (i) the receiving the at least one identity, (ii) the receiving the directive information, (iii) the obtaining the at least one verification of controlled substance directive issuance authorization, and (iv) the obtaining the at least one verification of authorship;

recording occurrence information indicative of preparation of the at least one particular ingestible product via the at least one production machine; and controlling at least one dispensing, by the at least one production machine, of the at least one prepared particular ingestible product for collection by the at least one particular living being.

* * * * *